United States Patent
Fatheree et al.

(10) Patent No.: US 10,519,153 B2
(45) Date of Patent: *Dec. 31, 2019

(54) FUSED IMIDAZO-PIPERIDINE JAK INHIBITORS

(71) Applicant: THERAVANCE BIOPHARMA R&D IP, LLC, South San Francisco, CA (US)

(72) Inventors: Paul R. Fatheree, San Francisco, CA (US); Gary E. L. Brandt, Alameda, CA (US); Cameron Smith, San Bruno, CA (US); Steven D. E. Sullivan, San Francisco, CA (US); Lori Jean Van Orden, San Francisco, CA (US); Melanie A. Kleinschek, San Francisco, CA (US); Glenn D. Crater, Raleigh, NC (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/225,473

(22) Filed: Dec. 19, 2018

(65) Prior Publication Data

US 2019/0127371 A1    May 2, 2019

Related U.S. Application Data

(63) Continuation of application No. 15/915,434, filed on Mar. 8, 2018, now Pat. No. 10,208,040.

(60) Provisional application No. 62/469,073, filed on Mar. 9, 2017.

(51) Int. Cl.
| C07D 471/04 | (2006.01) |
| C07D 519/00 | (2006.01) |
| A61P 11/06  | (2006.01) |
| A61P 11/00  | (2006.01) |

(52) U.S. Cl.
CPC ............ *C07D 471/04* (2013.01); *A61P 11/00* (2018.01); *A61P 11/06* (2018.01); *C07D 519/00* (2013.01)

(58) Field of Classification Search
CPC .................................................... C07D 471/04
See application file for complete search history.

(56) References Cited

U.S. PATENT DOCUMENTS

| 6,534,524 | B1 | 3/2003 | Kania et al. |
| 6,884,890 | B2 | 4/2005 | Kania et al. |
| 7,884,109 | B2 | 2/2011 | Ohlmeyer et al. |
| 8,450,340 | B2 | 5/2013 | Hood et al. |
| 8,575,336 | B2 | 11/2013 | Coe et al. |
| 8,648,069 | B2 | 2/2014 | Akritopoulou-Zanze |
| 8,895,544 | B2 | 11/2014 | Coe et al. |
| 10,100,049 | B2 | 10/2018 | Fatheree et al. |
| 10,208,040 | B2 * | 2/2019 | Fatheree ................. A61P 11/00 |
| 2005/0090529 | A1 | 4/2005 | McAlpine et al. |
| 2015/0158864 | A1 | 6/2015 | Thorarensen et al. |
| 2015/0329542 | A1 | 11/2015 | Coe et al. |
| 2016/0289196 | A1 | 10/2016 | Choi et al. |
| 2018/0258087 | A1 | 9/2018 | Fatheree et al. |
| 2018/0258088 | A1 | 9/2018 | Fatheree et al. |
| 2018/0311223 | A1 | 11/2018 | Dabros et al. |
| 2018/0311226 | A1 | 11/2018 | Thalladi et al. |
| 2018/0311255 | A1 | 11/2018 | Fatheree et al. |

FOREIGN PATENT DOCUMENTS

| JP | 2010111624 A | 5/2010 |
| WO | 2005009389 A2 | 2/2005 |
| WO | 2010114971 A1 | 10/2010 |
| WO | 2013014567 A1 | 1/2013 |
| WO | 2015173683 A1 | 11/2015 |
| WO | 2016026078 A1 | 2/2016 |
| WO | 2017077283 A1 | 5/2017 |

(Continued)

OTHER PUBLICATIONS

Abcouwer, "Angiogenic factors and cytokines in diabetic retinopathy", J Clin Cell Immunol, Supplement 1: 1-12 (2013).

(Continued)

*Primary Examiner* — Laura L Stockton
(74) *Attorney, Agent, or Firm* — Jeffrey A. Hagenah; Florence Jovic

(57) ABSTRACT

The invention provides compounds of formula (I):

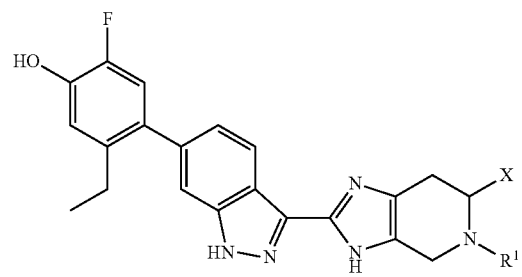

where the variables are defined in the specification, or a pharmaceutically-acceptable salt thereof, that are useful as JAK kinase inhibitors. The invention also provides pharmaceutical compositions comprising such compounds, methods of using such compounds to treat respiratory diseases, and processes and intermediates useful for preparing such compounds.

22 Claims, No Drawings

(56) References Cited

FOREIGN PATENT DOCUMENTS

WO          2017077288 A1          5/2017

OTHER PUBLICATIONS

Bao et al., "The involvement of the JAK-STAT signaling pathway in chronic inflammatory skin disease atopic dermatitis", JAK-STAT, 2(3): e24137-1-e24137-8 (2013).
Berastegui et al., "BALF cytokines in different phenotypes of chronic lung allograft dysfunction in lung transplant patients", Clinical Transplantation, 31: e12898 (2017).
Coghill et al., "Effector CD4+ T cells, the cytokines they generate, and GVHD: something old and something new", Blood, 117(12): 3268-3276 (Mar. 24, 2011).
Cottin, "Eosinophilic lung diseases", Clin Chest Med, 37: 535-556 (2016).
Craiglow et al., "Tofacitinib citrate for the treatment of vitiligo: A pathogenesis-directed therapy", JAMA Dermatology, 151: 1110-1112 (2015).
De Nitto et al., "Involvement of interleukin-15 and interleukin-21, two gamma-chain-related cytokines, in celiac disease", World J Gastroenterol, 15(37): 4609-4614 (Oct. 7, 2009).
El-Hashemite et al., "Interferon-gamma-Jak-Stat signaling in pulmonary lymphangioleiomyomatosis and renal angiomyolipoma", Am J Respir Cell Mol Biol, 33: 227-230 (2005).
El-Hashemite et al., "Perturbed IFN-gamma-Jak-signal transducers and activators of transcription signaling in tuberous sclerosis mouse models: Synergistic effects of rapamycin-IFN-gamma treatment", Cancer Research, 64: 3436-3443 (May 15, 2004).
Fang et al., "Interleukin-6-572C/G polymorphism is associated with serum interleukin-6 levels and risk of idiopathic pulmonary arterial hypertension", Journal of the American Society of Hypertension, 11(3): 171-177 (2017).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Fenwick et al., "Effect of JAK inhibitors on release of CXCL9, CXCL10 and CXCL11 from human airway epithelial cells", PLOS One, 10(6): e0128757 (2015).
Foloppe et al., "Identification of a buried pocket for potent and selective inhibition of Chk1: Prediction and verification", Bioorganic & Medicinal Chemistry, 14: 1792-1804 (2006).
Funatsu et al., "Association of vitreous inflammatory factors with diabetic macular edema", Ophthalmology, 116: 73-79 (2009).
Gauthier et al., "Update on chronic lung allograft dysfunction", Curr Transplant Rep, 3(3): 185-191 (Sep. 2016).
Horai et al, "Cytokines in autoimmune uveitis", Journal of Interferon & Cytokine Research, 31(10): 733-744 (2011).
Huang et al., "Glycoprotein 130 inhibitor ameliorates monocrotalline-induced pulmonary hypertension in rats", Canadian Journal of Cardiology, 32: 1356.e1-1356.e10 (2016).
Jones et al., "Design and synthesis of a Pan-Janus kinase inhibitor clinical candidate (PF-06263276) suitable for inhaled and topical delivery for the treatment of inflammatory diseases of the lungs and skin", J. Med. Chem., 60: 767-786 (2017).
Knickelbein et al., "Inflammatory mechanisms of age-related macular degeneration", International Ophthalmology Clinics, 55(3): 63-78 (2015).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
McBride et al., "Design and structure-activity relationship of 3-benzimidazol-2-yl-1H-indazoles as inhibitors of receptor tyrosine kinases", Bioorganic & Medicinal Chemistry Letters, 16: 3595-3599 (2006).
McBride et al., "3-Benzimidazol-2-yl-1H-indazoles as potent c-ABL inhibitors", Bioorganic & Medicinal Chemistry Letters, 16: 3789-3792 (2006).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Owen et al., "Soluble mediators of diabetic macular edema: The diagnostic role of aqueous VEGF and cytokine levels in diabetic macular edema", Curr Diab Rep, 13(4): 476-480 (Aug. 2013).
Reimund et al., "Mucosal inflammatory cytokine production by intestinal biopsies in patients with ulcerative colitis and Crohn's disease", Journal of Clinical Immunology, 16(3): 144-150 (1996).
Shino et al., "The prognostic importance of CXCR3 chemokine during organizing pneumonia on the risk of chronic lung allograft dysfunction after lung transplantation", PLOS One, 12(7): e0180281 (2017).
Simov et al., "Structure-based design and development of (benz)imidazole pyridones as JAK1-selective kinase inhibitors", Bioorganic & Medicinal Chemistry Letters, 26: 1803-1808 (2016).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
Tanaka et al., "New insight into mechanisms of pruritus from molecular studies on familial primary localized cutaneous amyloidosis", British Journal of Dermatology, 161: 1217-1224 (2009).
Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19: 908-911 (2009).
Vincenti et al., "Randomized phase 2b trial of tofacitinib (CP-690,550) in de novo kidney transplant patients: Efficacy, renal function and safety at 1 year", American Journal of Transplantation, 12: 2446-2456 (2012).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).
Yan et al., "Discovery of 3-(5'-Substituted)-benzimidazol-5-(1-(3,5-dichloropyridin-4-yl)ethoxy)-1H-indazoles as potent fibroblast growth factor receptor inhibitors: Design, synthesis, and biological evaluation", J. Med. Chem., 59: 6690-6708 (2016).
Yano et al., "Ipilimumab augments antitumor activity of bispecific antibody-armed T cells", Journal of Translational Medicine, 12: 191 (2014).

(56) References Cited

OTHER PUBLICATIONS

Zeiser et al., "Ruxolitinib in corticosteroid-refractory graft-versus-host disease after allogeneic stem cell transplantation a multi-center survey", Leukemia, 29(10): 2062-2068 (Oct. 2015).
Zhou et al., "Cytokines and Behcet's Disease", Autoimmunity Reviews, 11: 699-704 (2012).
International Search Report and the Written Opinion for PCT application No. PCT/US2018/021492 dated May 22, 2018.

\* cited by examiner

FUSED IMIDAZO-PIPERIDINE JAK INHIBITORS

CROSS-REFERENCE TO RELATED APPLICATIONS

This application is a continuation application of U.S. Ser. No. 15/915,434, filed on Mar. 8, 2018, now allowed, which application claims the benefit of U.S. Provisional Application No. 62/469,073, filed on Mar. 9, 2017, the disclosures of which are incorporated herein by reference in their entirety.

BACKGROUND OF THE INVENTION

Field of the Invention

The invention is directed to compounds useful as JAK kinase inhibitors. The invention is also directed to pharmaceutical compositions comprising such compounds, methods of using such compounds to treat respiratory diseases, and processes and intermediates useful for preparing such compounds.

State of the Art

Asthma is a chronic disease of the airways for which there are no preventions or cures. The disease is characterized by inflammation, fibrosis, hyper-responsiveness, and remodeling of the airways, all of which contribute to airflow limitation. An estimated 300 million people worldwide suffer from asthma and it is estimated that the number of people with asthma will grow by more than 100 million by 2025. In the United States, asthma afflicts about 6% to 8% of the population, making it one of the most common chronic diseases in the country. Although most patients can achieve control of asthma symptoms with the use of inhaled corticosteroids that may be combined with a leukotriene modifier and/or a long acting beta agonist, there remains a subset of patients with severe asthma whose disease is not controlled by conventional therapies. Severe persistent asthma is defined as disease that remains uncontrolled on high doses of inhaled corticosteroids. While severe asthmatics are estimated to account for approximately 5% of all asthma sufferers, they have a high risk of morbidity and mortality and are responsible for a disproportionate share of health care resource utilization among asthmatics. There remains a need for novel therapies to treat these patients.

Cytokines are intercellular signaling molecules which include chemokines, interferons, interleukins, lymphokines, and tumour necrosis factor. Cytokines are critical for normal cell growth and immunoregulation but also drive immune-mediated diseases and contribute to the growth of malignant cells. Elevated levels of many cytokines have been implicated in the pathology of asthma inflammation. For example, antibody-based therapies targeted at interleukins (IL)-5, and 13 have been shown to provide clinical benefit in subsets of severe asthma patients. Among the cytokines implicated in asthma inflammation, many act through signaling pathways dependent upon the Janus family of tyrosine kinases (JAKs), which signal through the Signal Transducer and Activator of Transcription (STAT) family of transcription factors. Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF).

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings. Each of the four members of the JAK family is implicated in the signaling of at least one of the cytokines associated with asthma inflammation. Consequently, a chemical inhibitor with pan-activity against all members of the JAK family could modulate a broad range of pro-inflammatory pathways that contribute to severe asthma.

However, the broad anti-inflammatory effect of such inhibitors could suppress normal immune cell function, potentially leading to increased risk of infection. Evidence of increased infection risk has been observed with the JAK inhibitor tofacitinib, which is dosed orally for the treatment of rheumatoid arthritis. In asthma, inflammation is localized to the respiratory tract. Inflammation of the airways is characteristic of other respiratory diseases in addition to asthma. Chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, and sarcoidosis are also respiratory tract diseases in which the pathophysiology is believed to be related to JAK-signaling cytokines. Local administration of a JAK inhibitor to the lungs by inhalation offers the potential to be therapeutically efficacious by delivering a potent anti-cytokine agent directly to the site of action, limiting systemic exposure and therefore limiting the potential for adverse systemic immunosuppression. The need remains for a potent JAK inhibitor suitable for local administration to the lungs for treatment of respiratory disease.

JAK-signaling cytokines also play a major role in the activation of T cells, a sub-type of immune cells that is central to many immune processes. Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipients T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., Curr Transplant Rep., 2016, 3(3), 185-191). CLAD is poorly responsive to treatment and therefore, there remains a need for effective compounds capable of preventing or treating this condition.

Several JAK-dependent cytokines such as IFNγ and IL-5 are up-regulated in CLAD and lung transplant rejection (Berastegui et al, *Clin Transplant.* 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, *PLOS One,* 2017, 12 (7), e0180281). Systemic JAK inhibition has been shown to be effective in kidney transplant rejection (Vicenti et al., *American Journal of Transplantation,* 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, *Leukemia,* 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD.

SUMMARY OF THE INVENTION

In one aspect, the invention provides novel compounds having activity as JAK kinase inhibitors.

Accordingly, the invention provides a compound of formula (I):

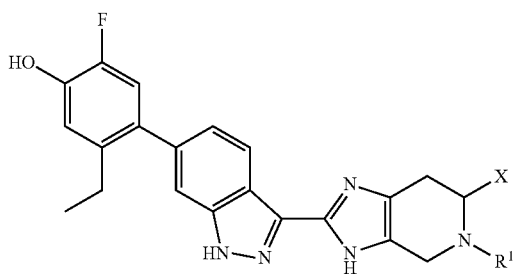

(I)

wherein:
$R^1$ is selected from hydrogen, $C_{1-3}$alkyl, and $C_{3-6}$cycloalkyl, and X is selected from —C(O)$R^2$ and —CH$_2R^{16}$, or $R^1$ is selected from —(CH$_2$)$_2$NR$^{20}$R$^{21}$ and a 4- to 6-membered heterocyclyl containing one nitrogen atom, wherein the nitrogen atom is optionally substituted with $R^{22}$, and X is selected from —CH$_2$OR$^{23}$ and —C(O)OR$^{24}$, wherein
$R^2$ is selected from —NR$^{13}$R$^{14}$ and —OR$^{15}$,
$R^{13}$ and $R^{14}$ taken together with the nitrogen atom to which they are attached form a 6- or 7-membered monocyclic or bicyclic heterocyclyl containing one additional nitrogen atom, wherein the additional nitrogen atom is substituted with $R^3$ and the heterocyclyl is optionally substituted with one or two $R^4$, or $R^{13}$ and $R^{14}$ taken together with the nitrogen atom to which they are attached form a 5- to 6-membered heterocyclyl, wherein the heterocyclyl is optionally substituted with —NR$^5$R$^6$ and $R^7$, or $R^{13}$ and $R^{14}$ taken together with the nitrogen atom to which they are attached form morpholinyl, or $R^{13}$ is $R^8$ and $R^{14}$ is $R^9$, $R^3$ is selected from hydrogen, $C_{3-6}$cycloalkyl, and $C_{1-3}$alkyl, wherein $C_{1-3}$alkyl is optionally substituted with —OH or —OC$_{1-3}$alkyl, $R^4$ is $C_{1-3}$alkyl, wherein $C_{1-3}$alkyl is optionally substituted with —OH, $R^5$ and $R^6$ are independently $C_{1-3}$alkyl or $R^5$ and $R^6$ taken together with the nitrogen atom to which they are attached form a 5- or 6-membered heterocyclyl optionally including an oxygen atom, $R^7$ is $C_{1-3}$alkyl, optionally substituted with a 5- or 6-membered heterocyclyl containing one nitrogen atom, $R^8$ is hydrogen or $C_{1-3}$alkyl, $R^9$ is —(CH$_2$)$_2$NR$^{10}$R$^{11}$ or a 4- to 6-membered heterocyclyl containing one nitrogen atom, wherein the nitrogen atom is substituted with $R^{12}$, $R^{10}$ and $R^{11}$ are independently $C_{1-3}$alkyl or $R^{10}$ and $R^{11}$ taken together with the nitrogen atom to which they are attached form a 5- or 6-membered heterocyclyl, $R^{12}$ is $C_{1-3}$alkyl or $C_{3-6}$cycloalkyl, wherein $C_{1-3}$alkyl is optionally substituted with —OH, $R^{15}$ is selected from $C_{1-3}$alkyl, $C_{3-6}$cycloalkyl, and a 5- or 6-membered heterocyclyl including one heteroatom selected from nitrogen and oxygen, wherein $C_{1-3}$alkyl is optionally substituted with —OH or —N(C$_{1-3}$alkyl)$_2$, and a 5- or 6-membered heterocyclyl is optionally substituted with $C_{1-3}$alkyl, $R^{16}$ is selected from —NR$^{17}$R$^{18}$ and —OR$^{19}$, $R^{17}$ and $R^{18}$ are independently $C_{1-4}$alkyl or $C_{3-5}$cycloalkyl or $R^{17}$ and $R^{18}$ taken together with the nitrogen atom to which they are attached form a 5- or 6-membered heterocyclyl optionally including an oxygen atom, wherein the heterocyclyl is optionally substituted with $C_{1-3}$alkyl, $R^{19}$, $R^{20}$, $R^{21}$, $R^{22}$, $R^{23}$, and $R^{24}$ are independently selected from hydrogen and $C_{1-3}$alkyl, or a pharmaceutically-acceptable salt thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated.

The invention also provides a pharmaceutical composition comprising a compound of the invention and a pharmaceutically-acceptable carrier.

The invention also provides a method of treating respiratory disease, in particular, asthma, in a mammal, the method comprising administering to the mammal a therapeutically effective amount of a compound or of a pharmaceutical composition of the invention. In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating respiratory disease in a mammal.

DETAILED DESCRIPTION OF THE INVENTION

Among other aspects, the invention provides JAK kinase inhibitors of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect, $R^1$ is selected from hydrogen, $C_{1-3}$alkyl, and $C_{3-6}$cycloalkyl.

In another specific aspect, $R^1$ is selected from hydrogen and $C_{1-3}$alkyl. In yet another specific aspect, $R^1$ is $C_{1-3}$alkyl.

Specific values of $R^1$ include, but are not limited to, methyl, ethyl, n-propyl, and isopropyl.

In a specific aspect, $R^1$ is selected from hydrogen and $C_{1-3}$alkyl and X is —C(O)$R^2$, wherein $R^2$ is —NR$^{13}$R$^{14}$, wherein $R^{13}$ and $R^{14}$ taken together with the nitrogen atom to which they are attached form a 6- or 7-membered monocyclic or bicyclic heterocyclyl containing one additional nitrogen atom, wherein the additional nitrogen atom is substituted with $R^3$ and the heterocyclyl is optionally substituted with one or two $R^4$; $R^3$ is selected from hydrogen, $C_{3-6}$cycloalkyl, and $C_{1-3}$alkyl, wherein $C_{1-3}$alkyl is optionally substituted with —OH or —OC$_{1-3}$alkyl; and $R^4$ is $C_{1-3}$alkyl, optionally substituted with —OH.

Specific values of $R^3$ include, but are not limited to, hydrogen, cyclopropyl, cyclobutyl, cyclopentyl, cyclohexyl, methyl, ethyl, propyl, isopropyl, tert-butyl, and hydroxyethyl.

Exemplary values of $R^4$ include, but are not limited to, methyl, ethyl, and hydroxymethyl.

In another specific aspect, $R^1$ is selected from hydrogen and $C_{1-3}$alkyl or $R^1$ is $C_{1-3}$alkyl and X is —C(O)$R^2$ wherein $R^2$ is selected from

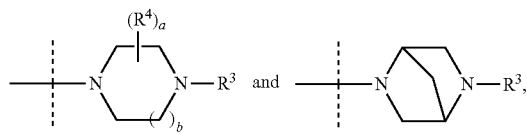

wherein $R^3$ is hydrogen or $C_{1-3}$alkyl, wherein $C_{1-3}$alkyl is optionally substituted with —OH; a is 0, 1, or 2; b is 1 or 2; provided that when a is 0, $R^3$ is $C_{1-3}$alkyl, wherein $C_{1-3}$alkyl is optionally substituted with —OH; and $R^4$, when present, is $C_{1-3}$alkyl;

In yet another aspect, $R^1$ is selected from hydrogen and $C_{1-3}$alkyl or $R^1$ is $C_{1-3}$alkyl and X is —C(O)$R^2$ wherein $R^2$ is selected from

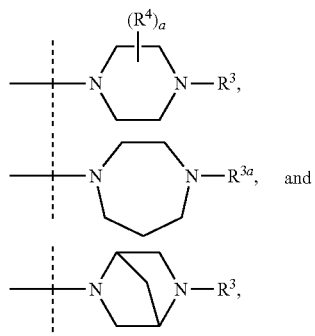

wherein $R^3$ is $C_{1-3}$alkyl or —(CH$_2$)$_2$OH; $R^{3a}$ is $C_{1-3}$alkyl; a is 0, 1, or 2; and $R^4$, when present, is $C_{1-3}$alkyl.

In a specific aspect, $R^1$ is selected from hydrogen and $C_{1-3}$alkyl and X is —C(O)$R^2$ wherein $R^2$ is —NR$^{13}$R$^{14}$, wherein $R^{13}$ and $R^{14}$ taken together with the nitrogen atom to which they are attached form a 5- to 6-membered heterocyclyl, wherein the heterocyclyl is optionally substituted with —NR$^5$R$^6$ and $R^7$; $R^5$ and $R^6$ are independently $C_{1-3}$alkyl or $R^5$ and $R^6$ taken together with the nitrogen atom to which they are attached form a 5- or 6-membered heterocyclyl optionally including an oxygen atom; and $R^7$ is $C_{1-3}$alkyl, optionally substituted with a 5- or 6-membered heterocyclyl containing one nitrogen atom. In a particular aspect, $R^7$ is $C_{1-3}$alkyl, optionally substituted with pyrrolidinyl.

In a specific aspect, $R^1$ is selected from hydrogen and $C_{1-3}$alkyl and X is —C(O)$R^2$ wherein $R^2$ is

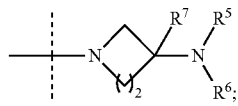

wherein $R^5$ and $R^6$ are independently $C_{1-3}$alkyl or $R^5$ and $R^6$ taken together form —(CH$_2$)$_{4-5}$— and $R^7$ is hydrogen or $C_{1-3}$alkyl.

In another specific aspect, $R^1$ is selected from hydrogen and $C_{1-3}$alkyl and X is —C(O)$R^2$ wherein $R^2$ is a group selected from:

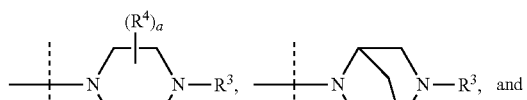
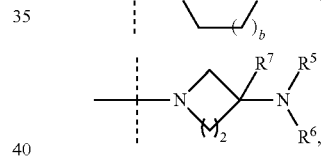

wherein $R^3$ is hydrogen or $C_{1-3}$alkyl, wherein $C_{1-3}$alkyl is optionally substituted with —OH; a is 0, 1, or 2; b is 1 or 2; $R^4$, when present, is $C_{1-3}$alkyl; provided that when a is 0, $R^3$ is $C_{1-3}$alkyl, wherein $C_{1-3}$alkyl is optionally substituted with —OH; $R^5$ and $R^6$ are independently $C_{1-3}$ alkyl or $R^5$ and $R^6$ taken together form —(CH$_2$)$_{4-5}$—; and $R^7$ is hydrogen or $C_{1-3}$alkyl.

In a specific aspect, $R^1$ is selected from hydrogen and $C_{1-3}$alkyl and X is —C(O)$R^2$ wherein $R^2$ is —NR$^{13}$R$^{14}$, wherein $R^{13}$ and $R^{14}$ taken together with the nitrogen atom to which they are attached form morpholinyl.

In a specific aspect, $R^1$ is selected from hydrogen and $C_{1-3}$alkyl and X is —C(O)$R^2$ wherein $R^2$ is —NR$^{13}$R$^{14}$, wherein $R^{13}$ is $R^8$ and $R^{14}$ is $R^9$; $R^8$ is hydrogen or $C_{1-3}$alkyl; $R^9$ is —(CH$_2$)$_2$NR$^{10}$R$^{11}$ or a 4- to 6-membered heterocyclyl containing one nitrogen atom. wherein the nitrogen atom is substituted with $R^{12}$; $R^{10}$ and $R^{11}$ are independently $C_{1-3}$alkyl or $R^{10}$ and $R^{11}$ taken together with the nitrogen atom to which they are attached form a 5- or 6-membered heterocyclyl; and $R^{12}$ is $C_{1-3}$alkyl or $C_{3-6}$cycloalkyl, wherein $C_{1-3}$alkyl is optionally substituted with —OH.

In another specific aspect, $R^1$ is selected from hydrogen and $C_{1-3}$alkyl and X is —C(O)$R^2$ wherein $R^2$ is —NR$^{13}$R$^{14}$, wherein $R^{13}$ is $R^8$ and $R^{14}$ is $R^9$; $R^8$ is $C_{1-3}$alkyl; $R^9$ is —(CH$_2$)$_2$NR$^{10}$R$^{11}$ or piperidinyl, wherein piperidinyl is substituted at the nitrogen atom with $R^{12}$; $R^{10}$ and $R^{11}$ are independently $C_{1-3}$alkyl; and $R^{12}$ is $C_{1-3}$alkyl or $C_{3-6}$cycloalkyl, wherein $C_{1-3}$alkyl is optionally substituted with —OH.

In yet another specific aspect, $R^1$ is selected from hydrogen and $C_{1-3}$alkyl and X is —C(O)$R^2$ wherein $R^2$ is —N$R^{13}R^{14}$, wherein $R^{13}$ is $R^8$ and $R^{14}$ is $R^9$; $R^8$ is —CH$_3$; $R^9$ is —(CH$_2$)$_2$N$R^{10}R^{11}$ or

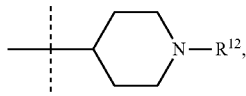

$R^{10}$ and $R^{11}$ are independently $C_{1-3}$alkyl, and $R^{12}$ is $C_{1-3}$alkyl.

In a specific aspect, $R^1$ is selected from hydrogen and $C_{1-3}$alkyl and X is —C(O)$R^2$ wherein $R^2$ is —O$R^{15}$, wherein $R^{15}$ is selected from $C_{1-3}$alkyl, $C_{3-6}$cycloalkyl, and a 5- or 6-membered heterocyclyl including one heteroatom selected from nitrogen and oxygen, wherein $C_{1-3}$alkyl is optionally substituted with —OH or —N($C_{1-3}$alkyl)$_2$, and a 5- or 6-membered heterocyclyl is optionally substituted with $C_{1-3}$alkyl.

In another specific aspect, $R^1$ is selected from hydrogen and $C_{1-3}$alkyl and X is —C(O)$R^2$ wherein $R^2$ is —O$R^{15}$, wherein $R^{15}$ is selected from $C_{1-3}$alkyl, $C_{3-6}$cycloalkyl, and a 5- or 6-membered heterocyclyl including one heteroatom selected from nitrogen and oxygen, wherein $C_{1-3}$alkyl is optionally substituted with —OH, and a 5- or 6-membered heterocyclyl is optionally substituted with $C_{1-3}$alkyl.

In a specific aspect, $R^1$ is selected from hydrogen and $C_{1-3}$alkyl and X is —CH$_2R^{16}$, wherein $R^{16}$ is —N$R^{17}R^{18}$, wherein $R^{17}$ and $R^{18}$ are independently $C_{1-4}$alkyl or $C_{3-5}$cycloalkyl or $R^{17}$ and $R^{18}$ taken together with the nitrogen atom to which they are attached form a 5- or 6-membered heterocyclyl optionally including an oxygen atom, wherein the heterocyclyl is optionally substituted with $C_{1-3}$alkyl.

In another specific aspect, $R^1$ is selected from hydrogen and $C_{1-3}$alkyl and X is —CH$_2R^{16}$, wherein $R^{16}$ is —N$R^{17}R^{18}$, wherein $R^{17}$ and $R^{18}$ are independently $C_{1-4}$alkyl or $C_{3-5}$cycloalkyl or $R^{17}$ and $R^{18}$ taken together with the nitrogen atom to which they are attached form morpholinyl or a 5- or 6-membered heterocyclyl, wherein the heterocyclyl is optionally substituted with $C_{1-3}$alkyl.

In a specific aspect, R' is selected from hydrogen and $C_{1-3}$alkyl and X is —CH$_2R^{16}$, wherein $R^{16}$ is —O$R^{19}$, wherein $R^{19}$ is hydrogen or $C_{1-3}$alkyl.

In a specific aspect, $R^1$ is selected from —(CH$_2$)$_2$N$R^{20}R^{21}$ and a 4- to 6-membered heterocyclyl containing one nitrogen atom, wherein the nitrogen atom is optionally substituted with $R^{22}$ and X is —CH$_2$O$R^{23}$, wherein $R^{20}$, $R^{21}$, $R^{22}$, and $R^{23}$ are independently selected from hydrogen and $C_{1-3}$alkyl.

In a specific aspect, $R^1$ is selected from —(CH$_2$)$_2$N$R^{20}R^{21}$ and a 4- to 6-membered heterocyclyl containing one nitrogen atom, wherein the nitrogen atom is optionally substituted with $R^{22}$ and X is —C(O)O$R^{24}$, wherein $R^{20}$, $R^{21}$, $R^{22}$, and $R^{24}$ are independently selected from hydrogen and $C_{1-3}$alkyl.

In a specific aspect, R' is selected from —(CH$_2$)$_2$N$R^{20}R^{21}$,

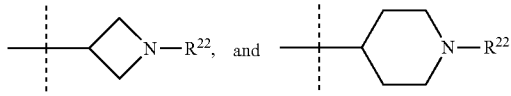

and X is selected from —CH$_2$O$R^{23}$ and —C(O)O$R^{24}$, wherein $R^{20}$, $R^{21}$, $R^{22}$, $R^{23}$, and $R^{24}$ are independently selected from hydrogen and $C_{1-3}$alkyl.

In another aspect, the invention provides a compound of formula (II):

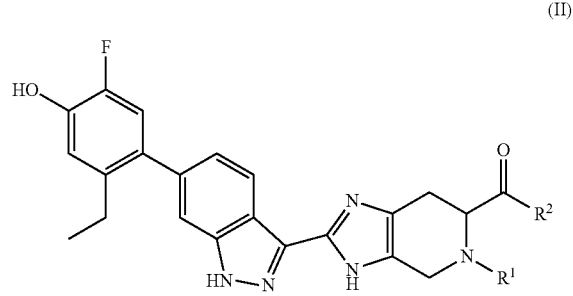

wherein:
$R^1$ is $C_{1-3}$alkyl;
$R^2$ is a group selected from:

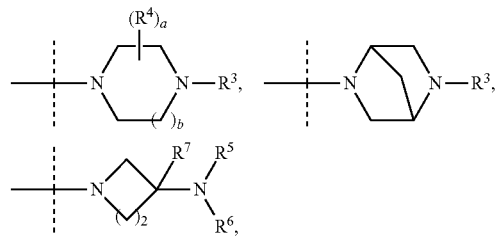

and —N$R^8R^9$,
wherein
$R^3$ is hydrogen or $C_{1-3}$alkyl, wherein $C_{1-3}$alkyl is optionally substituted with —OH,
a is 0, 1, or 2,
b is 1 or 2,
$R^4$, when present, is $C_{1-3}$alkyl,
provided that when a is 0, $R^3$ is $C_{1-3}$alkyl, wherein $C_{1-3}$alkyl is optionally substituted with —OH,
$R^5$ and $R^6$ are independently $C_{1-3}$alkyl or $R^5$ and $R^6$ taken together form —(CH$_2$)$_{4-5}$—,
$R^7$ is hydrogen or $C_{1-3}$alkyl,
$R^8$ is —CH$_3$,
$R^9$ is —(CH$_2$)$_2$N$R^{10}R^{11}$ or

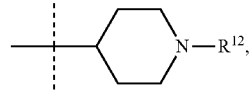

$R^{10}$ and $R^{11}$ are independently $C_{1-3}$alkyl, and
$R^{12}$ is $C_{1-3}$alkyl;
or a pharmaceutically-acceptable salt thereof.

In yet another aspect, the invention provides a compound selected from the following compounds:
((S)-2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)((1S,4S)-5-methyl-2,5-diazabicyclo-[2.2.1]heptan-2-yl)methanone,
((S)-3-(dimethylamino)pyrrolidin-1-yl)((S)-5-ethyl-2-(6-(2-ethyl-5-fluoro-4-hydroxyphenyl)-1H-indazol-3-yl)-4,5,6,7-tetrahydro-3H-imidazo[4,5-c]pyridin-6-yl)methanone, (S)-(2-(6-(2-ethyl-5-fluoro-4-hydroxyphenyl)-1H-indazol-3-yl)-5-isopropyl-4,5,6,7-tetrahydro-3H-imidazo[4,5-c]pyridin-6-yl)(4-methyl-1,4-diazepan-1-yl)methanone, ((S)-2-(6-(2-ethyl-5-fluoro-4-hydroxyphenyl)-1H-indazol-3-yl)-5-methyl-4,5,6,7-tetrahydro-3H-imidazo[4,5-c]pyridin-6-yl)((R)-4-(2-hydroxyethyl)-2-methyl-piperazin-1-yl)methanone, (S)-(2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)(4-(2-hydroxyethyl)piperazin-1-yl)methanone, and pharmaceutically-acceptable salts thereof.

In yet another aspect, the invention provides a compound wherein the compound is ((S)-2,4-dimethylpiperazin-1-yl) ((S)-2-(6-(2-ethyl-5-fluoro-4-hydroxyphenyl)-1H-indazol-3-yl)-5-methyl-4,5,6,7-tetrahydro-3H-imidazo[5,4-c]pyridin-6-yl)methanone, or a pharmaceutically-acceptable salt thereof.

In yet another aspect, the invention provides a compound wherein the compound is (R)—N-(2-(diethylamino)ethyl)-5-ethyl-2-(6-(2-ethyl-5-fluoro-4-hydroxyphenyl)-1H-indazol-3-yl)-N-methyl-4,5,6,7-tetrahydro-3H-imidazo[5,4-c]pyridine-6-carboxamide, or a pharmaceutically-acceptable salt thereof.

In yet another aspect, the invention provides a compound wherein the compound is ((S)-2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)((1S,4S)-5-methyl-2,5-diazabicyclo-[2.2.1]heptan-2-yl) of the formula

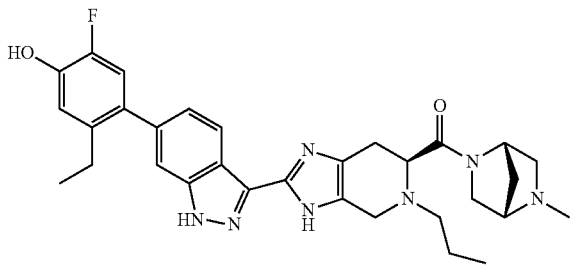 [SMILES: CCCN1Cc2[nH]c(-c3n[nH]c4cc(-c5cc(F)c(O)cc5CC)ccc34)nc2C[C@H]1C(=O)N1C[C@@H]2C[C@H]1CN2C]

or a pharmaceutically-acceptable salt thereof.

In yet another aspect, the invention provides a compound of the formula

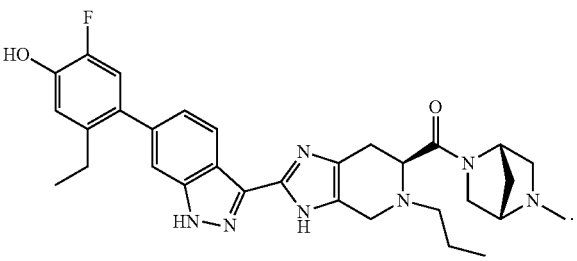 [SMILES: CCCN1Cc2[nH]c(-c3n[nH]c4cc(-c5cc(F)c(O)cc5CC)ccc34)nc2C[C@H]1C(=O)N1C[C@@H]2C[C@H]1CN2C]

In one aspect, the invention provides the compounds of Examples 1, 3, 5, 6, 7, and Tables 1-19 below.

Chemical structures are named herein according to IUPAC conventions as implemented in ChemDraw software (PerkinElmer, Inc., Cambridge, Mass.). For example, the compound of Example 1:

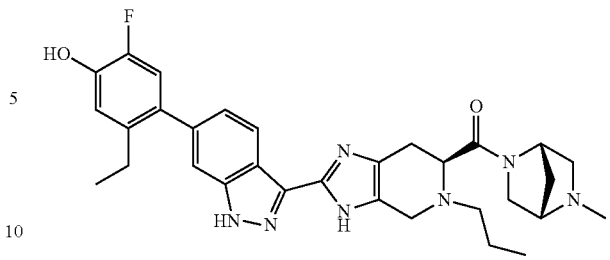

is designated as ((S)-2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)((1S,4S)-5-methyl-2,5-diazabicyclo-[2.2.1]heptan-2-yl)methanone.

Furthermore, the imidazo portion of the tetrahydroimidazopyridine moiety in the structure of formula (I) exists in tautomeric forms, illustrated below for a fragment of the compound of Example 1

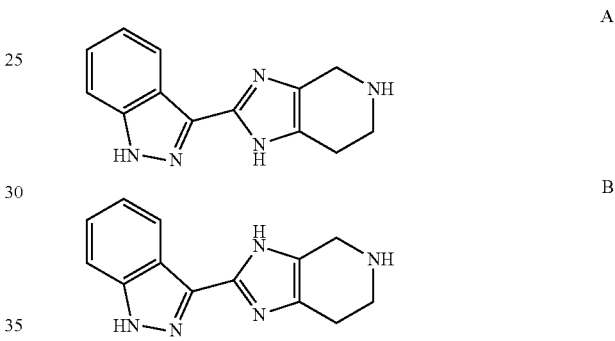

According to the IUPAC convention, these representations give rise to different numbering of the atoms of the imidazole portion: 2-(1H-indazol-3-yl)-4,5,6,7-tetrahydro-1H-imidazo[4,5-c]pyridine (structure A) vs. 2-(1H-indazol-3-yl)-4,5,6,7-tetrahydro-3H-imidazo[4,5-c]pyridine (structure B). It will be understood that although structures are shown, or named, in a particular form, the invention also includes the tautomer thereof.

The compounds of the invention may contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where one or more atom has been replaced or enriched with an atom having the same atomic number but an atomic mass different from the atomic mass that predominates in nature. Examples of isotopes that may be incorporated into a compound of formula (I) include, but are not limited to, $^2$H, $^3$H, $^{11}$C, $^{13}$C, $^{14}$C, $^{13}$N, $^{15}$N, $^{15}$O, $^{17}$O, and $^{18}$O. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}$C, $^{15}$O and $^{13}$N, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl (cBu), cyclopentyl, cyclohexyl, cycloheptyl, cyclooctyl, adamantyl, and the like.

The term "cpropyl" means cyclopropyl.

The term "heterocyclyl", "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclyl groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "halo" means fluoro, chloro, bromo or iodo.

The term "therapeutically effective amount" means an amount sufficient to effect treatment when administered to a patient in need of treatment.

The term "treating" or "treatment" means preventing, ameliorating or suppressing the medical condition, disease or disorder being treated (e.g., a respiratory disease) in a patient (particularly a human); or alleviating the symptoms of the medical condition, disease or disorder.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Numerous protecting groups, and their introduction and removal, are described in T. W. Greene and P. G. M. Wuts, *Protecting Groups in Organic Synthesis*, Third Edition, Wiley, New York General Synthetic Procedures Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

A general method of preparing final compounds of the invention in which the variable X is defined as $-C(O)R^2$ and $R^1$ is $C_{1-3}$alkyl utilizes a key intermediate 1 and an amine of formula 2 as illustrated generally in Scheme 1 and, in particular, for an example in which $R^2$ is defined as

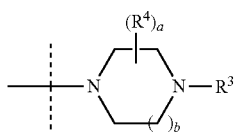

2a to specifically exemplify a representative amide final product of formula (II).

Scheme 1

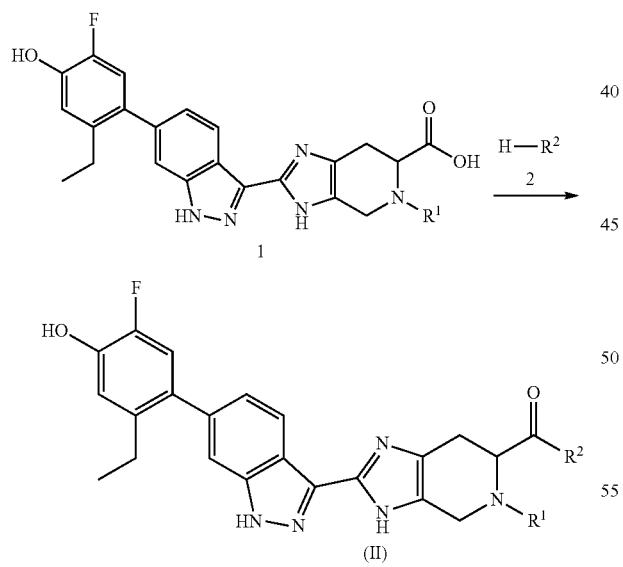

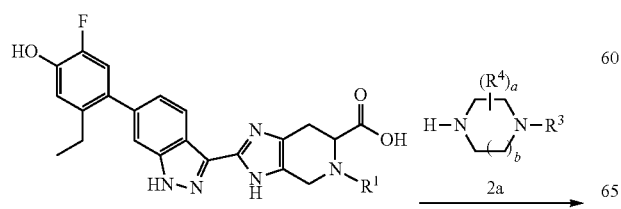

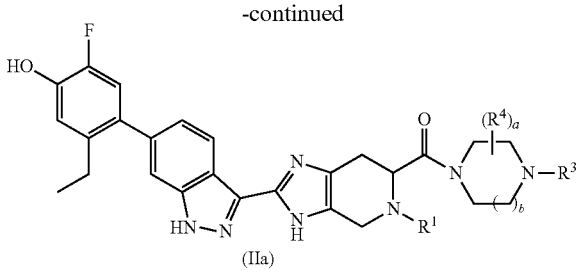

(IIa)

To prepare amide compounds of formula (II), the carboxylic acid of formula 1 is reacted with amine 2 according to typical amide bond formation conditions. Typically, carboxylic acid 1 is contacted with between about 1 and about 4 equivalents of amine 2 in the presence of an excess of base. As shown in the examples below, the amide bond formation reaction may utilize coupling agents, such as N,N,N',N'-tetramethyl-O-(7-azabenzotriazol-1-yl)uronium hexafluorophosphate (HATU) or other amide coupling agents known in the art. The reaction is typically conducted at room temperature for between about 2 and about 24 hours or until the reaction is substantially complete.

Compounds in which the variable X is defined as $-C(O)$ $OR^{15}$ may be prepared by an esterification reaction of the carboxylic acid of formula 1 with an alcohol of formula $HO-R^{15}$ in which the acid 1 is contacted with a large excess of the alcohol, for example 25 equivalents of alcohol, in the presence of a coupling reagent such as HATU and an excess of base. When IV is defined as a heterocyclyl substituted with $C_{1-3}$alkyl, an alcohol reagent lacking the alkyl substituent may be used in the esterification reaction and the alkyl substituent added in a subsequent step.

The carboxylic acid of formula 1 may be prepared as illustrated in Scheme 2

Scheme 2

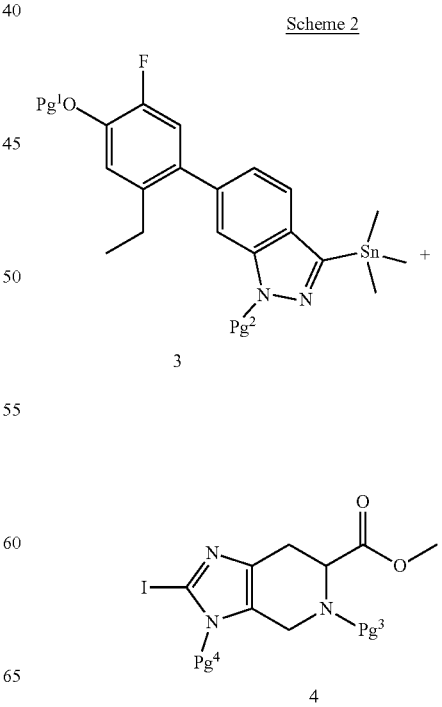

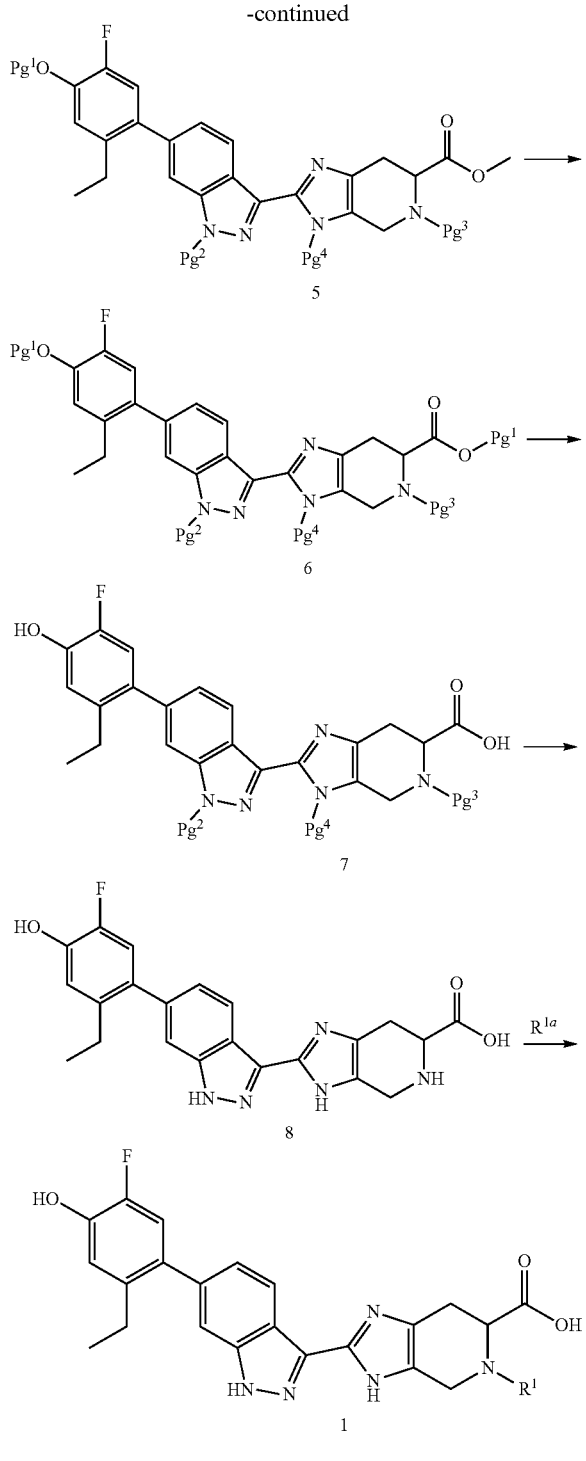

example, at between about 80° C. and about 180° C. for between about 10 and about 24 hours or until the reaction is substantially complete.

When benzyl is used as $Pg^1$, in the next step, the methyl ester of intermediate 5 is converted to a benzyl ester in intermediate 6 by reaction of 5 with benzyl alcohol. Both benzyl protecting groups are conveniently removed by palladium catalyzed hydrogenation to provide intermediate 7 which may be fully deprotected by reaction with acid, typically hydrochloric acid. In a final step, the substituent IV is added by reductive alkylation of intermediate 8 with a reagent $R^{1a}$ where $R^{1a}$ is an aldehyde or ketone defined such that upon reduction, IV is produced. For example, to add a methyl substituent $R^1$, formaldehyde is used as reagent $R^{1a}$, to add an isopropyl moeity as substituent $R^1$, acetone is used as reagent $R^{1a}$. The reaction is typically conducted in the presence of a reducing agent such as sodium cyanoborohydride or sodium triacetoxyborohydride or the like at ambient temperature for a period of about 10 to about 24 hours or until the reaction is substantially complete.

Intermediates 3 and 4 may be prepared from commercial or easily prepared starting materials, as described in detail below. In particular, a process for preparing intermediate 3 in which $Pg^1$ is benzyl and $Pg^2$ is THP uses the Suzuki-Miyaura coupling of compound 9 with compound 10 followed by conventional reactions to add the trimethylstannyl group.

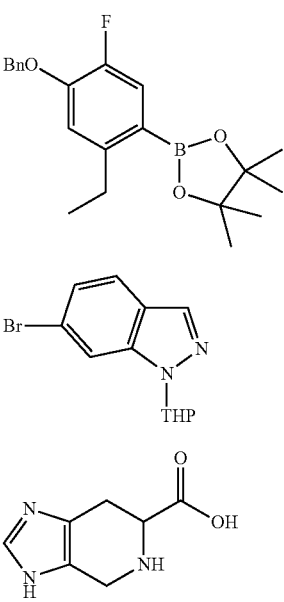

where $Pg^1$ represents a hydroxy-protecting group and $Pg^2$, $Pg^3$, and $Pg^4$ represent different amino-protecting groups. As described in the examples below, a useful choice of protecting groups is benzyl or methyl as $Pg^1$, tetrahydropyranyl (THP) as $Pg^2$, tert-butoxycarbonyl (Boc) or benzyl as $Pg^3$, and [2-(trimethylsilyl)ethoxy]methyl (SEM) as $Pg^4$. The first step of Scheme 2 is the palladium catalyzed Stille coupling of intermediate 3 with intermediate 4 where the phenyl-indazole intermediate 3 has the trimethylstannyl moiety and the reaction partner 4 is iodine substituted. The reaction is typically conducted at elevated temperature, for example, at between about 80° C. and about 180° C. for between about 10 and about 24 hours or until the reaction is substantially complete.

Intermediate 4 may be prepared from compound 11, which is commercially available in racemic and stereospecific forms and may also be prepared from histidine.

A reductive amination reaction to prepare final compounds of the invention in which, for example, the variable X is defined as $-CH_2NR^{14}R^{15}$ is illustrated in Scheme 3 where $R^{14}$ and $R^{15}$ are as defined in formula (I), the remaining variables are as described in Scheme 2 above, and $Pg^1$ may usefully be selected as methyl and $Pg^3$ as Boc.

Scheme 3

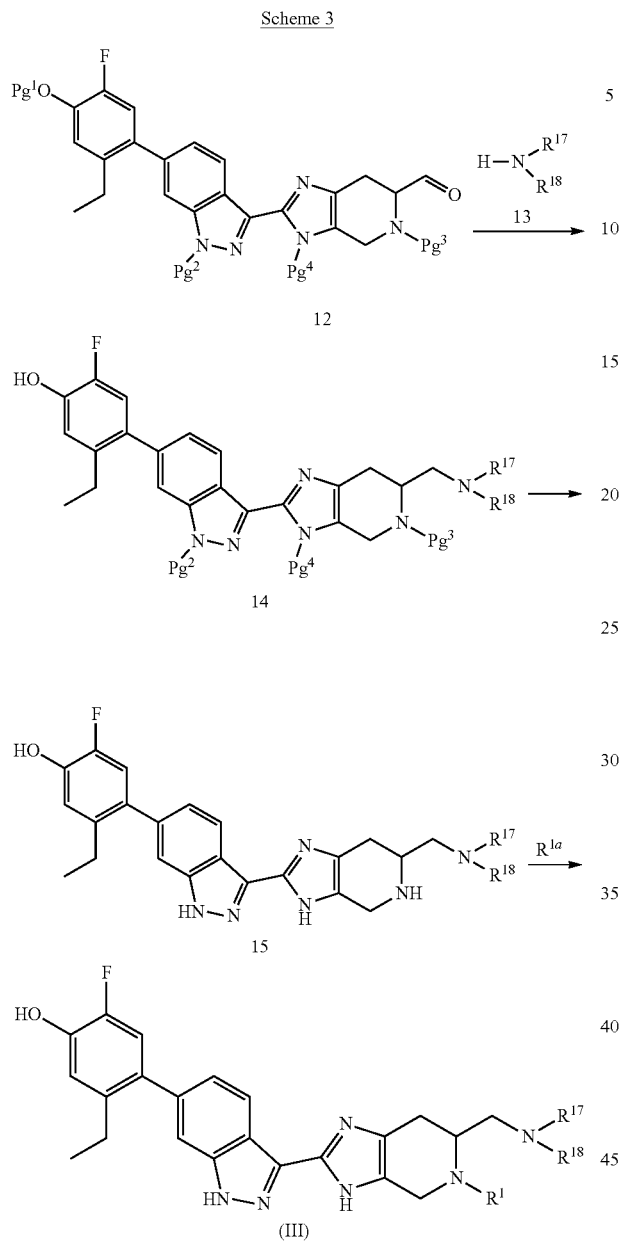

As shown in Scheme 3, the substituent —CH$_2$NR$^{17}$R$^{18}$ is added to a protected intermediate 12 to form intermediate 14, which is fully deprotected, for example by reaction with boron tribromide, to form intermediate 15. In a final step, the substituent R$^1$ is added by reductive alkylation as described in Scheme 2.

Aldehyde intermediate 12 is also useful for the preparation of final compounds of the invention in which X is defined as —CH$_2$OH. Compound 12 may be contacted with a reducing agent such as sodium borohydride to provide a protected intermediate analogous to compound 14 having —CH$_2$OH in place of —CH$_2$NR$^{17}$R$^{18}$, which may be fully deprotected and then reacted with a reagent R$^{1a}$ as in Scheme 3 to provide compounds in which X is —CH$_2$OH.

The aldehyde intermediate 12 may be prepared utilizing the Weinreb-Nahm reaction as shown in Scheme 4.

Scheme 4

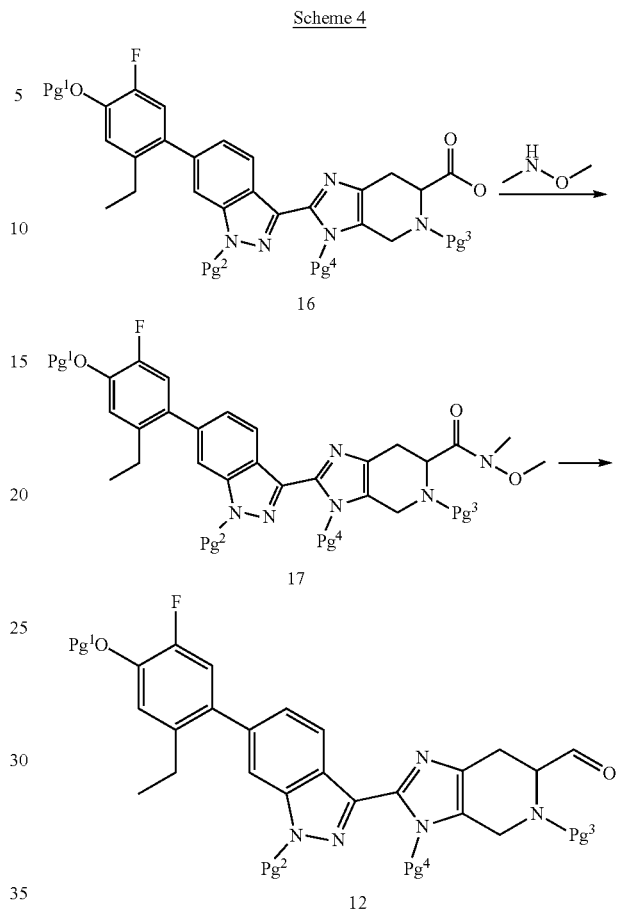

Amide intermediate 17, which is prepared by reaction of compound 16 with dimethylhydroxylamine, is selectively reduced to the aldehyde 12 by contact with lithium aluminum hydride. The reaction is typically conducted at low temperature, for example between about −60° C. and −80° C. for between about 1 and about 3 hours or until the reaction is substantially complete.

Accordingly, in a method aspect, the invention provides a process of preparing a compound of formula (II) or a pharmaceutically acceptable salt thereof, the process comprising reacting a compound of formula 1 with a compound of formula 2, as illustrated in Scheme 1 to provide a compound of formula (II) or a pharmaceutically acceptable salt thereof.

In a further method aspect, the invention provides a process of preparing a compound of formula 1, the process comprising reacting a compound of formula 8 with R$^{1a}$ in the presence of a reducing agent, wherein R$^{1a}$ is an aldehyde or ketone defined such that upon reductive alkylation the substitutent R$^1$, wherein R$^1$ is C$_{1-3}$alkyl, is attached to the compound of formula 8 to provide the compound of formula 1.

In an additional method aspect, the invention provides a process of preparing a compound of formula 8 the process comprising deprotecting a compound of formula 7.

In yet another aspect, the invention provides a compound of formula 1 and compounds of formula 7 and 8, useful in preparing a compound of formula 1.

Pharmaceutical Compositions

The compounds of the invention and pharmaceutically-acceptable salts thereof are typically used in the form of a pharmaceutical composition or formulation. Such pharmaceutical compositions may advantageously be administered to a patient by inhalation. In addition, pharmaceutical compositions may be administered by any acceptable route of administration including, but not limited to, oral, rectal, nasal, topical (including transdermal) and parenteral modes of administration.

Accordingly, in one of its compositions aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formula (II) and pharmaceutically-acceptable salts thereof The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a compound of the invention in micronized form. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In another particular embodiment, the pharmaceutical composition is administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the invention; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another particular aspect, the pharmaceutical composition is administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 µg/mL to about 20 mg/mL of a compound of the invention and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat Softmist Inhalaler (Boehringer Ingelheim); the AERx Pulmonary Delivery System (Aradigm Corp.); the PARI LC Plus Reusable Nebulizer (Pari GmbH); and the like.

In yet another aspect, the pharmaceutical compositions of the invention may alternatively be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form, the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the pharmaceutical compositions of the invention.

Alternative formulations may also include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present invention.

Dry Powder Composition

A micronized compound of formula (I) (1 g) is blended with milled lactose (25 g). This blended mixture is then loaded into individual blisters of a peelable blister pack in an amount sufficient to provide between about 0.1 mg to about 4 mg of the compound of formula I per dose. The contents of the blisters are administered using a dry powder inhaler.

Dry Powder Composition

A micronized compound of formula (I) (1 g) is blended with milled lactose (20 g) to form a bulk composition having a weight ratio of compound to milled lactose of 1:20.

The blended composition is packed into a dry powder inhalation device capable of delivering between about 0.1 mg to about 4 mg of the compound of formula I per dose.

Metered-Dose Inhaler Composition A micronized compound of formula (I) (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 0.1 mg to about 4 mg of the compound of formula I per dose when administered by the metered dose inhaler.

Nebulizer Composition

A compound of formula (I) (25 mg) is dissolved in a solution containing 1.5-2.5 equivalents of hydrochloric acid, followed by addition of sodium hydroxide to adjust the pH to 3.5 to 5.5 and 3% by weight of glycerol. The solution is stirred well until all the components are dissolved. The solution is administered using a nebulizer device that provides about 0.1 mg to about 4 mg of the compound of formula I per dose.

Utility

The JAK inhibitors of the invention have been designed for the treatment of inflammatory and fibrotic disease of the respiratory tract. In particular, the compounds have been designed to enable delivery of a potent anti-cytokine agent directly to the site of action of respiratory disease in the lung while limiting systemic exposure.

The compounds of the invention have been shown to be potent inhibitors of the JAK family of enzymes: JAK1, JAK2, JAK3, and TYK2. In addition, the compounds have demonstrated potent inhibition of pro-inflammatory and pro-fibrotic cytokines without exhibiting cytotoxicity in cellular assays. It has been recognized that the broad anti-inflammatory effect of JAK inhibitors could suppress normal immune cell function, potentially leading to increased risk of infection. The present compounds have therefore been optimized to limit absorption from the lung into the plasma, thus minimizing the risk of immunosuppression.

As described in the experimental section below, the absorption and distribution of typical compounds has been profiled in preclinical assays. Selected compounds tested in mice showed, at the same time, high concentration in lung tissue and low absorption into plasma. Compounds tested in mouse exhibited exposure in lung from one to two orders of magnitude greater than exposure in plasma. The compounds also exhibited significant retention in the mouse lung as evidenced by a lung half-life greater than about 5 hours. Importantly, the concentration of test compound in the mouse lung has been shown to correlate with a predicted pharmacodynamic effect of JAK enzyme inhibition. Compounds of the invention have been shown to inhibit an effect of the pro-inflammatory cytokine IL-13 in mouse lung tissue. Specifically, the compounds have demonstrated dose and concentration dependent inhibition of IL-13-induced phosphorylation of STAT6 in lung tissue which provides evidence of local lung JAK target engagement in vivo. This effect has been observed when the pro-inflammatory cytokine IL-13 is administered 4 hours after administration of the test compound, providing further evidence of significant retention in the lung.

Tested compounds have been demonstrated to exhibit both potent inhibitory activity at the cellular level and significant retention in lung tissue. Extensive investigation by the present inventors has determined that while it is possible to identify compounds that are potent at the cellular level or compounds that show significant retention in the lung, it is far more difficult to discover compounds that exhibit both desirable characteristics at the same time.

The anti-inflammatory activity of JAK inhibitors has been robustly demonstrated in preclinical models of asthma (Malaviya et al., *Int Immunopharmacol*, 2010, 10, 829-836; Matsunaga et al., *Biochem and Biophys Res Commun*, 2011, 404, 261-267; Kudlacz et al., *Eur J Pharmacol*, 2008, 582, 154-161.) Accordingly, the compounds of the invention are expected to be useful for the treatment of inflammatory respiratory disorders, in particular, asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, and sarcoidosis. The present compounds, therefore, are also expected to be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, and sarcoidosis.

The compounds of the disclosure have demonstrated inhibition of human T cell activation, inhibition of cytokines associated with inflammation, and activity on human eosinophils and in rodent lung eosinophilia models. Therefore, the compounds of the disclosure are likely to be useful for the treatment of certain specific respiratory diseases.

Eosinophilic airway inflammation is a characteristic feature of diseases collectively termed eosinophilic lung diseases (Cottin et al., *Clin. Chest. Med.*, 2016, 37(3), 535-56). Eosinophilic diseases have been associated with IL-4, IL-13 and IL-5 signaling. Eosinophilic lung diseases include infections (especially helminthic infections), drug-induced pneumonitis (induced for example by therapeutic drugs such as antibiotics, phenytoin, or 1-tryptophan), fungal-induced pneumonitis (e.g. allergic bronchopulmonary aspergillosis), hypersensitivity pneumonitis and eosinophilic granulomatosis with polyangiitis (formerly known as Churg-Strauss syndrome). Eosinophilic lung diseases of unknown etiology include idiopathic acute eosinophilic pneumoni, idiopathic chronic eosinophilic pneumonia, hypereosinophilic syndrome, and Löffler syndrome. The compounds of the disclosure have been shown to significantly reduce lung eosinophilia in the rodent airway model and to potently inhibit IL-13, IL-4, and IL-2 signaling in cellular assays. In addition, the compound of example 1 has been demonstrated to potently inhibit IL-5 mediated human eosinophil survival.

A polymorphism in the IL-6 gene has been associated with elevated IL-6 levels and an increased risk of developing pulmonary arterial hypertension (PAH) (Fang et al., *J Am Soc Hypertens.*, 2017, 11(3), 171-177). Corroborating the role of IL-6 in PAH, inhibition of the IL-6 receptor chain gp130 ameliorated the disease in a rat model of PAH (Huang et al., *Can J Cardiol.*, 2016, 32(11), 1356.e1-1356.e10). The compounds of examples 1 and 3 have been shown to inhibit IL-6 signaling.

Cytokines such as IFNγ, IL-12 and IL-6 have been implicated in a range of non-allergic lung diseases such as sarcoidosis, and lymphangioleiomyomatosis (El-Hashemite et al., *Am. J. Respir. Cell Mol. Biol.*, 2005, 33, 227-230, and El-Hashemite et al., *Cancer Res.*, 2004, 64, 3436-3443). The compounds of examples 1 and 3 have also been shown to inhibit IL-6 signaling.

Bronchiectasis and infiltrative pulmonary diseases are diseases associated with chronic neutrophilic inflammation. The compounds of examples 1 and 3 have been shown to inhibit cytokines that are associated with neutrophilic inflammation (e.g. IL-6).

Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipients T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., *Curr Transplant Rep.*, 2016, 3(3), 185-191). CLAD is poorly responsive to treatment and therefore, there remains a need for effective compounds capable of preventing or treating this condition. Several JAK-dependent cytokines such as IFNγ and IL-5 are up-regulated in CLAD and lung transplant rejection (Berastegui et al, *Clin Transplant.* 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, *PLOS One*, 2017, 12 (7), e0180281). Systemic JAK inhibition has been shown to be effective in kidney transplant rejection (Vicenti et al., *American Journal of Transplantation*, 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, *Leukemia,* 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD. The compounds of the disclosure have the characteristics required to meet this need. More recently, immune-checkpoint inhibitor induced pneumonitis, another T cell mediated lung disease emerged with the increased use of immune-checkpoint inhibitors. In cancer patients treated with these T cell stimulating agents, fatal pneumonitis can develop. Certain compounds of the disclosure have been shown to inhibit the anti-CD3 and IL-2 induced release of IFNγ from activated human peripheral blood-isolated T cells and thus has the potential to present a novel treatment for these underserved serious respiratory diseases.

In one aspect, therefore, the invention provides a method of treating a respiratory disease in a mammal (e.g., a human), the method comprising administering to the mammal a therapeutically-effective amount of a compound of the invention or of a pharmaceutical composition comprising a pharmaceutically-acceptable carrier and a compound of the invention.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, or sarcoidosis. In another aspect, the respiratory disease is asthma or chronic obstructive pulmonary disease.

In one aspect, the respiratory disease is a lung infection, an eosinophilic disease, a helminthic infection, pulmonary arterial hypertension, sarcoidosis, lymphangioleiomyomatosis, bronchiectasis, an infiltrative pulmonary disease, drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, acute and chronic lung transplant rejections (including PGD, OP, LB, AR and CLAD, BO, restrictive CLAD and neutrophilic allograft dysfunction), lung graft-versus-host disease bronchiolitis obliterans organizing pneumonia, pulmonary arterial hypertension, bronchiectasis, or immune-checkpoint-inhibitor induced pneumonitis.

The invention further provides a method of treating asthma in a mammal, the method comprising administering to the mammal a therapeutically-effective amount of a compound of the invention or of a pharmaceutical composition comprising a pharmaceutically-acceptable carrier and a compound of the invention.

When used to treat asthma, the compounds of the invention will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

The invention further provides a method of treating a respiratory disease (including but not limited to the disease described herein) in a mammal, the method comprising administering to the mammal a therapeutically-effective amount of a compound of the invention or of a pharmaceutical composition comprising a pharmaceutically-acceptable carrier and a compound of the invention.

When used to treat a respiratory disease (including but not limited to the disease described herein), the compounds of the invention will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

As JAK inhibitors, the compounds of the disclosure may also be useful for a variety of other diseases. The compounds of the disclosure may be useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology,* 1996, 16, 144-150), Crohn's disease (Woywodt et al., *Eur J Gastroenterology Hepatology,* 1999, 11, 267-276), collagenous colitis (Kumawat et al., *Mol Immunology,* 2013, 55, 355-364), lymphocytic colitis (Kumawat et al., 2013), eosinophilic esophagitis (Weinbrand-Goichberg et al., *Immunol Res,* 2013, 56, 249-260), graft versus host disease-related colitis (Coghill et al., *Blood,* 2001, 117, 3268-3276), infectious colitis (Stallmach et al., *Int J Colorectal Dis,* 2004, 19, 308-315), Behcet's disease (Zhou et al., *Autoimmun Rev,* 2012, 11, 699-704), celiac disease (de Nitto et al., *World J Gastroenterol,* 2009, 15, 4609-4614), immune checkpoint inhibitor induced colitis (e.g., CTLA-4 inhibitor-induced colitis; (Yano et al., *J Translation Med,* 2014, 12, 191), PD-1- or PD-L1-inhibitor-induced colitis), and ileitis (Yamamoto et al., *Dig Liver Dis,* 2008, 40, 253-259) are characterized by elevation of certain pro-inflammatory cytokine levels. As many pro-inflammatory cytokines signal via JAK activation, compounds described in this application may be able to alleviate the inflammation and provide symptom relief. In particular, the compounds of the disclosure may be useful for the induction and maintenance of remission of ulcerative colitis, and for the treatment of Crohn's disease, immune checkpoint inhibitor induced colitis, and the gastrointestinal adverse effects in graft versus host disease. In one aspect, therefore, the invention provides a method of treating a gastrointestinal inflammatory disease in a mammal (e.g., a human), the method comprising administering to the mammal a compound of the disclosure or a pharmaceutically acceptable salt thereof or a pharmaceutical composition comprising a pharmaceutically-acceptable carrier and a compound of the disclosure or a pharmaceutically acceptable salt thereof.

Atopic dermatitis and other inflammatory skin diseases have been associated with elevation of proinflammatory cytokines that rely on the JAK-STAT pathway. Therefore, the compounds of the disclosure, or a pharmaceutically acceptable salt thereof, may be beneficial in a number of dermal inflammatory or pruritic conditions that include, but are not limited to atopic dermatitis, alopecia areata, vitiligo, psoriasis, dermatomyositis, cutaneous T cell lymphoma (Netchiporouk et al., *Cell Cycle.* 2014; 13, 3331-3335) and subtypes (Sezary syndrome, mycosis fungoides, pagetoid reticulosis, granulomatous slack skin, lymphomatoid papulosis, *pityriasis* lichenoides chronica, *pityriasis* lichenoides et varioliformis *acuta*, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT,* 2013, 2, e24137), alopecia areata (Xing et al., *Nat Med.* 2014, 20, 1043-1049), vitiligo (Craiglow et al, *JAMA Dermatol.* 2015, 151, 1110-1112), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compounds of the disclosure, or a pharmaceutically acceptable salt thereof, may be able to alleviate associated dermal inflammation or pruritus driven by these cytokines. In particular, compounds of the disclosure, or a pharmaceutically acceptable salt thereof, may be expected to be useful for the treatment of atopic dermatitis and other inflammatory skin diseases. In one aspect, therefore, the invention provides a method of treating an inflammatory skin disease in a mammal (e.g., a human), the method comprising applying a pharmaceutical composition comprising a compound of the disclosure, or a pharmaceutically acceptable salt thereof and a pharmaceutical carrier to the skin of the mammal. In one aspect, the inflammatory skin disease is atopic dermatitis.

Many ocular diseases have been shown to be associated with elevations of proinflammatory cytokines that rely on the JAK-STAT pathway. The compounds of the disclosure, or a pharmaceutically acceptable salt thereof, therefore, may be useful for the treatment of a number of ocular diseases that include, but are not limited to, uveitis, diabetic retinopathy, diabetic macular edema, dry eye disease, age-related macular degeneration, and atopic keratoconjunctivitis. In particular, uveitis (Horai and Caspi, *J Interferon Cytokine Res,* 2011, 31, 733-744), diabetic retinopathy (Abcouwer, *J Clin Cell Immunol,* 2013, *Suppl* 1, 1-12), diabetic macular edema (Sohn et al., *American Journal of Opthamology,* 2011, 152, 686-694), dry eye disease (Stevenson et al, *Arch Ophthalmol,* 2012, 130, 90-100), and age-related macular degeneration (Knickelbein et al, *Int Ophthalmol Clin,* 2015, 55(3), 63-78) are characterized by elevation of certain pro-inflammatory cytokines that signal via the JAK-STAT pathway. Accordingly, compounds of the disclosure, or a pharmaceutically acceptable salt thereof, may be able to alleviate the associated ocular inflammation and reverse disease progression or provide symptom relief. In one aspect, therefore, the invention provides a method of treating an ocular disease in a mammal, the method comprising administering a pharmaceutical composition comprising a compound of the disclosure or a pharmaceutically-acceptable salt thereof and a pharmaceutical carrier to the eye of the mammal. In one aspect, the ocular disease is uveitis, diabetic retinopathy, diabetic macular edema, dry eye disease, age-related macular degeneration, or atopic keratoconjunctivitis. In one aspect, the method comprises administering the compound of the disclosure, or a pharmaceutically acceptable salt thereof by intravitreal injection. Compounds of the disclosure, or a pharmaceutically acceptable salt thereof, may also be used in combination with one or more compound useful to ocular diseases.

The compounds of the disclosure, or a pharmaceutically acceptable salt thereof, may also be useful to treat other diseases such as other inflammatory diseases, autoimmune diseases or cancers. The compounds of the disclosure, or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

Combination Therapy

Compounds of the disclosure or a pharmaceutically acceptable salt thereof may be used in combination with one or more agents which act by the same mechanism or by different mechanisms to treat a disease. The different agents may be administered sequentially or simultaneously, in separate compositions or in the same composition. Useful classes of agents for combination therapy include, but are not limited to, a beta 2 adrenoceptor agonist, a muscarinic receptor antagonist, a glucocorticoid agonist, a G-protein coupled receptor-44 antagonist, a leukotriene D4 antagonist, a muscarinic M3 receptor antagonist, a histamine H1 receptor antagonist, an immunoglobulin E antagonist, a PDE 4 inhibitor, an IL-4 antagonist, a muscarinic M1 receptor antagonist, a histamine receptor antagonist, an IL-13 antagonist, an IL-5 antagonist, a 5-Lipoxygenase inhibitor, a beta adrenoceptor agonist, a CCR3 chemokine antagonist, a CFTR stimulator, an immunoglobulin modulator, an interleukin 33 ligand inhibitor, a PDE 3 inhibitor, a phosphoinositide-3 kinase delta inhibitor, a thromboxane A2 antagonist, an elastase inhibitor, a Kit tyrosine kinase inhibitor, a leukotriene E4 antagonist, a leukotriene antagonist, a PGD2 antagonist, a TNF alpha ligand inhibitor, a TNF binding agent, a complement cascade inhibitor, an eotaxin ligand inhibitor, a glutathione reductase inhibitor, an histamine H4 receptor antagonist, an IL-6 antagonist, an IL2 gene stimulator, an immunoglobulin gamma Fc receptor IIB modulator, an interferon gamma ligand, an interleukin 13 ligand inhibitor, an interleukin 17 ligand inhibitor, a L-Selectin antagonist, a leukocyte elastase inhibitor, a leukotriene C4 antagonist, a Leukotriene C4 synthase inhibitor, a membrane copper amine oxidase inhibitor, a metalloprotease-12 inhibitor, a metalloprotease-9 inhibitor, a mite allergen modulator, a muscarinic receptor modulator, a nicotinic acetylcholine receptor agonist, a nuclear factor kappa B inhibitor, a p-Selectin antagonist, a PDE 5 inhibitor, a PDGF receptor antagonist, a phosphoinositide-3 kinase gamma inhibitor, a TLR-7 agonist, a TNF antagonist, an Abl tyrosine kinase inhibitor, an acetylcholine receptor antagonist, an acidic mammalian chitinase inhibitor, an ACTH receptor agonist, an actin polymerization modulator, an adenosine A1 receptor antagonist, an adenylate cyclase stimulator, an adrenoceptor antagonist, an adrenocorticotrophic hormone ligand, an alcohol dehydrogenase 5 inhibitor, an alpha 1 antitrypsin stimulator, an alpha 1 proteinase inhibitor, an androgen receptor modulator, an angiotensin converting enzyme 2 stimulator, an ANP agonist, a Bcr protein inhibitor, a beta 1 adrenoceptor antagonist, a beta 2 adrenoceptor antagonist, a beta 2 adrenoceptor modulator, a beta amyloid modulator, a BMP10 gene inhibitor, a BMP15 gene inhibitor, a calcium channel inhibitor, a cathepsin G inhibitor, a CCL26 gene inhibitor, a CCR3 chemokine modulator, a CCR4 chemokine antagonist, a cell adhesion molecule inhibitor, a chaperonin stimulator, a chitinase inhibitor, a collagen I antagonist, a complement C3 inhibitor, a CSF-1 antagonist, a CXCR2 chemokine antagonist, a cytokine receptor common beta chain modulator, a cytotoxic T-lymphocyte protein-4 stimulator, a deoxyribonuclease I stimulator, a deoxyribonuclease stimulator, a dipeptidyl peptidase I inhibitor, a DNA gyrase inhibitor, a DP prostanoid receptor modulator, an E-Selectin antagonist, an EGFR family tyrosine kinase receptor inhibitor, an elastin modulator, an Endothelin ET-A antagonist, an Endothelin ET-B antagonist, an epoxide hydrolase inhibitor, a FGF3 receptor antagonist, a Fyn tyrosine kinase inhibitor, a GATA 3 transcription factor inhibitor, a Glucosylceramidase modulator, a Glutamate receptor modulator, a GM-CSF ligand inhibitor, a Guanylate cyclase stimulator, a H+K+ ATPase inhibitor, an hemoglobin modulator, an Heparin agonist, an Histone deacetylase inhibitor, an Histone deacetylase-2 stimulator, an HMG CoA reductase inhibitor, an I-kappa B kinase beta inhibitor, an ICAM1 gene inhibitor, an IL-17 antagonist, an IL-17 receptor modulator, an IL-23 antagonist, an IL-4 receptor modulator, an Immunoglobulin G modulator, an Immunoglobulin G1 agonist, an Immunoglobulin G1 modulator, an Immunoglobulin epsilon Fc receptor IA antagonist, an Immunoglobulin gamma Fc receptor IIB antagonist, an Immunoglobulin kappa modulator, an Insulin sensitizer, an Interferon beta ligand, an Interleukin 1 like receptor antagonist, an Interleukin 18 ligand inhibitor, an Interleukin receptor 17A antagonist, an Interleukin-1 beta ligand inhibitor, an Interleukin-5 ligand inhibitor, an Interleukin-6 ligand inhibitor, a KCNA voltage-gated potassium channel-3 inhibitor, a Kit ligand inhibitor, a Laminin-5 agonist, a Leukotriene CysLT1 receptor antagonist, a Leukotriene CysLT2 receptor antagonist, a LOXL2 gene inhibitor, a Lyn tyrosine kinase inhibitor, a MARCKS protein inhibitor, a MDR associated protein 4 inhibitor, a Metalloprotease-2 modulator, a Metalloprotease-9 modulator, a Mineralocorticoid receptor antagonist, a Muscarinic M2 receptor antagonist, a Muscarinic M4 receptor antagonist, a Muscarinic M5 receptor antagonist, a Natriuretic peptide receptor A agonist, a Natural killer cell receptor modulator, a Nicotinic ACh receptor alpha 7 subunit stimulator, a NK cell receptor modulator, a Nuclear factor kappa B modulator, an opioid growth factor receptor agonist, a P-Glycoprotein inhibitor, a P2X3 purinoceptor antagonist, a p38 MAP kinase inhibitor, a Peptidase 1 modulator, a phospholipase A2 inhibitor, a phospholipase C inhibitor, a plasminogen activator inhibitor 1 inhibitor, a platelet activating factor receptor antagonist, a PPAR gamma agonist, a prostacyclin agonist, a protein tyrosine kinase inhibitor, a SH2 domain inositol phosphatase 1 stimulator, a signal transduction inhibitor, a sodium channel inhibitor, a STAT-3 modulator, a Stem cell antigen-1 inhibitor, a superoxide dismutase modulator, a T cell surface glycoprotein CD28 inhibitor, a T-cell surface glycoprotein CD8 inhibitor, a TGF beta agonist, a TGF beta antagonist, a thromboxane synthetase inhibitor, a thymic stromal lymphoprotein ligand inhibitor, a thymosin agonist, a thymosin beta 4 ligand, a TLR-8 agonist, a TLR-9 agonist, a TLR9 gene stimulator, a Topoisomerase IV inhibitor, a Troponin I fast skeletal muscle stimulator, a Troponin T fast skeletal muscle stimulator, a Type I IL-1 receptor antagonist, a Type II TNF receptor modulator, an ion channel modulator, a uteroglobin stimulator, and a VIP agonist.

Specific agents that may be used in combination with the present JAK inhibitor compounds include, but are not limited to rosiptor acetate, umeclidinium bromide, secukinumab, metenkefalin acetate, tridecactide acetate, fluticasone propionate, alpha-cyclodextrin-stabilized sulforaphane, tezepelumab, mometasone furoate, BI-1467335, dupilumab, aclidinium, formoterol, AZD-1419, HI-1640V, rivipansel, CMP-001, mannitol, ANB-020, omalizumab, tregalizumab, Mitizax, benralizumab, golimumab, roflumilast, imatinib, REGN-3500, masitinib, apremilast, RPL-554, Actimmune, adalimumab, rupatadine, parogrelil, MK-1029, beclometasone dipropionate, formoterol fumarate, mogamulizumab, seratrodast, UCB-4144, nemiralisib, CK-2127107, fevipiprant, danirixin, bosentan, abatacept, EC-18, duvelisib, dociparstat, ciprofloxacin, salbutamol HFA, erdosteine, PrEP-001, nedocromil, CDX-0158, salbutamol, enobosarm, R-TPR-022, lenzilumab, fluticasone furoate, vilanterol trifenatate, fluticasone propionate, salmeterol, PT-007, PRS-060, remestemcel-L, citrulline, RPC-4046, nitric oxide, DS-102, gerilimzumab, Actair, fluticasone furoate, umeclidinium, vilanterol, AG-NPP709, Gamunex, infliximab, Ampion, acumapimod, canakinumab, INS-1007, CYP-001, sirukumab, fluticasone propionate, mepolizumab, pitavastatin, solithromycin, etanercept, ivacaftor, anakinra, MPC-300-IV, glycopyrronium bromide, aclidinium bromide, FP-025, risankizumab, glycopyrronium, formoterol fumarate, Adipocell, YPL-001, tiotropium bromide, glycopyrronium bromide, indacaterol maleate, andecaliximab, olodaterol, esomeprazole, dust mite vaccine, mugwort pollen allergen vaccine, vamorolone, gefapixant, revefenacin, gefitinib, Rejoin, tipelukast, bedoradrine, SCM-CGH, SHP-652, RNS-60, brodalumab, BIO-11006, umeclidinium bromide, vilanterol trifenatate, ipratropium bromide, tralokinumab, PUR-1800, VX-561, VX-371, olopatadine, tulobuterol, formoterol fumarate, triamcinolone acetonide, reslizumab, salmeterol xinafoate, fluticasone propionate, beclometasone dipropionate, formoterol fumarate, tiotropium bromide, ligelizumab, RUTI, bertilimumab, omalizumab, glycopyrronium bromide, SENS-111, beclomethasone dipropionate, CHF-5992, LT-4001, indacaterol, glycopyrronium bromide, mometasone furoate, fexofenadine, glycopyrronium bromide, azithromycin, AZD-7594, formoterol, CHF-6001, batefenterol, OATD-01, olodaterol, CJM-112, rosiglitazone, salmeterol, setipiprant, inhaled interferon beta, AZD-8871, plecanatide, fluticasone, salmeterol, eicosapentaenoic acid monoglycerides, lebrikizumab, RG-6149, QBKPN, Mometasone, indacaterol, AZD-9898, sodium pyruvate, zileuton, CG-201, imidafenacin, CNTO-6785, CLBS-03, mometasone, RGN-137, procaterol, formoterol, CCI-15106, POL-6014, indacaterol, beclomethasone, MV-130, GC-1112, Allergovac depot, MEDI-3506, QBW-251, ZPL-389, udenafil, GSK-3772847, levocetirizine, AXP-1275, ADC-3680, timapiprant, abediterol, AZD-7594, ipratropium bromide, salbutamol sulfate, tadekinig alfa, ACT-774312, dornase alfa, iloprost, batefenterol, fluticasone furoate, alicaforsen, ciclesonide, emeramide, arformoterol, SB-010, Ozagrel, BTT-1023, Dectrekumab, levalbuterol, pranlukast, hyaluronic acid, GSK-2292767, Formoterol, NOV-14, Lucinactant, salbutamol, prednisolone, ebastine, dexamethasone cipecilate, GSK-2586881, BI-443651, GSK-2256294, VR-179, VR-096, hdm-ASIT+, budesonide, GSK-2245035, VTX-1463, Emedastine, dexpramipexole, levalbuterol, N-6022, dexamethasone sodium phosphate, PIN-201104, OPK-0018, TEV-48107, suplatast, BI-1060469, Gemilukast, interferon gamma, dalazatide, bilastine, fluticasone propionate, salmeterol xinafoate, RP-3128, bencycloquidium bromide, reslizumab, PBF-680, CRTH2 antagonist, Pranlukast, salmeterol xinafoate, fluticasone propionate, tiotropium bromide monohydrate, masilukast, RG-7990, Doxofylline, abediterol, glycopyrronium bromide, TEV-46017, ASM-024, fluticasone propionate, glycopyrronium bromide, salmeterol xinafoate, salbutamol, TA-270, Flunisolide, sodium chromoglycate, Epsi-gam, ZPL-521, salbutamol, aviptadil, TRN-157, Zafirlukast, Stempeucel, pemirolast sodium, nadolol, fluticasone propionate+salmeterol xinafoate, RV-1729, salbutamol sulfate, carbon dioxide+perfluorooctyl bromide, APL-1, dectrekumab+VAK-694, lysine acetylsalicylate, zileuton, TR-4, human allogenic adipose-derived mesenchymal progenitor cell therapy, MEDI-9314, PL-3994, HMP-301, TD-5471, NKTT-120, pemirolast, beclomethasone dipropionate, trantinterol, monosodium alpha luminol, IMD-1041, AM-211, TBS-5, ARRY-502, seratrodast, recombinant midismase, ASM-8, deflazacort, bambuterol, RBx-10017609, ipratropium+fenoterol, fluticasone+formoterol, epinastine, WIN-901X, VALERGEN-DS, OligoG-COPD-5/20, tulobuterol, oxis Turbuhaler, DSP-3025, ASM-024, mizolastine, budesonide+salmeterol, LH-011, AXP-E, histamine human immunoglobulin, YHD-001, theophylline, ambroxol+erdosteine, ramatroban, montelukast, pranlukast, AG-1321001, tulobuterol, ipratropium+salbutamol, tranilast, methylprednisolone suleptanate, colforsin daropate, repirinast, and doxofylline.

Also provided, herein, is a pharmaceutical composition comprising a compound of the disclosure or a pharmaceutically acceptable salt thereof and one or more other therapeutic agents. The therapeutic agent may be selected from the class of agents specified above and from the list of specific agent described above. In some embodiments, the pharmaceutical composition is suitable for delivery to the lungs. In some embodiments, the pharmaceutical composition is suitable for inhaled or nebulized administration. In some embodiments, the pharmaceutical composition is a dry powder or a liquid composition.

Further, in a method aspect, the invention provides a method of treating a disease or disorder in a mammal comprising administering to the mammal a compound of the disclosure or a pharmaceutically acceptable salt thereof and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

Compounds of the invention have been demonstrated to be potent inhibitors of the JAK1, JAK2, JAK3, and TYK2 enzymes in enzyme binding assays, to have potent functional activity without cytotoxicity in cellular assays, and to exert the pharmacodynamic effects of JAK inhibition in preclinical models, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.
ACN=acetonitrile
DCM=dichloromethane
DIPEA=N,N-diisopropylethylamine
DMF=N,N-dimethylformamide
EtOAc=ethyl acetate
h=hour(s)
HATU=N,N,N'N'-tetramethyl-O-(7-azabenzotriazol-1-yl) uronium hexafluorophosphate
IPA=isopropyl alcohol
IPAc=isopropylacetate
MeOH=methanol
min=minute(s)
Pd(PPh$_3$)$_4$=tetrakis(triphenylphosphine)palladium(0)
RT=room temperature
TFA=trifluoroacetic acid
THF=tetrahydrofuran
bis(pinacolato)diboron=4,4,5,5,4',4',5',5'-octamethyl-[2,2']bi[[1,3,2]dioxaborolanyl]

Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Preparative HPLC Conditions
Column: C18, 5 μm. 21.2×150 mm or C18, 5 μm 21×250 or C14, 5 μm 21×150 mm
Column temperature: Room Temperature
Flow rate: 20.0 mL/min
Mobile Phases: A=Water+0.05% TFA
B=ACN+0.05% TFA,
Injection volume: (100-1500 μL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100μl injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

In the following synthetic examples, compounds numbers less than 20 refer to intermediates presented in Schemes 1 to 4 where the prime designates a compound with a particular choice of protecting group.

Preparation 1: 2-(4-(Benzyloxy)-2-ethyl-5-fluorophenyl)-4,4,5,5-tetramethyl-1,3,2-dioxaborolane (9)

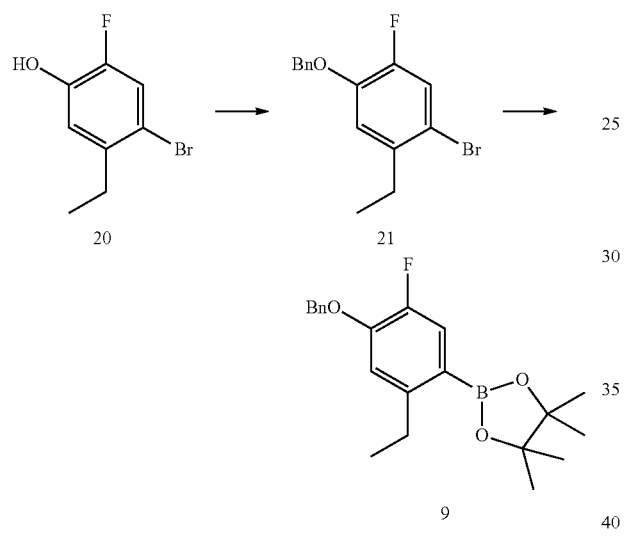

(a) 1-(Benzyloxy)-4-bromo-5-ethyl-2-fluorobenzene (21)

To a solution of 4-bromo-5-ethyl-2-fluorophenol (20) (20 g, 910.32 mmol) in ACN (250 mL) was added K$_2$CO$_3$ (31.55 g, 228.3 mmol) followed by benzyl bromide (13.10 mL, 109.58 mmol) drop wise. The resulting reaction mixture was stirred at 80° C. for 2 h. The aqueous layer was extracted with EtOAc (three times), combined and washed with brine. The organic layer was dried over Na$_2$SO$_4$ and evaporated under reduced pressure to afford the title intermediate as a pale yellow oily liquid (25 g, 89% yield). $^1$H NMR (400 MHz, chloroform-d) δ 7.48-7.30 (m, 5H), 7.27 (d, J=10.5 Hz, 1H), 6.87 (d, J=8.7 Hz, 1H), 5.12 (s, 2H), 2.66 (q, J=7.5 Hz, 2H), 1.16 (t, J=7.5 Hz, 3H).

(b) 2-(4-(Benzyloxy)-2-ethyl-5-fluorophenyl)-4,4,5, 5-tetramethyl-1,3,2-dioxaborolane (9)

To a solution of the product of the previous step (21) (12.5 g, 40.45 mmol) in dioxane (100 mL) was added bis(pinacolato)diboron (15.40 g, 60.67 mmol) and KOAc (11.9 g, 121.35 mmol). The reaction mixture was purged with nitrogen for 15 min followed by addition of [1,1'-bis(diphenylphosphino)ferrocene]dichloropalladium(II), complex with dichloromethane (1.65 g, 2.023 mmol). The resulting reaction mixture was stirred and heated at 110° C. for 3 h, filtered through Celite and the residue washed with EtOAc. The filtrate was diluted with excess EtOAc (200 mL) and washed with water (100 mL) followed by brine (100 mL), dried over sodium sulfate and concentrated in vacuo to get crude product which was purified by column chromatography over (100-200) silica gel, eluted with 3-5% EtOAc: hexane to afford the desired product as an off-white solid (9.50 g, 66% yield). $^1$H NMR (400 MHz, chloroform-d) δ 7.54-7.27 (m, 6H), 6.81 (d, J=7.9 Hz, 1H), 5.16 (s, 2H), 2.84 (q, J=7.5 Hz, 2H), 1.32 (s, 12H), 1.14 (t, J=7.5 Hz, 3H).

Preparation 2: 6-(4-(benzyloxy)-2-ethyl-5-fluorophenyl)-1-(tetrahydro-2H-pyran-2-yl)-3-(trimethylstannyl)-1H-indazole (3')

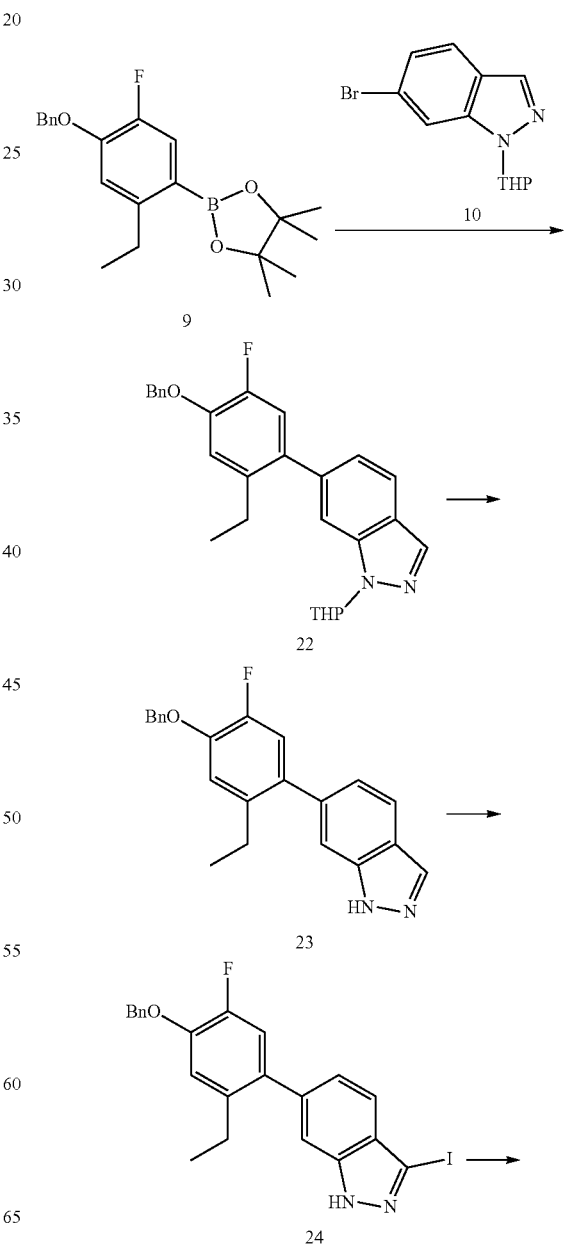

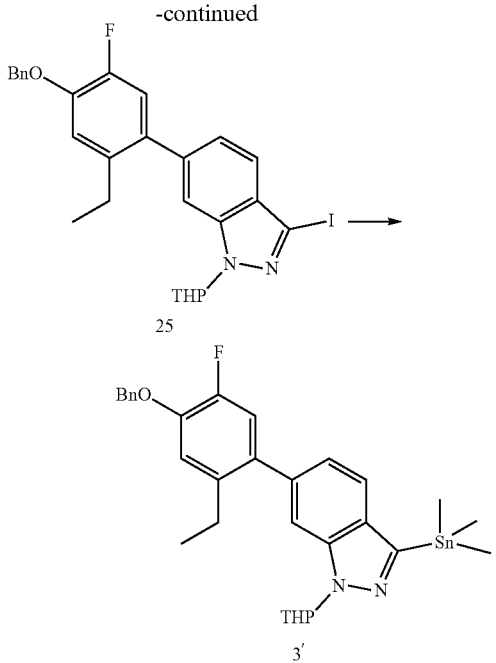

(a) 6-(4-(Benzyloxy)-2-ethyl-5-fluorophenyl)-1-(tetrahydro-2H-pyran-2-yl)-1H-indazole (22)

To a solution of 6-bromo-1-(tetrahydro-2H-pyran-2-yl)-1H-indazole (10) (50 g, 178.57 mmol) and 2-(4-(benzyloxy)-2-ethyl-5-fluorophenyl)-4,4,5,5-tetramethyl-1,3,2-dioxaborolane (9) (76.3 g, 214.29 mmol) in DMF:H$_2$O (480:120 mL) was added K$_3$PO$_4$ (94.64 g, 446.86 mmol). The reaction mixture was degassed with nitrogen for 15 min, then Pd(PPh$_3$)$_2$Cl$_2$ catalyst (6.26 g, 8.93 mmol) was added and the mixture was again degassed with nitrogen for 5 min stirred, and heated at 100-110° C. for 5 h. The reaction mixture was filtered through Celite and the residue was washed with EtOAc. The filtrate was diluted with EtOAc, washed with cold water and brine, dried over sodium sulfate and concentrated in vacuo to provide crude product which was purified by flash column chromatography to afford the title intermediate as a white solid (65 g, 86% yield). (m/z): [M+H]$^+$ calcd for C$_{27}$H$_{27}$FN$_2$O$_2$ 431.21 found 431.46. $^1$H NMR (400 MHz, chloroform-d) δ 8.06-7.98 (m, 2H), 7.70 (d, J=8.2 Hz, 1H), 7.51-7.32 (m, 5H), 7.08 (dd, J=809.6, 8.3 Hz, 1H), 7.03 (d, J=11.9 Hz, 1H), 6.95 (d, J=8.5 Hz, 1H), 5.76-5.64 (m, 1H), 5.20 (s, 2H), 4.04 (d, J=10.1 Hz, 1H), 3.72 (t, J=9.7 Hz, 1H), 2.52 (q, J=7.5 Hz, 2H), 2.22-2.02 (m, 3H), 1.80-1.71 (m, 3H), 1.06 (t, J=7.5 Hz, 3H).

(b) 6-(4-(Benzyloxy)-2-ethyl-5-fluorophenyl)-1H-indazole (23)

To a solution of the product of the previous step (22) (65 g, 151.16 mmol) in methanol (700 mL) was added conc. HCl (120 mL) and the resulting solution was heated at 60-65° C. for 3 h, cooled to RT, and concentrated in vacuo. The residue was dissolved in EtOAc and washed with saturated NaHCO$_3$ aqueous solution and water. The organic layer was dried over anhydrous Na$_2$SO$_4$ and concentrated in vacuo to afford the title intermediate as a white solid (52 g, 99% (crude)). $^1$H NMR (400 MHz, chloroform-d) δ 8.13 (s, 1H), 7.77 (d, J=8.3 Hz, 1H), 7.59-7.30 (m, 6H), 7.10 (d, J=8.3 Hz, 1H), 7.01 (d, J=11.8 Hz, 1H), 6.96 (d, J=8.4 Hz, 1H), 5.21 (s, 2H), 2.53 (q, J=7.5 Hz, 2H), 1.05 (t, J=7.5 Hz, 3H).

(c) 6-(4-(Benzyloxy)-2-ethyl-5-fluorophenyl)-3-iodo-1H-indazole (24)

To a solution of 6-(4-(benzyloxy)-2-ethyl-5-fluorophenyl)-1H-indazole (23) (56 g, 161.18 mmol) in DMF (400 mL) was added KOH (36.2 g, 647.39 mmol) and the mixture was stirred for 5 min. A solution of iodine (82.2 g, 323.69 mmol) in DMF (100 mL) was added slowly at 0° C. and stirred at RT for 30 min, diluted with water (3×150 mL) and extracted with EtOAc (3×200 mL). The organic layer was washed with saturated sodium metabisulfite aqueous solution (3×200 mL) and water (400 mL), dried over anhydrous Na$_2$SO$_4$ and concentrated under reduced pressure to get crude product which was purified by flash column chromatography to afford the title intermediate as a brownish semi-solid (64 g, 84% yield). $^1$H NMR (400 MHz, chloroform-d) δ 10.49 (s, 1H), 7.57-7.32 (m, 7H), 7.16 (d, J=8.3 Hz, 1H), 7.04-6.91 (m, 2H), 5.20 (s, 2H), 2.51 (q, J=7.4 Hz, 2H), 1.04 (t, J=7.5 Hz, 3H).

(d) 6-(4-(Benzyloxy)-2-ethyl-5-fluorophenyl)-3-iodo-1-(tetrahydro-2H-pyran-2-yl)-1H-indazole (25)

To an ice-cold solution of the product of the previous step (24) (60 g, 127.12 mmol) in DCM (700 mL) was added p-toluensulfonic acid (4.84 g, 25.423 mmol) followed by 3,4-dihydro-2H-pyran (17.43 mL, 190.68 mmol) drop wise. The reaction mixture was stirred at RT overnight, diluted with DCM and washed with saturated NaHCO$_3$ aqueous solution and brine. The organic layer was dried over anhydrous Na$_2$SO$_4$ and concentrated under reduced pressure to provide crude product which was purified by flash chromatography (silica gel) to afford the title intermediate as an off white solid (64 g, 91% yield). (m/z): [M+H]$^+$ calcd for C$_{27}$H$_{26}$FIN$_2$O$_2$ 557.10 found 557.30. $^1$H NMR (400 MHz, chloroform-d) δ 7.56-7.31 (m, 7H), 7.14 (d, J=8.3 Hz, 1H), 7.01 (d, J=11.8 Hz, 1H), 6.95 (d, J=8.5 Hz, 1H), 5.68 (d, J=9.3 Hz, 1H), 5.20 (s, 2H), 4.08-3.99 (m, 1H), 3.77-3.64 (m, 1H), 2.50 (q, J=7.2 Hz, 2H), 2.23-1.97 (m, 3H), 1.81-1.68 (m, 3H), 1.06 (t, J=7.4 Hz, 3H).

(e) 6-(4-(benzyloxy)-2-ethyl-5-fluorophenyl)-1-(tetrahydro-2H-pyran-2-yl)-3-(trimethylstannyl)-1H-indazole (3')

To a solution of 6-(4-(benzyloxy)-2-ethyl-5-fluorophenyl)-3-iodo-1-(tetrahydro-2H-pyran-2-yl)-1H-indazole (25) (20 g, 35.97 mmol) in toluene (150 mL) was added hexamethylditin (9.2 mL, 43.17 mmol). The reaction mixture was degassed with nitrogen for 20 min followed by addition of tetrakis (2.0 g, 1.80 mmol) and then stirred at 100° C. for 2 h, cooled to RT, filtered through Celite and residue washed with EtOAc The filtrate was concentrated and purified by column chromatography (over neutral alumina), eluted with 2-5%. EtOAc:hexane to afford the title compound (17.50 g, 82% yield). (m/z): [M+H]$^+$ calcd for C$_{27}$H$_{26}$FIN$_2$O$_2$ 557.10 found 557.30. (m/z): [M+H]$^+$ calcd for C$_{30}$H$_{35}$FN$_2$O$_2$Sn 595.17, 593.17 found 595.49, 593.55. $^1$H NMR (400 MHz, chloroform-d) δ 7.68 (d, J=8.0 Hz, 1H), 7.57-7.29 (m, 6H), 7.13-7.00 (m, 2H), 6.96 (d, J=8.4 Hz, 1H), 5.81-5.68 (m, 1H), 5.21 (s, 2H), 4.13-4.00 (m, 1H), 3.81-3.66 (m, 1H), 2.54 (q, J=7.3 Hz, 2H), 2.23-2.00 (m, 2H), 1.87-1.59 (m, 4H), 1.08 (t, J=7.5 Hz, 3H), 0.47 (s, 9H).

Preparation 3: 5-(tert-butyl) 6-methyl (S)-2-iodo-3-((2-trimethylsilyl)ethoxy) methyl)-3,4,6,7-tetra-hydro-5H-imidazo[4,5-c]pyridine-5,6-dicarboxylate (4')

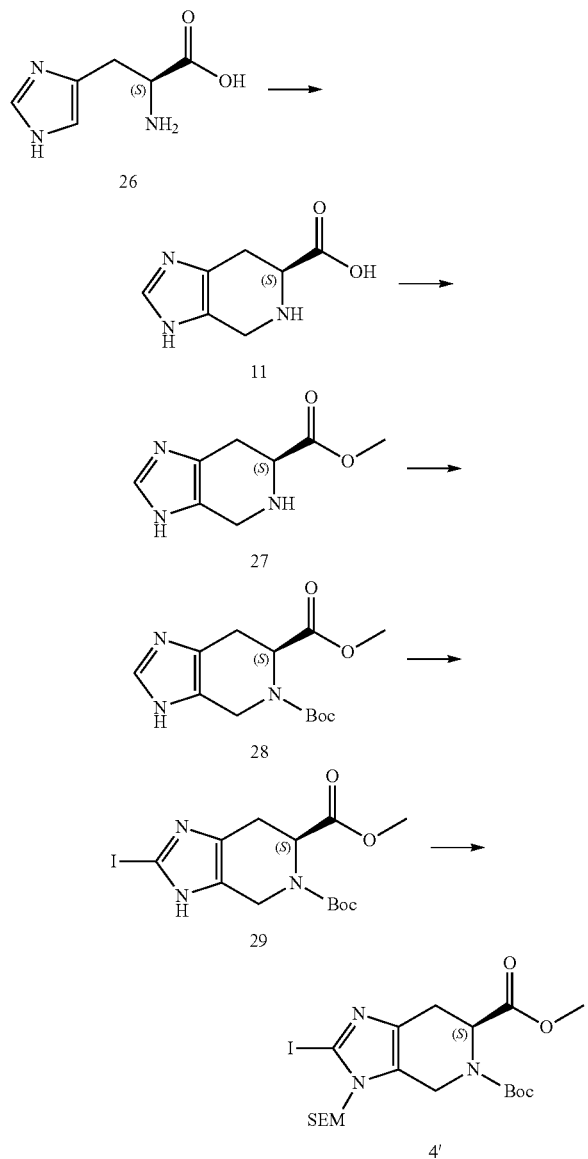

(a) (S)-4,5,6,7-Tetrahydro-3H-imidazo[4,5-c]pyridine-6-carboxylic acid (11)

To a stirred suspension of L-histidine (26) (50 g, 322.24 mmol) in water (420 mL) was added conc. HCl (29 mL) drop wise at 0° C. followed by formaldehyde (55 mL, 676.72 mmol) in one portion at 0° C. The resulting reaction mixture was stirred for 30 min and then heated at 75° C. for 6 h and concentrated. The resulting crude was stirred for 2 h with diethyl ether, filtered and washed with IPA:THF (100:300 mL) to provide the HCl salt of the title intermediate as an off white solid (75 g 99% yield (crude)). (m/z): [M+H]$^+$ calcd for $C_7H_9N_3O_2$ 168.07 found 168.17.

(b) Methyl (S)-4,5,6,7-tetrahydro-3H-imidazo[4,5-c]pyridine-6-carboxylate (27)

To a stirred solution of the product of the previous step (11) (75.0 g, 312.5 mmol) in methanol (1500 mL) was added SOCl$_2$ (45.6 mL, 625 mmol) dropwise at 0° C. and stirred at RT for 16 h, then heated up to reflux (70° C.) for 1 h. The solvent was removed by distillation and the crude product was triturated with methanol followed by diethyl ether to provide the crude HCl salt of the title intermediate as an off white solid (80 g crude). $^1$H NMR (400 MHz, DMSO-d$_6$) δ 9.05 (s, 1H), 4.71 (dd, J=9.4, 5.2 Hz, 1H), 4.36 (d, J=15.5 Hz, 1H), 4.30 (d, J=15.6 Hz, 1H), 3.82 (s, 3H), 3.44-3.21 (m, 2H).

(c) 5-(tert-Butyl) 6-methyl (S)-3,4,6,7-tetrahydro-5H-imidazo[4,5-c]pyridine-5,6-dicarboxylate (28)

To a stirred solution of the product of the previous step (27) (80.0 g, 314.96 mmol) in methanol (1000 mL) was added DIPEA (282 mL, 1574 mmol) followed by di-tert-butyl dicarbonate (172 mL, 787.48 mmol) at 0° C. The reaction mixture was stirred at RT for 16 h and then liquid NH$_3$ (150 mL, 25% in water) was added and the reaction mixture was stirred again for 16 h at RT, methanol was removed by distillation and the residue was extracted in DCM (3×200 mL). Combined organic extracts were dried over anhydrous Na$_2$SO$_4$, concentrated and purified by flash chromatography (100-200 mesh silica gel), eluted with 5% MeOH:DCM to afford the title intermediate (41 g, 46%. yield). (m/z): [M+H]$^+$ calcd for $C_{13}H_{19}N_3O_4$ 282.14 found 282.21. $^1$H NMR (400 MHz, DMSO-d$_6$) δ 11.85 (s, 1H), 7.50 (s, 1H), 5.18 (dd, J=49.3, 5.1 Hz, 1H), 4.51 (t, J=14.2 Hz, 1H), 4.09 (dd, J=43.9, 16.1 Hz, 1H), 3.59 (s, 3H), 3.08 (d, J=15.5 Hz, 1H), 2.94 (d, J=15.1 Hz, 1H), 1.45 (s, 9H).

(d) 5-(tert-Butyl) 6-methyl (S)-2-iodo-3,4,6,7-tetrahydro-5H-imidazo[4,5-c]pyridine-5,6-dicarboxylate (29)

To a solution of the product of the previous step (29) (41.0 g, 145.9 mmol) in THF (500 mL) was added N-iodosuccinimide (66.0 g, 291.8 mmol) at 0° C. and the resulting solution was stirred at RT for 4 h, diluted with water and extracted with ethyl acetate. The organic portion was washed with 10% sodium thiosulphate solution (3×200 mL). The combined organic layer was dried over anhydrous sodium sulfate, and concentrated to provide the title compound 60 g (crude), which was used in the next step without further purification. (m/z): [M+H]$^+$ calcd for $C_{13}H_{18}IN_3O_4$ 408.03 found 408.31. $^1$H NMR (400 MHz, DMSO-d$_6$) δ 12.48 (s, 1H), 5.34-4.97 (m, 1H), 4.67-4.35 (m, 1H), 4.12-3.95 (m, 1H), 3.60 (s, 3H), 3.14-2.82 (m, 2H), 1.44 (s, 9H).

(e) 5-(tert-Butyl) 6-methyl (S)-2-iodo-3-((2-trimethylsilyl)ethoxy) methyl)-3,4,6,7-tetrahydro-5H-imidazo[4,5-c]pyridine-5,6-dicarboxylate (4')

To a stirred solution of 5-(tert-butyl) 6-methyl (S)-2-iodo-3,4,6,7-tetrahydro-5H-imidazo[4,5-c]pyridine-5,6-dicarboxylate (29) (40 g, 0.098 mol) in DMF (150 mL) was added DIPEA (35.1 mL, 0.19 mol) at 0° C. The reaction mixture was stirred for 10 min then 2-(trimethylsilyl)-ethoxymethyl chloride (19.1 mL, 0.10 mol) was added drop wise at 0° C. The resulting reaction mixture was stirred for 3 h at RT. After 4 h chilled water was added and the reaction mixture was extracted with EtOAc (2×200 mL). The organic layer was dried over anhydrous sodium sulphate, concentrated, and purified by flash column chromatography, eluted with 20-35% EtOAc:hexane, to afford the title product as a pale yellow viscous liquid (27 g). (m/z): [M+H]+ calcd for $C_{19}H_{32}IN_3O_5Si$ 538.12 found 538.42. $^1$H NMR (400 MHz, DMSO-$d_6$) δ 5.33-5.04 (m, 3H), 4.79-4.56 (m, 1H), 4.54-4.14 (m, 1H), 3.60 (s, 3H), 3.47 (t, J=7.8 Hz, 2H), 3.31-3.16 (m, 1H), 2.97 (t, J=18.9 Hz, 1H), 1.44 (s, 9H), 0.92-0.74 (m, 2H), −0.03 (s, 9H).

Preparation 4: (6S)-5-(tert-butoxycarbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic Acid (7')

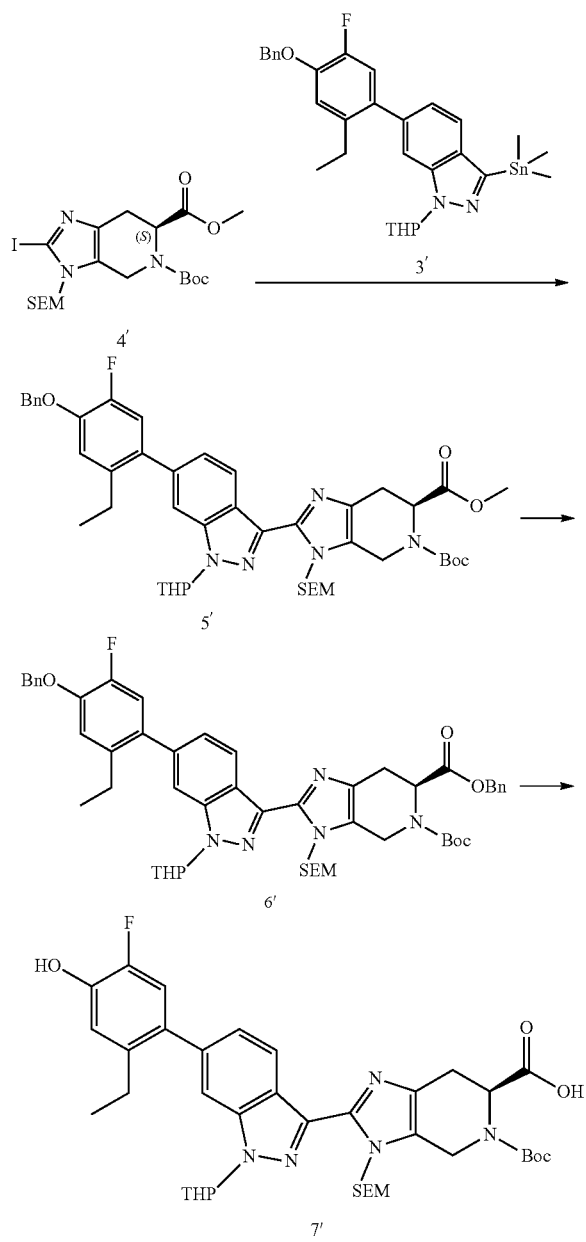

(a) 5-(tert-Butyl) 6-methyl (6S)-2-(6-(4-(benzyloxy)-2-ethyl-5-fluorophenyl)-1-(tetrahydro-2H-pyran-2-yl)-1H-indazol-3-yl)-3-((2-(trimethylsilyl)ethoxy) methyl)-3,4,6,7-tetrahydro-5H-imidazo[4,5-c]pyridine-5,6-dicarboxylate (5')

To a stirred solution of 5-(tert-butyl) 6-methyl (S)-2-iodo-3-((2-trimethylsilyl)ethoxy) methyl)-3,4,6,7-tetrahydro-5H-imidazo[4,5-c]pyridine-5,6-dicarboxylate (4') (17.0 g, 31.65 mmol) in toluene (500 mL) was added 6-(4-(benzyloxy)-2-ethyl-5-fluorophenyl)-1-(tetrahydro-2H-pyran-2-yl)-3-(trimethylstannyl)-1H-indazole (3') (20 g, 34.82 mmol). The reaction mixture was purged with argon for 15 min, Pd(PPh$_3$)$_4$ (3.6 g, 3.16 mmol) and copper iodide (1.20 g, 6.33 mmol) were added and the reaction mixture was stirred at 120° C. for 16 h. The reaction mixture was filtered through Celite, the filtrate was concentrated under reduced pressure and purified by silica gel column chromatography (Redisep 80 g column, eluted with DCM for 10 min and then 15-20% EtOAc in Hexane to afford the title intermediate as a yellow solid (15.10 g, 58% yield). (m/z): [M+H]$^+$ calcd for $C_{46}H_{58}FN_5O_7Si$ 840.41 found 840.54. $^1$H NMR (400 MHz, Chloroform-d) δ 8.43 (s, 1H), 7.54-7.33 (m, 6H), 7.20 (s, 1H), 7.05 (d, J=11.4 Hz, 1H), 6.95 (d, J=8.5 Hz, 1H), 6.09-5.69 (m, 3H), 5.59-5.36 (m, 1H), 5.20 (s, 2H), 4.97-4.80 (m, 1H), 4.12-3.90 (m, 1H), 3.68 (s, 3H), 3.57-3.47 (m, 2H), 3.40 (d, 1H), 3.21-3.05 (m, 1H), 2.74-2.34 (m, 4H), 2.25-2.07 (m, 2H), 1.94-1.65 (m, 4H), 1.54 (s, 9H), 1.12-0.99 (m, 3H), 0.91-0.75 (m, 2H), −0.12 (s, 9H).

(b) 6-Benzyl 5-(tert-butyl) (6S)-2-(6-(4-(benzyloxy)-2-ethyl-5-fluorophenyl)-1-(tetrahydro-2H-pyran-2-yl)-1H-indazol-3-yl)-3-((2-(trimethylsilyl)ethoxy) methyl)-3,4,6,7-tetrahydro-5H-imidazo[4,5-c]pyridine-5,6-dicarboxylate (6')

To a round bottom flask was added the product of the previous step (5') (15.0 g, 17.85 mmol) in toluene (400 mL), benzyl alcohol (46.3 mL) and Ti(OEt)$_4$ (7.15 mL, 35.70 mmol) and the reaction mixture was refluxed vigorously (140° C.) for 48 h, diluted with water and extracted with DCM. The suspension was filtered, filtrate was dried over Na$_2$SO$_4$, concentrated under reduced pressure and purified by silica gel column chromatography (Redisep 80 g column, 0-5% EtOAc in hexanes) for 20 min to remove excess benzyl alcohol, then eluted with 10-15% EtOAc in Hexane) to provide the title intermediate. $^1$H NMR consistent with structure. (m/z): [M+H]$^+$ calcd for $C_{52}H_{62}FN_5O_7Si$ 916.44 found 916.86.

(c) (6S)-5-(tert-butoxycarbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic acid (7')

To a stirred solution of the product of the previous step (6') (21.0 g, 22.92 mmol) in 1:1 IPA:THF (400 mL)) was added Pd(OH)$_2$ (5.0 g). The reaction mixture was stirred at RT for 16 h under a hydrogen balloon, filtered through Celite, concentrated under reduced pressure, and purified by silica gel column chromatography (Redisep 80 g column, eluted with 25-40% EtOAc in Hexane) to provide the title compound (6.1 g, 8.29 mmol) as an off-white solid). (m/z): [M+H]$^+$ calcd for $C_{38}H_{50}FN_5O_7Si$ 736.35 found 736.5. $^1$H NMR consistent with structure. (m/z): [M+H]$^+$ calcd for $C_{38}H_{50}FN_5O_7Si$ 736.35 found 736.5. $^1$H NMR (400 MHz, DMSO-d$_6$) δ 12.94 (s, 1H), 9.86 (s, 1H), 8.34 (t, J=7.6 Hz, 1H), 7.66 (s, 1H), 7.20 (d, J=8.7 Hz, 1H), 7.03 (d, J=11.8 Hz, 1H), 6.93 (d, J=9.1 Hz, 1H), 6.11-5.77 (m, 3H), 5.33-5.06 (m, 1H), 4.87-4.56 (m, 1H), 4.52-4.14 (m, 1H), 3.97-3.69 (m, 2H), 3.53-3.40 (m, 2H), 3.23-3.11 (m, 1H), 3.11-2.93 (m, 1H), 2.47-2.44 (m, 2H), 2.13-1.96 (m, 2H), 1.68 (d, J=70.9 Hz, 4H), 1.48 (s, 9H), 1.02 (t, J=7.5 Hz, 3H), 0.86-0.68 (m, 2H), −0.17 (s, 9H).

Preparation 5: (S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid (8')

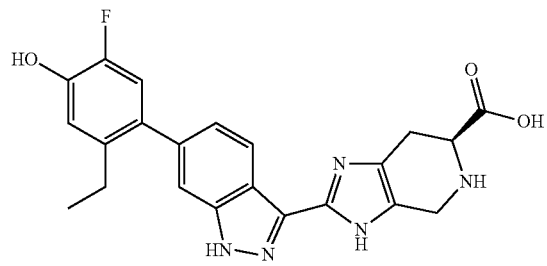

To a stirred solution of (6S)-5-(tert-butoxycarbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic acid (7') (5.7 g, 7.75 mmol) in 5:1 dioxane:water (60 mL) was added conc. HCl (20 mL) drop wise at 0° C. The reaction mixture was warmed and stirred at 90° C. for 16 h and distilled under vacuum to provide the crude residue, which was sequentially triturated with chilled diethyl ether and acetonitrile to provide the HCl salt of the title compound (3.6 g, 95% yield) as a light brown solid. (m/z): [M+H]$^+$ calcd for C$_{22}$H$_{20}$FN$_5$O$_3$ 422.16 found 422.24. $^1$H NMR (400 MHz, D$_2$O/DMSO-d$_6$) δ 8.22 (d, J=8.4 Hz, 1H), 7.49 (s, 1H), 7.19 (d, J=8.1 Hz, 1H), 6.99 (d, J=11.9 Hz, 1H), 6.91 (d, J=9.0 Hz, 1H), 4.56-4.51 (m, 1H), 4.36 (d, J=15.5 Hz, 1H), 4.30 (d, J=15.5 Hz, 1H), 3.35-3.25 (m, 1H), 3.15-3.05 (m, 1H), 2.4-2.55 (m, 2H), 0.97 (t, J=7.5 Hz, 3H).

Preparation 6: (S)-2-(6-(2-ethyl-5-fluoro-4-hydroxyphenyl)-1H-indazol-3-yl)-5-propyl-4,5,6,7-tetrahydro-3H-imidazo[4,5-c]pyridine-6-carboxylic acid

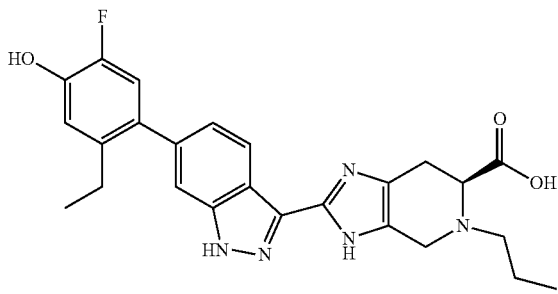 [SMILES: CCCN1Cc2[nH]c(-c3n[nH]c4cc(-c5cc(F)c(O)cc5CC)ccc34)nc2C[C@H]1C(=O)O]

To a solution of (S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, HCl (400 mg, 0.874 mmol) (8') and propionaldehyde (0.095 mL, 1.310 mmol) in DMF (7 mL), was added sodium cyanoborohydride (165 mg, 2.62 mmol) and the reaction mixture was stirred at RT overnight. Sodium borohydride (33 mg, 0.874 mmol) was added, the solution was concentrated, and purified by preparative HPLC to provide the TFA salt of the title compound (179 mg, 37% yield). (m/z): [M+H]$^+$ calcd for C$_{25}$H$_{26}$FN$_5$O$_3$ 464.20 found 464.5.

Preparation 7: (S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic acid

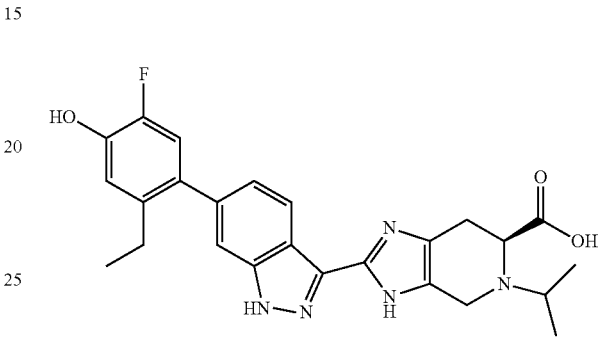

To a solution of (S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, HCl (8') (400 mg, 0.874 mmol), acetone (0.192 mL, 2.62 mmol), and acetic acid (0.150 mL, 2.62 mmol) in DMF (7 mL), was added sodium cyanoborohydride (274 mg, 4.37 mmol) and the reaction mixture was stirred at RT overnight. Sodium borohydride (33 mg, 0.874 mmol) was added, the solution was concentrated, and purified by preparative HPLC to provide the TFA salt of the title compound (115 mg, 23% yield). (m/z): [M+H]$^+$ calcd for C$_{25}$H$_{26}$FN$_5$O$_3$ 464.20 found 464.5.

Preparation 8: (S)-2-(6-(2-ethyl-5-fluoro-4-hydroxyphenyl)-1H-indazol-3-yl)-5-methyl-4,5,6,7-tetrahydro-3H-imidazo[4,5-c]pyridine-6-carboxylic acid

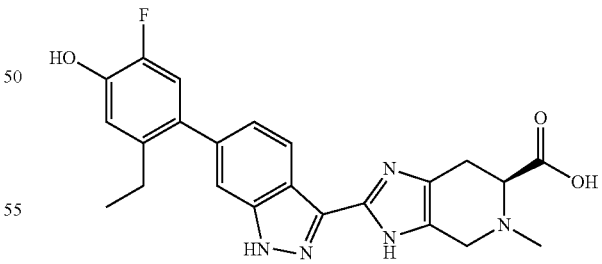

To a solution of (S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, HCl (8') (300 mg, 0.655 mmol) and 37 wt. % formaldehyde in water (0.059 mL, 0.786 mmol) DMF (5 mL), was added sodium cyanoborohydride (165 mg, 2.62 mmol) and the reaction mixture was stirred at RT overnight. Sodium borohydride 25 mg, 0.655 mmol) was added, the solution was concentrated, and purified by flash chromatography (100 g column, 5-75% ACN/ water), to provide the TFA salt of the title compound (85 mg, 24% yield). (m/z): [M+H]+ calcd for $C_{23}H_{22}FN_5O_3$ 436.17 found 436.45.

Preparation 9: (S)-5-ethyl-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid

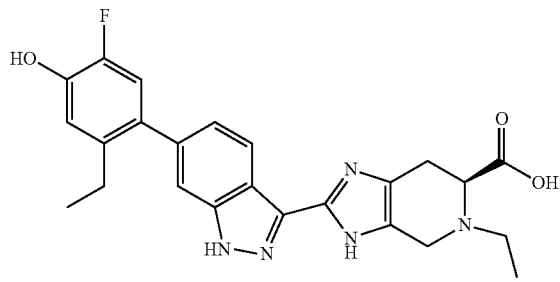 [SMILES: CCc1cc(O)c(F)cc1-c1ccc2c(-c3nc4c([nH]3)CN(CC)[C@H](C(=O)O)C4)n[nH]c2c1]

To a solution of (S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, HCl (8') (450 mg, 0.983 mmol) and acetaldehyde (0.083 mL, 1.474 mmol) in DMF (7 mL), was added sodium cyanoborohydride (247 mg, 3.93 mmol) and the reaction mixture was stirred at RT overnight. Sodium borohydride (112 mg, 2.95 mmol) was added, the solution was concentrated, dissolved in 1:1 acetic acid:water+300 µL TFA (7 mL) and purified by flash chromatography (100 g column, 5-65 ACN/water), to provide the TFA salt of the title compound (165 mg, 0.293 mmol, 30% yield). (m/z): [M+H]+ calcd for $C_{24}H_{24}FN_5O_3$ 450.19 found 450.

Example 1: ((S)-2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)((1S,4S)-5-methyl-2,5-diazabicyclo-[2.2.1]heptan-2-yl)methanone

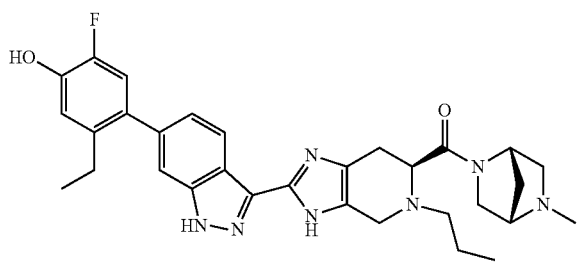 [SMILES: CCCN1Cc2[nH]c(-c3n[nH]c4cc(-c5cc(F)c(O)cc5CC)ccc34)nc2C[C@H]1C(=O)N1C[C@@H]2C[C@H]1CN2C]

To a solution of (S)-2-(6-(2-ethyl-5-fluoro-4-hydroxyphenyl)-1H-indazol-3-yl)-5-propyl-4,5,6,7-tetrahydro-3H-imidazo[4,5-c]pyridine-6-carboxylic acid, TFA (30 mg, 0.052 mmol), (1S,4S)-5-methyl-2,5-diazabicyclo[2.2.1]heptane dihydrobromide (42.7 mg, 0.156 mmol), and DIPEA (0.064 ml, 0.364 mmol) in DMF (1.5 ml), was added HATU (29.6 mg, 0.078 mmol) and the reaction mixture was stirred at RT overnight. Hydrazine (5 eq) was added, the reaction mixture was concentrated and purified by preparative HPLC to provide the TFA salt of the title compound (27 mg, 66% yield). (m/z): [M+H]+ calcd for $C_{31}H_{36}FN_7O_2$ 558.29 found 558.3. 1H NMR (400 MHz, Methanol-$d_4$) δ 8.17 (dt, 1H), 7.59-7.50 (m, 1H), 7.32 (dd, 1H), 6.95 (d, 1H), 6.90 (d, 1H), 5.03-4.91 (m, 2H), 4.56-4.34 (m, 2H), 4.30-3.88 (m, 4H), 3.76-3.55 (m, 1H), 3.28-3.10 (m, 1H), 3.10-2.96 (m, 4H), 2.81-2.62 (m, 2H), 2.53 (q, 2H), 2.47-2.33 (m, 1H), 2.31-2.14 (m, 1H), 1.79-1.57 (m, 2H), 1.07 (t, 3H), 0.97 (td, 3H).

Example 3: ((S)-3-(dimethylamino)pyrrolidin-1-yl)((S)-5-ethyl-2-(6-(2-ethyl-5-fluoro-4-hydroxyphenyl)-1H-indazol-3-yl)-4,5,6,7-tetrahydro-3H-imidazo[4,5-c]pyridin-6-yl)methanone

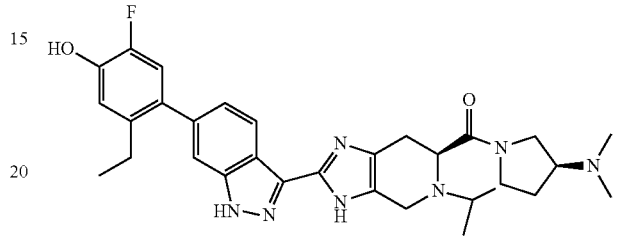

To a solution of (S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic acid, TFA (179 mg, 0.310 mmol), (S)—N,N-dimethylpyrrolidin-3-amine (0.079 mL, 0.620 mmol), and DIPEA (0.162 mL 0.930 mmol) in DMF (4 mL), was added HATU (177 mg, 0.465 mmol) and the reaction mixture was stirred at RT overnight. Hydrazine (5 eq) was added, the reaction mixture was concentrated and purified by preparative HPLC to provide the TFA salt of the title compound (107 mg, 44% yield). (m/z): [M+H]+ calcd for $C_{31}H_{38}FN_7O_2$ 560.31 found 560.2. 1H NMR (400 MHz, Methanol-$d_4$) δ 8.21 (d, 1H), 7.50 (s, 1H), 7.26 (d, 1H), 6.94 (d, 1H), 6.90 (d, 1H), 4.83-4.66 (m, 1H), 4.48-4.25 (m, 2H), 4.23-4.12 (m, 1H), 4.12-3.93 (m, 2H), 3.93-3.63 (m, 3H), 3.62-3.48 (m, 1H), 3.26-3.09 (m, 1H), 2.98 (d, 6H), 2.67-2.57 (m, 1H), 2.53 (q, 2H), 2.44-2.12 (m, 1H), 1.41 (t, 3H), 1.31 (d, 3H), 1.05 (t, 3H).

Example 5: (S)-(2-(6-(2-ethyl-5-fluoro-4-hydroxyphenyl)-1H-indazol-3-yl)-5-isopropyl-4,5,6,7-tetrahydro-3H-imidazo[4,5-c]pyridin-6-yl)(4-methyl-1,4-diazepan-1-yl)methanone

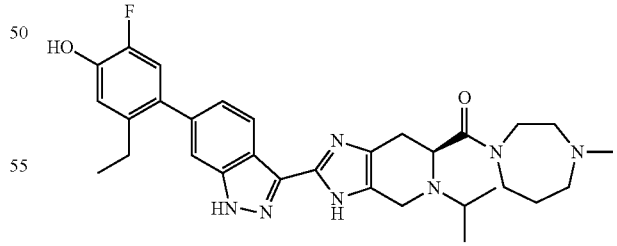

To a solution of (S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic acid, TFA (30 mg, 0.052 mmol), 1-methylhomopiperazine (0.019 mL, 0.156 mmol), and DIPEA (0.036 mL, 0.208 mmol) in DMF (1 mL), was added HATU (29.6 mg, 0.078 mmol) and the reaction mixture was stirred at RT for 3 h. Hydrazine (5 eq) was added, the reaction mixture was stirred at RT for 10 min, concentrated and purified by preparative HPLC to provide the TFA salt of the title compound (26.9 mg, 66% yield). (m/z): [M+H]⁺ calcd for $C_{31}H_{38}FN_7O_2$ 560.31 found 560.2.

Example 6: ((S)-2-(6-(2-ethyl-5-fluoro-4-hydroxyphenyl)-1H-indazol-3-yl)-5-methyl-4,5,6,7-tetrahydro-3H-imidazo[4,5-c]pyridin-6-yl)((R)-4-(2-hydroxyethyl)-2-methyl-piperazin-1-yl)methanone

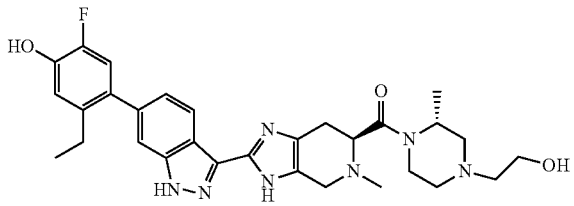 [SMILES: CCc1cc(O)c(F)cc1-c1ccc2c(-c3nc4c([nH]3)CN(C)[C@H](C(=O)N3CCN(CCO)C[C@H]3C)C4)n[nH]c2c1]

To a solution of (S)-2-(6-(2-ethyl-5-fluoro-4-hydroxyphenyl)-1H-indazol-3-yl)-5-methyl-4,5,6,7-tetrahydro-3H-imidazo[4,5-c]pyridine-6-carboxylic acid, TFA (30 mg, 0.052 mmol), (R)-2-(3-methylpiperazin-1-yl)ethanol, 2 HCl (35.6 mg, 0.164 mmol), and DIPEA (0.057 mL, 0.328 mmol) in DMF (1 mL), was added HATU (31.1 mg, 0.082 mmol) and the reaction mixture was stirred at RT overnight. Hydrazine (8.57 µL, 0.273 mmol) was added, the reaction mixture was concentrated and purified by preparative HPLC to provide the TFA salt of the title compound (15.6 mg, 36% yield). (m/z): [M+H]⁺ calcd for $C_{30}H_{36}FN_7O_3$ 562.29 found 562.2.

Example 7: (S)-(2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)(4-(2-hydroxyethyl)piperazin-1-yl)methanone

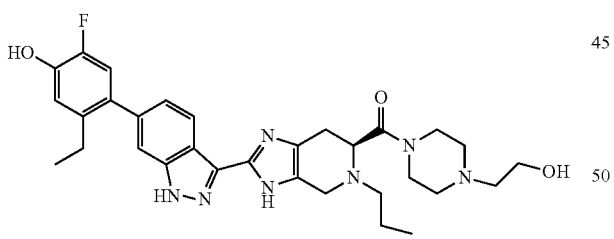

To a solution of (S)-2-(6-(2-ethyl-5-fluoro-4-hydroxyphenyl)-1H-indazol-3-yl)-5-propyl-4,5,6,7-tetrahydro-3H-imidazo[4,5-c]pyridine-6-carboxylic acid, TFA (30 mg, 0.052 mmol), 2-(piperazin-1-yl)ethanol, 2HCl (0.19 mL, 0.156 mmol), and DIPEA (0.027 mL, 0.156 mmol) in DMF (1.5 mL), was added HATU (29.6 mg, 0.078 mmol) and the reaction mixture was stirred at RT overnight. Hydrazine (5 eq) was added, the reaction mixture was concentrated and purified by preparative HPLC to provide the TFA salt of the title compound (15.4 mg, 37% yield). (m/z): [M+H]⁺ calcd for $C_{31}H_{38}FN_7O_3$ 576.30 found 576.2.

Preparation 10: tert-Butyl 2-(6-(2-ethyl-5-fluoro-4-methoxyphenyl)-1-(tetrahydro-2H-pyran-2-yl)-1H-indazol-3-yl)-6-(methoxy(methyl)carbamoyl)-3-((2-(trimethylsilyl)ethoxy)methyl)-3,4,6,7-tetrahydro-5H-imidazo[4,5-c]pyridine-5-carboxylate (17')

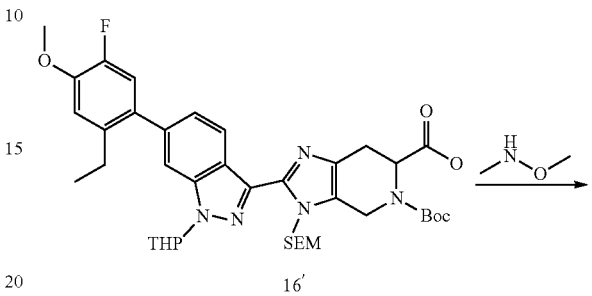

To a stirred solution of 5-(tert-butoxycarbonyl)-2-(6-(2-ethyl-5-fluoro-4-methoxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic acid (16') (4.0 g, 5.34 mmol) in DMF (20 mL) was added HATU (3.04 g, 8.01 mmol). The reaction mixture was stirred at RT fo 30 min and N,O-dimethylhydroxylamine HCl (628 mg. 6.4 mmol) and DIPEA (2.87 mL, 16.02 mml) were added and the reaction mixture was stirred at RT for 2 h. The resulting precipitate was filtered to provide crude solid which was purified by column chromatography over (100-200) silica gel, eluted with 20-30% EtOAc:hexane to provide the title compound (3.0 g, 71% yield) as a while solid. (m/z): [M+H]⁺ calcd for $C_{41}H_{57}FN_6O_7Si$ 793.40 found 793.6.

Preparation 11: tert-Butyl 2-(6-(2-ethyl-5-fluoro-4-methoxyphenyl)-1-(tetrahydro-2H-pyran-2-yl)-1H-indazol-3-yl)-6-formyl-3-((2-(trimethylsilyl)ethoxy)methyl)-3,4,6,7-tetrahydro-5H-imidazo[4,5-c]pyridine-5-carboxylate (12')

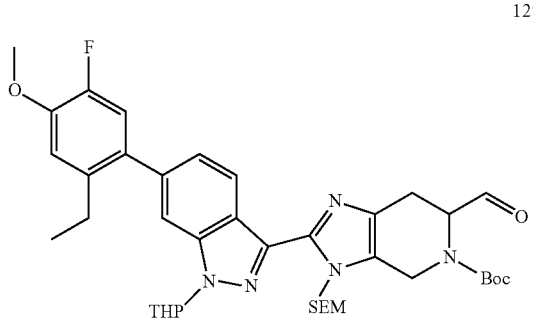

To a stirred solution of tert-butyl 2-(6-(2-ethyl-5-fluoro-4-methoxyphenyl)-1-(tetrahydro-2H-pyran-2-yl)-1H-indazol-3-yl)-6-(methoxy(methyl)carbamoyl)-3-((2-(trimethylsilyl)ethoxy)methyl)-3,4,6,7-tetrahydro-5H-imidazo[4,5-c]pyridine-5-carboxylate (17') (Preparation 10) (3.0 g, 3.78 mmol) in dry THF (30 mL) was added 1 M lithium aluminum hydride in THF (11.34 mL, 11.34 mmol) at −78° C. under nitrogen and the reaction mixture was stirred for 1 h. Ethyl acetate was added dropwise to quench the reaction and the mixture was stirred at 0° C. To the resulting suspension was added KHSO$_4$ (30 mL) dropwise and the reaction mixture was extracted with EtOAc. The organic layer was washed with brine, dried over anhydrous Na$_2$SO$_4$, filtered, and concentrated at 40° C. to provide the title product (2.4 g, 87% yield). $^1$H NMR consistent with structure. (m/z): [M+H]$^+$ calcd for C$_{39}$H$_{52}$FN$_5$O$_6$Si 734.37 found 734.59.

Preparation 12: 5-ethyl-2-fluoro-4-(3-(6-(pyrrolidin-1-ylmethyl)-4,5,6,7-tetrahydro-3H-imidazo[4,5-c]pyridin-2-yl)-1H-indazol-6-yl)phenol

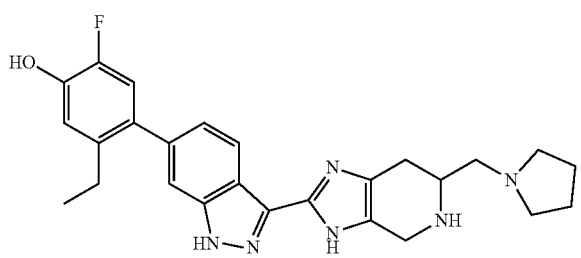 [SMILES: CCc1cc(O)c(F)cc1-c1ccc2c(-c3nc4c([nH]3)CNC(CN3CCCC3)C4)n[nH]c2c1]

(a) tert-Butyl 2-(6-(2-ethyl-5-fluoro-4-methoxyphenyl)-1-(tetrahydro-2H-pyran-2-yl)-1H-indazol-3-yl)-6-(pyrrolidin-1-ylmethyl)-3-((2-(trimethylsilyl)ethoxy)-methyl)-3,4,6,7-tetrahydro-5H-imidazo[4,5-c]pyridine-5-carboxylate tert-Butyl 2-(6-(2-ethyl-5-fluoro-4-methoxyphenyl)-1-(tetrahydro-2H-pyran-2-yl)-1H-indazol-3-yl)-6-formyl-3-((2-(trimethylsilyl)ethoxy)methyl)-3,4,6,7-tetrahydro-5H-imidazo[4,5-c]pyridine-5-carboxylate (12') (50 mg, 0.068 mmol), pyrrolidine (0.028 mL, 0.341 mmol), acetic acid (0.039 mL, 0.681 mmol), and sodium triacetoxyborohydride (144 mg, 0.681 mmol) were combined sequentially in DMF (1 mL) and stirred at RT overnight. The amorphous solid was taken up in EtOAc (10 mL) and washed with sat. aq NaHCO$_3$ (2×3 mL). The organics were dried over MgSO$_4$ and concentrated in vacuo to afford a colorless oil (50 mg, 93% yield).

(b) 5-ethyl-2-fluoro-4-(3-(6-(pyrrolidin-1-ylmethyl)-4,5,6,7-tetrahydro-3H-imidazo[4,5-c]pyridin-2-yl)-1H-indazol-6-yl)phenol The product of the previous step (0.05 g, 0.063 mmol) was dissolved in DCM (0.634 mL) and cooled to 0° C. Boron tribromide, 1 M in DCM (0.634 mL, 0.634 mmol) was added dropwise over several min and the reaction mixture was allowed to slowly warm to RT, stirred for 1 h, diluted with MeOH (10 mL) and concentrated in vacuo overnight. The crude residue was dissolved in dioxane (1 mL). Water (0.2 mL) was added followed by of 4 M HCl in dioxane (1 mL) and the reaction mixture was stirred at RT for 30 min, frozen to −78° C. and lyophilized. The lyophilized powder was dissolved in 4:1 water; acetic acid (10 mL), syringe filtered, and purified by preparative HPLC. Pure fractions were combined and lyophilized to provide the TFA salt of the title compound (32 mg, 73% yield). (m/z): [M+H]$^+$ calcd for C$_{26}$H$_{29}$FN$_6$O$_2$ 461.24 found 461.

Example 9: 5-ethyl-2-fluoro-4-(3-(5-methyl-6-(pyrrolidin-1-ylmethyl)-4,5,6,7-tetrahydro-3H-imidazo[4,5-c]pyridin-2-yl)-1H-indazol-6-yl)phenol

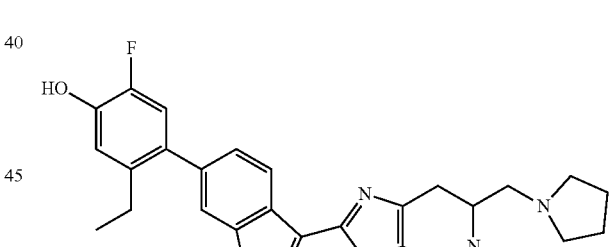

Formaldehyde (4.15 µl, 0.056 mmol) and 5-ethyl-2-fluoro-4-(3-(6-(pyrrolidin-1-ylmethyl)-4,5,6,7-tetrahydro-1H-imidazo[4,5-c]pyridin-2-yl)-1H-indazol-6-yl)phenol, 2TFA (Preparation 12) (32 mg, 0.046 mmol) were combined in MeOH (1 mL) at RT and stirred for 5 min. A solution of sodium cyanoborohydride (15 mg, 0.239 mmol) in MeOH (1 mL) was added and the reaction mixture was stirred overnight. Sodium borohydride (40 mg) was added and the reaction mixture was stirred for 3 h, concentrated, dissolved in 4:1 water:acetic acid and purified by preparative HPLC to provide the TFA salt of the title compound (10 mg, 30% yield). (m/z): [M+H]$^+$ calcd for C$_{27}$H$_{31}$FN$_6$O 475.25 found 475.2.

Preparation 13: (R)-pyrrolidin-3-yl 2-(6-(2-ethyl-5-fluoro-4-hydroxyphenyl)-1H-indazol-3-yl)-4,5,6,7-tetrahydro-3H-imidazo[4,5-c]pyridine-6-carboxylate Example 10: (R)-1-methylpyrrolidin-3-yl 2-(6-(2-ethyl-5-fluoro-4-hydroxyphenyl)-1H-indazol-3-yl)-5-methyl-4,5,6,7-tetrahydro-3H-imidazo[4,5-c]pyridine-6-carboxylate

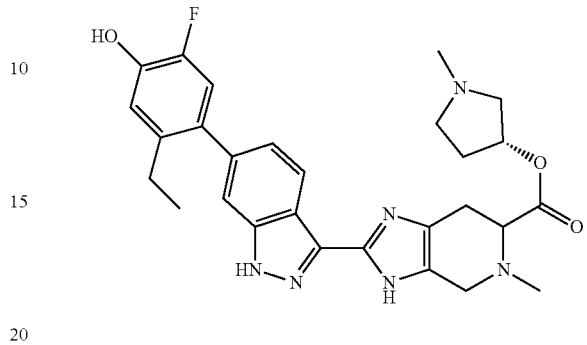

(R)-Pyrrolidin-3-yl 2-(6-(2-ethyl-5-fluoro-4-hydroxyphenyl)-1H-indazol-3-yl)-4,5,6,7-tetrahydro-3H-imidazo[4,5-c]pyridine-6-carboxylate, 2 TFA (12.1 mg, 0.017 mmol) and formaldehyde (1.504 μL, 0.020 mmol) were combined in MeOH (1 mL) and were stirred for 5 min. Sodium cyanoborohydride (5.40 mg, 0.086 mmol) was added and the reaction mixture was stirred at RT overnight, concentrated, and purified by preparative HPLC. Relevant fractions were combined, frozen, and lyophilized. The product was dissolved in MeOH (1 mL). Sodium borohydride (50 mg, 1.322 mmol) was added and the reaction mixture was stirred at RT overnight, concentrated, dissolved in 1:1 acetic acid: water (2 mL), filtered through a 0.2 μm syringe filter and purified by preparative HPLC to provide the TFA salt of the title compound (2.8 mg, 22% yield). (m/z): [M+H]$^+$ calcd for $C_{28}H_{31}FN_6O_3$ 519.24 found 519.1.

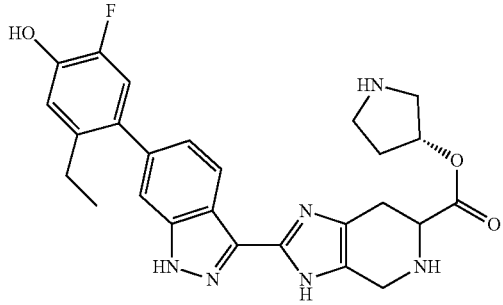 [SMILES: CCc1cc(O)c(F)cc1-c1ccc2c(-c3nc4c([nH]3)CNC(C(=O)O[C@@H]3CCNC3)C4)n[nH]c2c1]

(a) 6-((R)-1-(tert-Butoxycarbonyl)pyrrolidin-3-yl) 5-(tert-butyl) 2-(6-(2-ethyl-5-fluoro-4-methoxyphenyl)-1-(tetrahydro-2H-pyran-2-yl)-1H-indazol-3-yl)-3-((2-(trimethylsilyl)ethoxy)-methyl)-3,4,6,7-tetrahydro-5H-imidazo[4,5-c]pyridine-5,6-dicarboxylate To a solution of 5-(tert-butoxycarbonyl)-2-(6-(2-ethyl-5-fluoro-4-methoxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic acid (16') (50 mg, 0.067 mmol), tert-butyl (R)-3-hydroxypyrrolidine-1-carboxylate (312 mg, 1.667 mmol), and HATU (0.028 g, 0.073 mmol) in DMF (1.5 mL) was added DIPEA (0.046 mL, 0.267 mmol) and the reaction mixture was stirred at RT for 2.5 d, and concentrated to provide the title intermediate which was used directly in the next step.

(b) (R)-pyrrolidin-3-yl 2-(6-(2-ethyl-5-fluoro-4-hydroxyphenyl)-1H-indazol-3-yl)-4,5,6,7-tetrahydro-3H-imidazo[4,5-c]pyridine-6-carboxylate The product of the previous step (61 mg, 0.066 mmol) was dissolved in DCM (1 mL) and cooled to 0° C. Boron tribromide, 1 M in DCM (1.5 mL, 1.500 mmol) was added and the reaction mixture was stirred at RT for 1 h. Methanol (5 mL) was added and the reaction mixture was concentrated, dissolved in 20% water/dioxane (2 mL) and 4 M HCl in dioxane (2 mL, 8.00 mmol) was added. The reaction mixture was combined with the product of a run at the same scale and purified by preparative HPLC. Pure fractions were combined, frozen and lyophilized to provide the TFA salt of the title compound (20 mg, 21% yield) (m/z): [M+H]$^+$ calcd for $C_{26}H_7FN_6O_3$ 491.21 found 491.0.

Preparation 14: tert-Butyl 2-(6-(2-ethyl-5-fluoro-4-methoxyphenyl)-1-(tetrahydro-2H-pyran-2-yl)-1H-indazol-3-yl)-6-(hydroxymethyl)-3-((2-(trimethylsilyl)ethoxy)methyl)-3,4,6,7-tetrahydro-5H-imidazo[4,5-c]pyridine-5-carboxylate

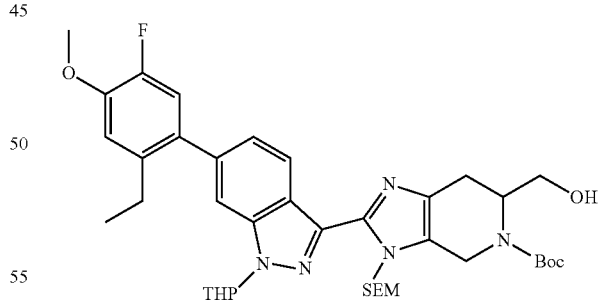

To a stirred solution of tert-butyl 2-(6-(2-ethyl-5-fluoro-4-methoxyphenyl)-1-(tetrahydro-2H-pyran-2-yl)-1H-indazol-3-yl)-6-formyl-3-((2-(trimethylsilyl)ethoxy)methyl)-3,4,6,7-tetrahydro-5H-imidazo[4,5-c]pyridine-5-carboxylate (12') (1.8 g, 2.45 mmol) in MeOH (20 mL) was added NaBH$_4$ (186 mg, 4.91 mmol) at 0° C. in portions. The resulting reaction mixture was stirred at RT for 1 h, concentrated, diluted with ice water and extracted with DCM. Organic layers were combined, washed with brine, dried over anhydrous Na$_2$SO$_4$, and concentrated to provide the title product (1.5 g, 90% yield). $^1$H NMR consistent with structure. (m/z): [M+H]$^+$ calcd for $C_{39}H_{54}FN_5O_6Si$ 736.38 found 736.59.

Preparation 15: 4-(3-(5-(azetidin-3-yl)-6-(hydroxymethyl)-4,5,6,7-tetrahydro-3H-imidazo[4,5-c]pyridin-2-yl)-1H-indazol-6-yl)-5-ethyl-2-fluorophenol

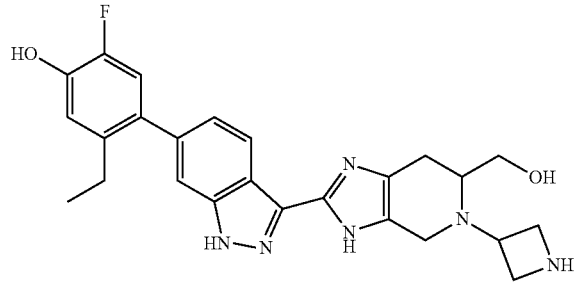 [SMILES: CCc1cc(O)c(F)cc1-c1ccc2c(-c3nc4c([nH]3)CN(C3CNC3)C(CO)C4)n[nH]c2c1]

(a) 5-ethyl-2-fluoro-4-(3-(6-(hydroxymethyl)-4,5,6,7-tetrahydro-3H-imidazo[4,5-c]pyridin-2-yl)-1H-indazol-6-yl)phenol tert-Butyl 2-(6-(2-ethyl-5-fluoro-4-methoxyphenyl)-1-(tetrahydro-2H-pyran-2-yl)-1H-indazol-3-yl)-6-(hydroxymethyl)-3-((2-(trimethylsilyl)ethoxy)methyl)-3,4,6,7-tetrahydro-5H-imidazo[4,5-c]pyridine-5-carboxylate (0.5 g, 0.679 mmol) was dissolved in DCM (7.5 mL) and stirred at RT. Boron tribromide, 1 M in DCM (5.10 mL, 5.10 mmol) was added and after 10 min, additional boron tribromide, 1 M in DCM (5.10 mL, 5.10 mmol). The reaction mixture was stirred at RT for 2 h, diluted with MeOH (45 mL), stirred for 5 min, and concentrated to dryness. The solid was dissolved in dioxane (5 mL) and water (1 mL), 4 M HCl in dioxane (5 mL, 20 mmol) was added and the reaction mixture was stirred at RT overnight, frozen, and lyophilized. The residue was combined with the residue of a run at the 0.1 g scale, dissolved in 4:1 water:acetic acid and purified by preparative HPLC. Pure fractions were combined and lyophilized to provide the TFA salt of the title intermediate 0.15 g, 42% yield) as a white powder. (m/z): [M+H]$^+$ calcd for $C_{22}H_{22}FN_5O_2$ 408.18 found 408.

(b) 4-(3-(5-(azetidin-3-yl)-6-(hydroxymethyl)-4,5,6,7-tetrahydro-3H-imidazo[4,5-c]pyridin-2-yl)-1H-indazol-6-yl)-5-ethyl-2-fluorophenol To a solution of the product of the previous step (50 mg, 0.123 mmol) in MeOH (1227 μL) was added tert-butyl 3-oxoazetidine-1-carboxylate (210 mg, 1.227 mmol). The reaction mixture was stirred for 1 h and then sodium cyanoborohydride (38.6 mg, 0.614 mmol) was added. The reaction mixture was stirred overnight, concentrated, treated with DCM (1 mL) and 4 M HCl in dioxane (1 mL), stirred at RT for 1 h, concentrated, coevaporated with ~5 mL EtOAc (5 mL), dissolved in 1:1 acetic acid:water and purified by preparative HPLC to provide the TFA salt of the title intermediate (19 mg, 33% yield) as a white powder. (m/z): [M+H]$^+$ calcd for $C_{25}H_{27}FN_6O_2$ 463.22 found 463.

Example 11: 5-ethyl-2-fluoro-4-(3-(6-(hydroxymethyl)-5-(1-methylazetidin-3-yl)-4,5,6,7-tetrahydro-3H-imidazo[4,5-c]pyridin-2-yl)-1H-indazol-6-yl)phenol

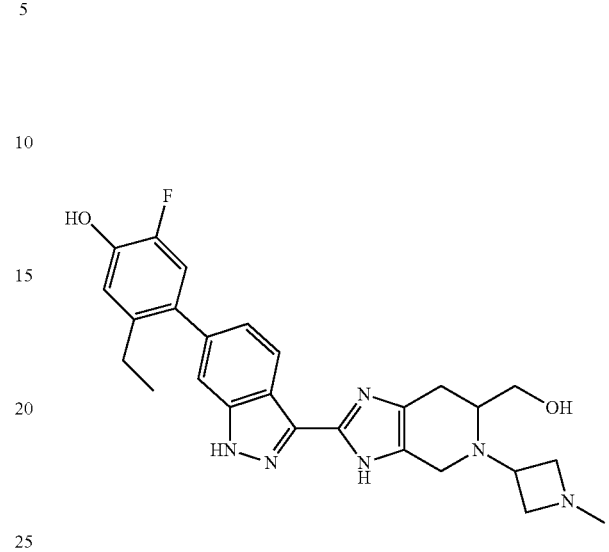

Formaldehyde (3.67 μL, 0.049 mmol) and 4-(3-(5-(azetidin-3-yl)-6-(hydroxymethyl)-4,5,6,7-tetrahydro-3H-imidazo[4,5-c]pyridin-2-yl)-1H-indazol-6-yl)-5-ethyl-2-fluorophenol (19 mg, 0.041 mmol) were combined in MeOH (8224) at RT and stirred for 5 min. A solution of sodium cyanoborohydride (12.91 mg, 0.205 mmol) in MeOH (1 mL) was added and the reaction mixture was stirred overnight. Sodium borohydride (7.77 mg, 0.205 mmol) was added and the reaction mixture was stirred for 2 h, concentrated, dissolved in 4:1 water:acetic acid, syringe filtered, and purified by preparative HPLC to provide the TFA salt of the title compound (9.2 mg, 46% yield. (m/z): [M+H]$^+$ calcd for $C_{26}H_{29}FN_6O_2$ 477.23 found 477.2.

Example 12: Methyl 2-(6-(2-ethyl-5-fluoro-4-hydroxyphenyl)-1H-indazol-3-yl)-5-(1-methylpiperidin-4-yl)-4,5,6,7-tetrahydro-3H-imidazo[4,5-c]pyridine-6-carboxylate

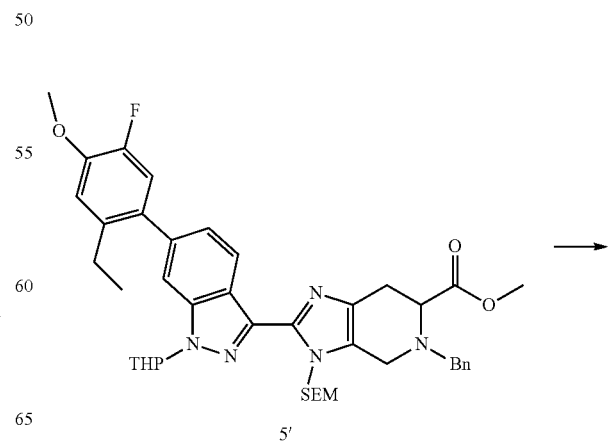

5'

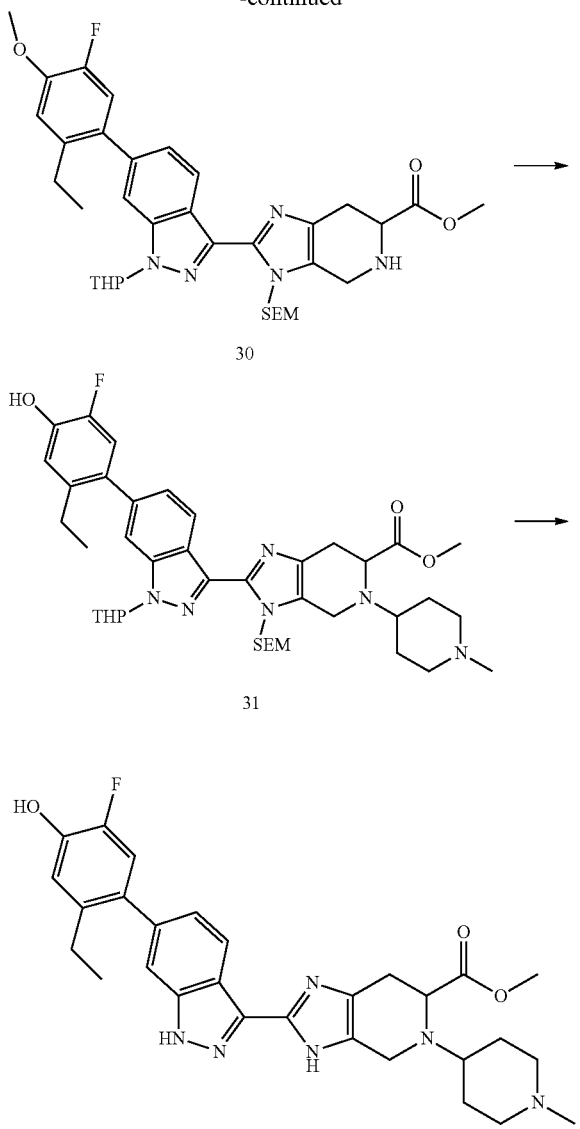

Ex. 12

(a) Methyl 2-(6-(2-ethyl-5-fluoro-4-methoxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylate (30)

A solution of methyl 5-benzyl-2-(6-(2-ethyl-5-fluoro-4-methoxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylate (5') (138 mg, 0.183 mmol), ammonium formate (346 mg, 5.49 mmol), and palladium hydroxide on carbon (51.4 mg, 0.073 mmol) in EtOH (3.66 ml) was purged with nitrogen for 10 min. The reaction vessel was sealed and the mixture stirred at 80° C. for 5 h, diluted with ethanol (10 mL), syringe filtered, concentrated, and purified by preparative HPLC. Relevant fractions were combined, frozen, and lyophilized to provide the TFA salt of the title intermediate (27 mg, 19% yield). (m/z): [M+H]+ calcd for $C_{35}H_{45}FN_5O_5Si$ 664.33 found 665.

(b) Methyl 2-(6-(2-ethyl-5-fluoro-4-methoxyphenyl)-1-(tetrahydro-2H-pyran-2-yl)-1H-indazol-3-yl)-5-(1-methylpiperidin-4-yl)-3-((2-(trimethylsilyl)ethoxy)methyl)-4,5,6,7-tetrahydro-3H-imidazo[4,5-c]pyridine-6-carboxylate (31)

The product of the previous step (30) (27 mg, 0.035 mmol), 1-methyl-4-piperidone (0.171 mL, 1.388 mmol), and acetic acid (0.079 mL, 1.388 mmol) were combined sequentially in DMF (2 ml). To the solution was added sodium triacetoxyborohydride (294 mg, 1.388 mmol) and the reaction mixture was stirred at RT overnight, concentrated, and purified by preparative HPLC. Relevant fractions were combined and concentrated to a clear oil to provide the TFA salt of the title intermediate (33.3 mg, 97% yield). (m/z): [M+H]+ calcd for $C_{41}H_{57}FN_6O_5Si$ 761.41 found 762.

(c) Methyl 2-(6-(2-ethyl-5-fluoro-4-hydroxyphenyl)-1H-indazol-3-yl)-5-(1-methylpiperidin-4-yl)-4,5,6,7-tetrahydro-3H-imidazo[4,5-c]pyridine-6-carboxylate The product of the previous step (31) (26.6 mg, 0.035 mmol) was dissolved in DCM (0.70 mL) and cooled to 0° C. and a 1 M solution of boron tribromide in DCM (0.350 mL, 0.350 mmol) was added. The reaction mixture was stirred at RT for 50 min, quenched with MeOH (5 mL), concentrated, and dissolved in 20% water/dioxane (1 mL). To the solution was added 4.0 M HCl in dioxane (1 mL, 4.00 mmol) and the reaction mixture was stirred at RT overnight, concentrated, and dissolved in MeOH (2 mL). To the solution was added ethylenediamine (9.38 µL, 0.140 mmol) and the reaction mixture was stirred at RT for 7 h and purified by preparative HPLC. Relevant fractions were combined, frozen, and lyophilized to provide the TFA salt of the title compound (9.2 mg, 35% yield). (m/z): [M+H]+ calcd for $C_{29}H_{33}FN_6O_3$ 533.26 found 533.

Preparation 16: (6S)-tert-butyl 6-((S)-4-(tert-butoxycarbonyl)-2-methylpiperazine-1-carbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-6,7-dihydro-3H-imidazo[4,5-c]pyridine-5(4H)-carboxylate

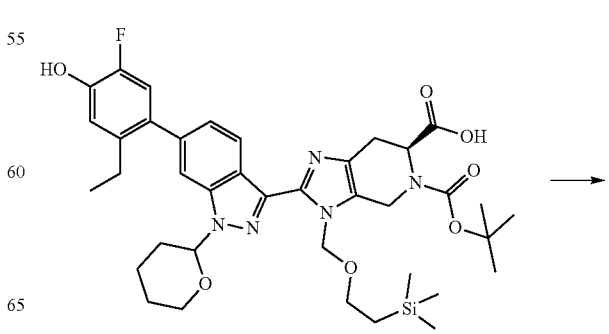

55

-continued

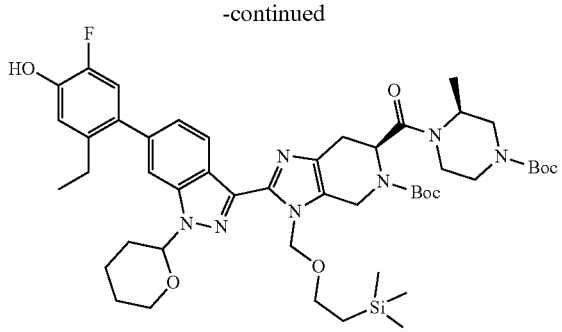

(6S)-5-(tert-butoxycarbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic acid (50 mg, 0.068 mmol), (S)-4-n-boc-2-methylpiperazine (40.8 mg, 0.204 mmol), and DIPEA (0.036 ml, 0.204 mmol) were dissolved in DMF (1.0 ml), then HATU (38.8 mg, 0.102 mmol) was added and the reaction mixture was stirred at room temperature for 16 hours. The reaction mixture was concentrated and the crude product was purified by silica gel chromatography (0-100% EtOAc/Hexanes gradient) to afford the title compound (53 mg, 84% yield). (m/z): [M+H]+ calcd for $C_{48}H_{68}FN_7O_8Si$ 919.2 found 919.1.

Preparation 17: ((S)-2-(6-(2-ethyl-5-fluoro-4-hydroxyphenyl)-1H-indazol-3-yl)-4,5,6,7-tetrahydro-3H-imidazo[4,5-c]pyridin-6-yl)((S)-2-methylpiperazin-1-yl)methanone

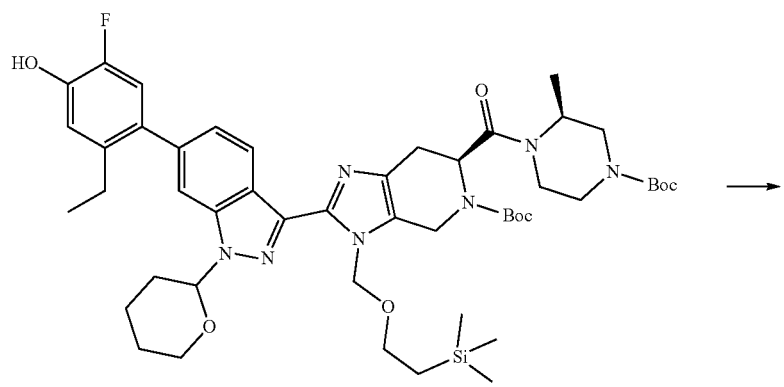

56

(6S)-tert-butyl 6-((S)-4-(tert-butoxycarbonyl)-2-methylpiperazine-1-carbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-6,7-dihydro-3H-imidazo[4,5-c]pyridine-5(4H)-carboxylate (52.7 mg, 0.057 mmol) was dissolved in dioxane (1.0 ml) and water (0.2 ml), then HCl, 4M in dioxane (1.0 ml, 4.00 mmol) was added and the reaction mixture was stirred at 50° C. for 16 hours. The reaction mixture was frozen and lyophilized, then the resulting solid was dissolved in 2 mL of MeOH. Ethylenediamine (0.015 ml, 0.230 mmol) and sodium borohydride (13.03 mg, 0.344 mmol) were then added and the reaction mixture was stirred at room temperature for 12 hours. The solution was then concentrated and purified by preparative HPLC to provide the TFA salt of the title compound (18 mg, 42% yield). (m/z): [M+H]+ calcd for $C_{27}H_{30}FN_7O_2$ 504.6 found 504.5.

Example 2-15: (S)-2,4-dimethylpiperazin-1-yl)((S)-2-(6-(2-ethyl-5-fluoro-4-hydroxyphenyl)-1H-indazol-3-yl)-5-methyl-4,5,6,7-tetrahydro-3H-imidazo[4,5-c]pyridin-6-yl)methanone

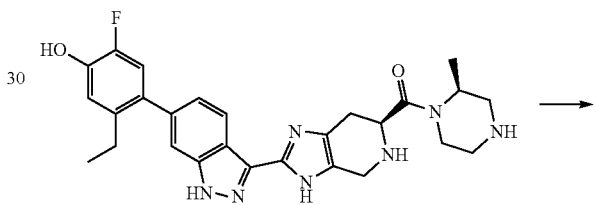

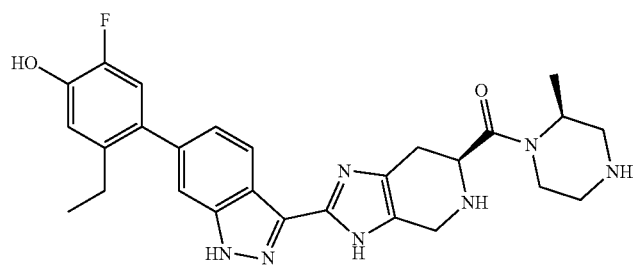

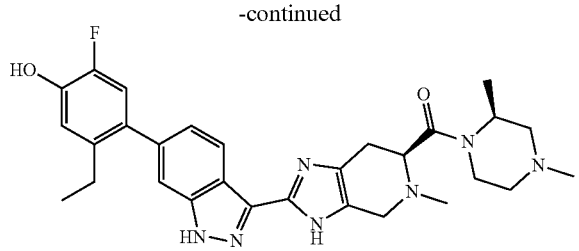

((S)-2-(6-(2-ethyl-5-fluoro-4-hydroxyphenyl)-1H-indazol-3-yl)-4,5,6,7-tetrahydro-3H-imidazo[4,5-c]pyridin-6-yl)((S)-2-methylpiperazin-1-yl)methanone, 2TFA (17.7 mg, 0.024 mmol) and formaldehyde, 37% in water (4.50 μl, 0.060 mmol) were dissolved in methanol (1.0 ml), then sodium cyanoborohydride (7.60 mg, 0.121 mmol) was added and the reaction mixture was stirred at room temperature for 3 hours. Sodium borohydride (0.024 mmol) was added to quench any remaining formaldehyde, then the solution was concentrated. The crude product was then purified by preparative HPLC to provide the TFA salt of the title compound (12 mg, 66% yield). (m/z): [M+H]+ calcd for $C_{29}H_{34}FN_7O_2$ 532.6 found 532.2.

Example 12-14: (R)—N-(2-(diethylamino)ethyl)-5-ethyl-2-(6-(2-ethyl-5-fluoro-4-hydroxyphenyl)-1H-indazol-3-yl)-N-methyl-4,5,6,7-tetrahydro-3H-imidazo[4,5-c]pyridine-6-carboxamide

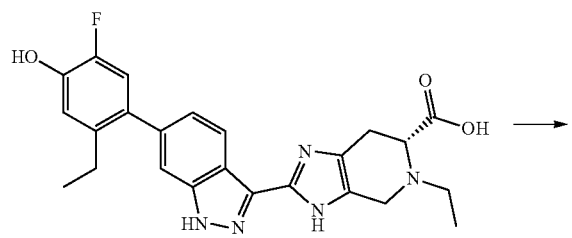

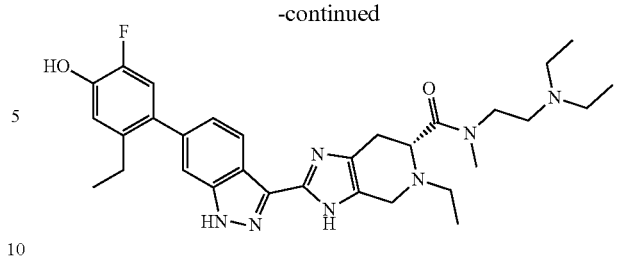

(R)-5-ethyl-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, TFA (40 mg, 0.071 mmol), N1,N1-diethyl-N2-methylethane-1,2-diamine (0.046 ml, 0.284 mmol), and DIPEA (0.062 ml, 0.355 mmol) were dissolved in DMF (2.0 ml), then HATU (32.4 mg, 0.085 mmol) was added and the reaction mixture was stirred at room temperature for 16 hours. Hydrazine (0.011 ml, 0.355 mmol) was added and the reaction mixture was stirred at room temperature for 10 minutes. The solution was then concentrated purified by preparative HPLC to provide the TFA salt of the title compound (24 mg, 42% yield). (m/z): [M+H]+ calcd for $C_{31}H_{40}FN_7O_2$ 562.7 found 562.7.

Using similar synthetic methods, the compounds of Tables 1-19 were prepared. In the following tables, a blank in any column indicates a hydrogen atom, a * in a structure heading a table indicates a chiral center, and the notation (R) or (S) in front of a substituent denotes the configuration of the carbon atom to which the substituent is attached.

TABLE 1

| Ex. No. | * | $R^1$ | $R^3$ | Formula | Calc [M + H]+ | Found [M + H]+ |
|---|---|---|---|---|---|---|
| 1-1 | | H | CH₃ | $C_{27}H_{30}FN_7O_2$ | 504.24 | 504.1 |
| 1-2 | | H | iPr | $C_{29}H_{34}FN_7O_2$ | 532.28 | 532.3 |
| 1-3 | | H | CH₂CH₂OH | $C_{28}H_{32}FN_7O_3$ | 534.26 | 534.2 |
| 1-4 | | H | cpentyl | $C_{31}H_{36}FN_7O_2$ | 558.29 | 558.3 |
| 1-5 | | H | chexyl | $C_{32}H_{38}FN_7O_2$ | 572.31 | 572.3 |
| 1-6 | | H | cpropyl | $C_{29}H_{32}FN_7O_2$ | 530.26 | 530.2 |
| 1-7 | | CH₃ | CH₃ | $C_{28}H_{32}FN_7O_2$ | 518.26 | 518.1 |
| 1-8 | | CH₃ | cpropyl | $C_{30}H_{34}FN_7O_2$ | 544.28 | 544.2 |
| 1-9 | | CH₃ | chexyl | $C_{33}H_{40}FN_7O_2$ | 586.32 | 586.2 |
| 1-10 | | CH₃ | CH₂CH₂OH | $C_{29}H_{34}FN_7O_3$ | 548.27 | 548 |
| 1-11 | | CH₃ | cpentyl | $C_{32}H_{38}FN_7O_2$ | 572.31 | 572 |
| 1-12 | | CH₃ | iPr | $C_{30}H_{36}FN_7O_2$ | 546.29 | 547 |

TABLE 1-continued

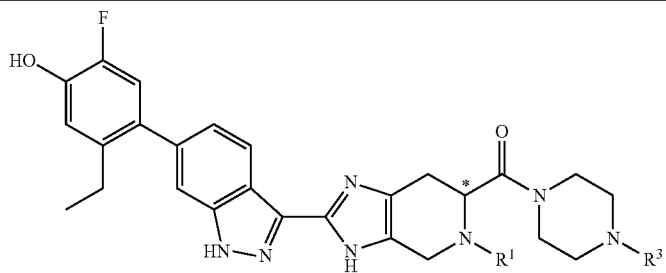

| Ex. No. | * | $R^1$ | $R^3$ | Formula | Calc [M + H]$^+$ | Found [M + H]$^+$ |
|---|---|---|---|---|---|---|
| 1-13 |  | $C_2H_5$ | iPr | $C_{31}H_{38}FN_7O_2$ | 560.31 | 560 |
| 1-14 |  | $C_2H_5$ | $CH_2CH_2OH$ | $C_{30}H_{36}FN_7O_3$ | 562.29 | 562 |
| 1-15 | (S) | $CH_3$ | iPr | $C_{30}H_{36}FN_7O_2$ | 546.29 | 546 |
| 1-16 | (R) | $CH_3$ | iPr | $C_{30}H_{36}FN_7O_2$ | 546.29 | 546 |
| 1-17 |  | iPr | $CH_2CH_2OH$ | $C_{31}H_{38}FN_7O_3$ | 576.30 | 576.2 |
| 1-18 |  | nPr | $CH_2CH_2OH$ | $C_{31}H_{38}FN_7O_3$ | 576.30 | 576.9 |
| 1-19 | (S) | $CH_3$ | $CH_2CH_2OH$ | $C_{29}H_{34}FN_7O_3$ | 548.27 | 548.2 |
| 1-20 | (R) | $CH_3$ | $CH_2CH_2OH$ | $C_{29}H_{34}FN_7O_3$ | 548.27 | 548.2 |
| 1-21 | (S) | $CH_3$ | $CH_3$ | $C_{28}H_{32}FN_7O_2$ | 518.26 | 518.3 |
| 1-22 | (R) | $CH_3$ | $CH_3$ | $C_{28}H_{32}FN_7O_2$ | 518.26 | 518.3 |
| 1-23 |  | iPr | iPr | $C_{32}H_{40}FN_7O_2$ | 574.32 | 573.8 |
| 1-24 |  | $CH_3$ | tBu | $C_{31}H_{38}FN_7O_2$ | 560.31 | 559.7 |
| 1-25 |  | $C_2H_5$ | tBu | $C_{32}H_{40}FN_7O_2$ | 574.32 | 573.7 |
| 1-26 |  | nPr | tBu | $C_{33}H_{42}FN_7O_2$ | 588.34 | 587.7 |
| 1-27 |  | iPr | tBu | $C_{33}H_{42}FN_7O_2$ | 588.34 | 587.8 |
| 1-28 | (R) | nPr | $CH_2CH_2OH$ | $C_{31}H_{38}FN_7O_3$ | 576.30 | 576.2 |
| 1-29 | (S) | $C_2H_5$ | $CH_2CH_2OH$ | $C_{30}H_{36}FN_7O_3$ | 562.29 | 562.5 |
| 1-30 | (R) | $C_2H_5$ | $CH_2CH_2OH$ | $C_{30}H_{36}FN_7O_3$ | 562.29 | 562.5 |
| 1-31 |  | $CH_3$ | H | $C_{27}H_{30}FN_7O_2$ | 504.24 | 504.2 |
| 1-32 |  | $C_2H_5$ | $CH_3$ | $C_{29}H_{34}FN_7O_2$ | 532.28 | 532.2 |
| 1-33 |  | nPr | $CH_3$ | $C_{30}H_{36}FN_7O_2$ | 546.29 | 546.2 |
| 1-34 |  | iPr | $CH_3$ | $C_{30}H_{36}FN_7O_2$ | 546.29 | 546.3 |
| 1-35 |  | nPr | H | $C_{29}H_{34}FN_7O_2$ | 532.28 | 532.2 |
| 1-36 | (S) | $C_2H_5$ | tBu | $C_{32}H_{40}FN_7O_2$ | 574.32 | 574.3 |
| 1-37 | (R) | $C_2H_5$ | tBu | $C_{32}H_{40}FN_7O_2$ | 574.32 | 574.3 |
| 1-38 |  | iPr | H | $C_{29}H_{34}FN_7O_2$ | 532.28 | 532.2 |
| 1-39 | (R) | iPr | H | $C_{29}H_{34}FN_7O_2$ | 532.28 | 532.2 |
| 1-40 | (S) | iPr | H | $C_{29}H_{34}FN_7O_2$ | 532.28 | 532.2 |

TABLE 2

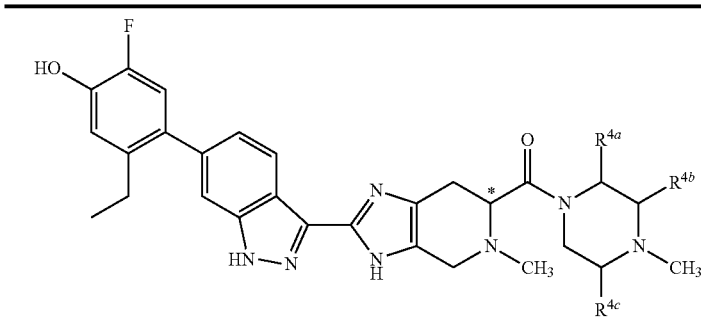

| Ex. No. | * | $R^{4a}$ | $R^{4b}$ | $R^{4c}$ | Formula | Calc [M + H]$^+$ | Found [M + H]$^+$ |
|---|---|---|---|---|---|---|---|
| 2-1 |  |  | (S)$CH_3$ | (R)$CH_3$ | $C_{30}H_{36}FN_7O_2$ | 546.29 | 546 |
| 2-2 |  | (R)$CH_3$ |  |  | $C_{29}H_{34}FN_7O_2$ | 532.28 | 532 |
| 2-3 |  | (S)$CH_3$ |  |  | $C_{29}H_{34}FN_7O_2$ | 532.28 | 532 |
| 2-4 |  | (S)$CH_3$ |  | (R)$CH_3$ | $C_{30}H_{36}FN_7O_2$ | 546.29 | 546 |
| 2-5 |  |  | (S)$CH_3$ |  | $C_{29}H_{34}FN_7O_2$ | 532.28 | 532 |
| 2-6 |  |  | (R)$CH_3$ |  | $C_{29}H_{34}FN_7O_2$ | 532.28 | 532 |
| 2-7 |  | (R)$CH_3$ |  | (R)$CH_3$ | $C_{30}H_{36}FN_7O_2$ | 546.29 | 546 |
| 2-8 | (S) | (R)$CH_3$ |  |  | $C_{29}H_{34}FN_7O_2$ | 532.28 | 532 |
| 2-9 | (R) | (R)$CH_3$ |  |  | $C_{29}H_{34}FN_7O_2$ | 532.28 | 532 |
| 2-10 | (S) |  | (R)$CH_3$ |  | $C_{29}H_{34}FN_7O_2$ | 532.28 | 531.7 |

TABLE 2-continued

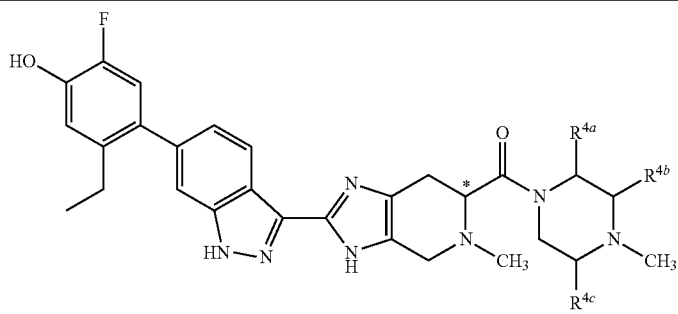

| Ex. No. | * | $R^{4a}$ | $R^{4b}$ | $R^{4c}$ | Formula | Calc [M + H]$^+$ | Found [M + H]$^+$ |
|---|---|---|---|---|---|---|---|
| 2-11 | (S) |  | (S)CH$_3$ |  | C$_{29}$H$_{34}$FN$_7$O$_2$ | 532.28 | 531.8 |
| 2-12 | (R) |  | (S)CH$_3$ |  | C$_{29}$H$_{34}$FN$_7$O$_2$ | 532.28 | 531.7 |
| 2-13 | (R) |  | (R)CH$_3$ |  | C$_{29}$H$_{34}$FN$_7$O$_2$ | 532.28 | 531.7 |
| 2-14 |  | (R)CH$_3$ |  | (S)CH$_3$ | C$_{30}$H$_{36}$FN$_7$O$_2$ | 546.29 | 546 |
| 2-15 | (S) | (S)CH$_3$ |  |  | C$_{29}$H$_{34}$FN$_7$O$_2$ | 532.28 | 532.3 |
| 2-16 | (S) | (S)CH$_3$ |  | (R)CH$_3$ | C$_{30}$H$_{36}$FN$_7$O$_2$ | 546.29 | 546.3 |
| 2-17 | (S) | (R)CH$_3$ |  | (R)CH$_3$ | C$_{30}$H$_{36}$FN$_7$O$_2$ | 546.29 | 546.6 |
| 2-18 | (R) | (S)CH$_3$ |  |  | C$_{29}$H$_{34}$FN$_7$O$_2$ | 532.28 | 532.2 |
| 2-19 | (R) | (S)CH$_3$ |  | (R)CH$_3$ | C$_{30}$H$_{36}$FN$_7$O$_2$ | 546.29 | 546.6 |
| 2-20 | (R) | (R)CH$_3$ |  | (R)CH$_3$ | C$_{30}$H$_{36}$FN$_7$O$_2$ | 546.29 | 546.2 |
| 2-21 |  | (S)C$_2$H$_5$ |  |  | C$_{30}$H$_{36}$FN$_7$O$_2$ | 546.29 | 545.7 |
| 2-22 |  | (R)C$_2$H$_5$ |  |  | C$_{30}$H$_{36}$FN$_7$O$_2$ | 546.29 | 545.8 |

TABLE 3

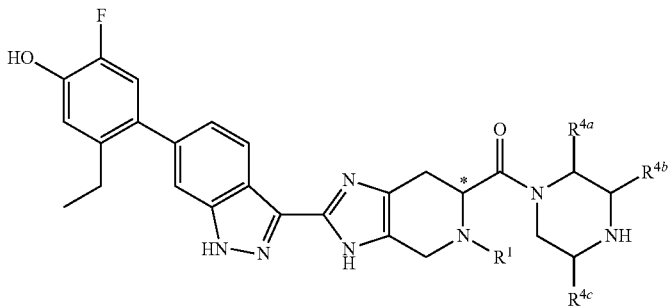

| Ex. No. | * | $R^1$ | $R^{4a}$ | $R^{4b}$ | $R^{4c}$ | Formula | Calc [M + H]$^+$ | Found [M + H]$^+$ |
|---|---|---|---|---|---|---|---|---|
| 3-1 |  | H |  | (S)CH$_3$ | (R)CH$_3$ | C$_{28}$H$_{32}$FN$_7$O$_2$ | 518.26 | 518.2 |
| 3-2 |  | CH$_3$ | (R)CH$_3$ |  |  | C$_{28}$H$_{32}$FN$_7$O$_2$ | 518.26 | 517.7 |
| 3-3 |  | CH$_3$ | (R)CH$_3$ |  | (R)CH$_3$ | C$_{29}$H$_{34}$FN$_7$O$_2$ | 532.28 | 532.2 |
| 3-4 |  | CH$_3$ | (S)CH$_3$ |  |  | C$_{28}$H$_{32}$FN$_7$O$_2$ | 518.26 | 518.2 |
| 3-5 |  | CH$_3$ | (S)CH$_3$ |  | (R)CH$_3$ | C$_{29}$H$_{34}$FN$_7$O$_2$ | 532.28 | 532.2 |
| 3-6 |  | CH$_3$ |  | (S)CH$_3$ |  | C$_{28}$H$_{32}$FN$_7$O$_2$ | 518.26 | 518.2 |
| 3-7 |  | nPr | (S)CH$_3$ |  |  | C$_{30}$H$_{36}$FN$_7$O$_2$ | 546.29 | 546 |
| 3-8 |  | nPr | (R)CH$_3$ |  |  | C$_{30}$H$_{36}$FN$_7$O$_2$ | 546.29 | 546 |
| 3-9 |  | nPr | (S)CH$_3$ |  | (R)CH$_3$ | C$_{31}$H$_{38}$FN$_7$O$_2$ | 560.31 | 560 |
| 3-10 |  | nPr | (R)CH$_3$ |  | (R)CH$_3$ | C$_{31}$H$_{38}$FN$_7$O2 | 560.31 | 560 |
| 3-11 |  | nPr |  | (S)CH$_3$ |  | C$_{30}$H$_{36}$FN$_7$O$_2$ | 546.29 | 546 |
| 3-12 |  | iPr | (S)CH$_3$ |  | (R)CH$_3$ | C$_{31}$H$_{38}$FN$_7$O$_2$ | 560.31 | 560.2 |
| 3-13 |  | iPr | (S)CH$_3$ |  |  | C$_{30}$H$_{36}$FN$_7$O$_2$ | 546.29 | 546.2 |
| 3-14 |  | iPr |  | (S)CH$_3$ |  | C$_{30}$H$_{36}$FN$_7$O$_2$ | 546.29 | 546.3 |
| 3-15 |  | iPr | (R)CH$_3$ |  |  | C$_{30}$H$_{36}$FN$_7$O$_2$ | 546.29 | 546.2 |
| 3-16 |  | iPr | (R)CH$_3$ |  | (R)CH$_3$ | C$_{31}$H$_{38}$FN$_7$O$_2$ | 560.31 | 560.3 |
| 3-17 | (S) | CH$_3$ | (R)CH$_3$ |  |  | C$_{28}$H$_{32}$FN$_7$O$_2$ | 518.26 | 518.4 |
| 3-18 | (R) | CH$_3$ | (R)CH$_3$ |  |  | C$_{28}$H$_{32}$FN$_7$O$_2$ | 518.26 | 518.3 |
| 3-19 | (R) | CH$_3$ | (S)C$_2$H$_5$ |  |  | C$_{29}$H$_{34}$FN$_7$O$_2$ | 532.28 | 532.3 |
| 3-20 | (R) | CH$_3$ | (R)C$_2$H$_5$ |  |  | C$_{29}$H$_{34}$FN$_7$O$_2$ | 532.28 | 532.2 |
| 3-21 | (S) | nPr | (R)CH$_3$ |  | (R)CH$_3$ | C$_{31}$H$_{38}$FN$_7$O$_2$ | 560.31 | 560.3 |
| 3-22 | (S) | CH$_3$ | (R)C$_2$H$_5$ |  |  | C$_{29}$H$_{34}$FN$_7$O$_2$ | 532.28 | 532.3 |
| 3-23 | (S) | nPr |  | (S)CH$_3$ |  | C$_{28}$H$_{32}$FN$_7$O$_2$ | 518.26 | 517.7 |
| 3-24 | (R) | nPr | (R)CH$_3$ |  | (R)CH$_3$ | C$_{29}$H$_{34}$FN$_7$O$_2$ | 532.28 | 532.2 |

TABLE 3-continued

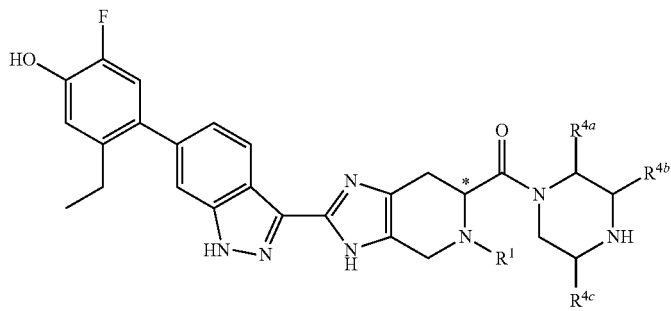

| Ex. No. | * | R¹ | R⁴ᵃ | R⁴ᵇ | R⁴ᶜ | Formula | Calc [M + H]⁺ | Found [M + H]⁺ |
|---|---|---|---|---|---|---|---|---|
| 3-25 | (R) | nPr | | | (S)CH₃ | $C_{28}H_{32}FN_7O_2$ | 518.26 | 518.2 |
| 3-26 | (S) | CH₃ | (S)C₂H₅ | | | $C_{29}H_{34}FN_7O_2$ | 532.28 | 532.2 |

TABLE 4

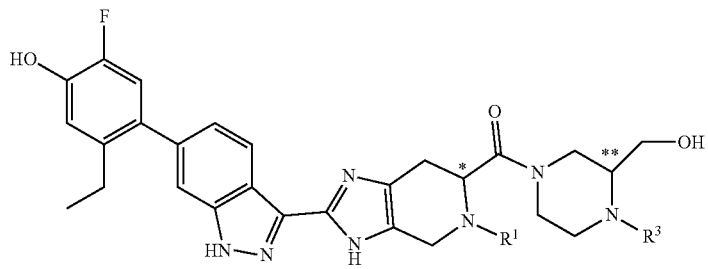

| Ex. No. | * | ** | R¹ | R³ | Formula | Calc [M + H]⁺ | Found [M + H]⁺ |
|---|---|---|---|---|---|---|---|
| 4-1 | | (R) | CH₃ | CH₃ | $C_{29}H_{34}FN_7O_3$ | 548.27 | 548.7 |
| 4-2 | | (S) | CH₃ | CH₃ | $C_{29}H_{34}FN_7O_3$ | 548.27 | 548.7 |
| 4-3 | (R) | (S) | C₂H₅ | CH₃ | $C_{30}H_{36}FN_7O_3$ | 562.29 | 562.2 |
| 4-4 | (R) | (R) | C₂H₅ | CH₃ | $C_{30}H_{36}FN_7O_3$ | 562.29 | 562.2 |
| 4-5 | (R) | (R) | nPr | CH₃ | $C_{31}H_{38}FN_7O_3$ | 576.30 | 576.3 |
| 4-6 | (R) | (S) | nPr | CH₃ | $C_{31}H_{38}FN_7O_3$ | 576.30 | 576.2 |
| 4-7 | (R) | (R) | iPr | CH₃ | $C_{31}H_{38}FN_7O_3$ | 576.30 | 576.2 |
| 4-8 | (R) | (S) | iPr | CH₃ | $C_{31}H_{38}FN_7O_3$ | 576.30 | 576.2 |
| 4-9 | (S) | (R) | iPr | CH₃ | $C_{31}H_{38}FN_7O_3$ | 576.30 | 576.2 |
| 4-10 | (S) | (R) | C₂H₅ | CH₃ | $C_{30}H_{36}FN_7O_3$ | 562.29 | 562 |
| 4-11 | (S) | (S) | C₂H₅ | CH₃ | $C_{30}H_{36}FN_7O_3$ | 562.29 | 562 |
| 4-12 | (S) | (R) | nPr | CH₃ | $C_{31}H_{38}FN_7O_3$ | 576.30 | 576 |
| 4-13 | (S) | (S) | iPr | CH₃ | $C_{31}H_{38}FN_7O_3$ | 576.30 | 576.2 |

TABLE 5

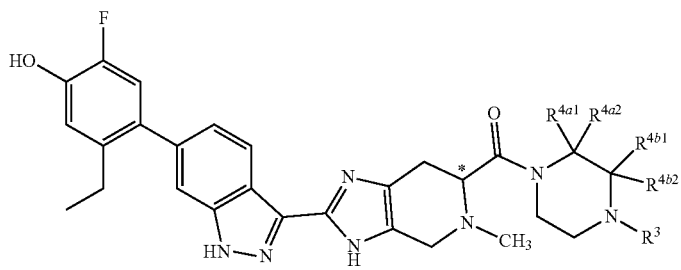

| Ex. No. | * | R⁴ᵃ¹ | R⁴ᵃ² | R⁴ᵇ¹ | R⁴ᵇ² | R³ | Formula | Calc [M + H]⁺ | Found [M + H]⁺ |
|---|---|---|---|---|---|---|---|---|---|
| 5-1 | | CH₃ | CH₃ | | | CH₃ | $C_{30}H_{36}FN_7O_2$ | 546.29 | 546 |
| 5-2 | (R) | CH₃ | CH₃ | | | CH₃ | $C_{30}H_{36}FN_7O_2$ | 546.29 | 546.2 |
| 5-3 | (S) | CH₃ | CH₃ | | | CH₃ | $C_{30}H_{36}FN_7O_2$ | 546.29 | 546.2 |

TABLE 5-continued

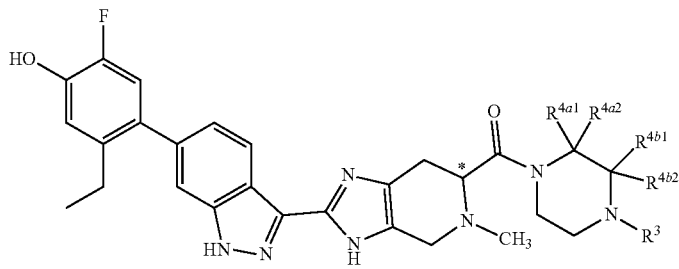

| Ex. No. | * | $R^{4a1}$ | $R^{4a2}$ | $R^{4b1}$ | $R^{4b2}$ | $R^3$ | Formula | Calc [M + H]$^+$ | Found [M + H]$^+$ |
|---|---|---|---|---|---|---|---|---|---|
| 5-4 | | | | —(CH$_2$)$_3$— | | CH$_3$ | C$_{31}$H$_{36}$FN$_7$O$_2$ | 558.29 | 557.8 |
| 5-5 | | (R)CH$_3$ | | | | Et | C$_{30}$H$_{36}$FN$_7$O$_2$ | 546.29 | 546.2 |
| 5-6 | | (R)CH$_3$ | | | | iPr | C$_{31}$H$_{38}$FN$_7$O$_2$ | 560.31 | 560.2 |
| 5-7 | | (R)CH$_3$ | | | | cBu | C$_{32}$H$_{38}$FN$_7$O$_2$ | 572.31 | 571.6 |
| 5-8 | | (R)CH$_3$ | | | | (a) | C$_{30}$H$_{36}$FN$_7$O$_3$ | 562.29 | 562 |
| 5-9 | (R) | (R)CH$_3$ | | | | (a) | C$_{30}$H$_{36}$FN$_7$O$_3$ | 562.29 | 562.2 |
| 5-10 | (R) | | | —(CH$_2$)$_3$— | | H | C$_{30}$H$_{34}$FN$_7$O$_2$ | 544.28 | 544.3 |
| 5-11 | (S) | | | —(CH$_2$)$_3$— | | H | C$_{30}$H$_{34}$FN$_7$O$_2$ | 544.28 | 544.2 |

(a) CH$_2$CH$_2$OH

TABLE 6

A

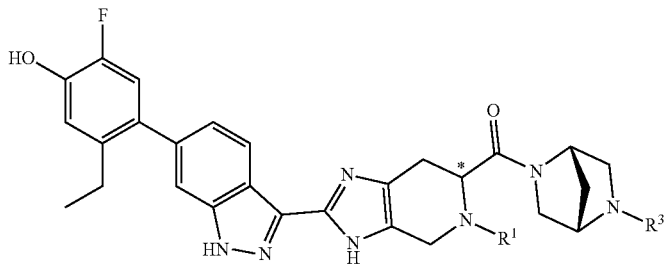

B

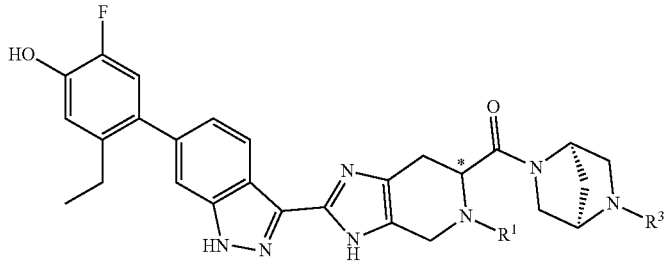

| Ex. No. | * | $R^1$ | $R^3$ | Formula | Calc [M + H]$^+$ | Found [M + H]$^+$ |
|---|---|---|---|---|---|---|
| 6-1 | A | H | H | C$_{27}$H$_{28}$FN$_7$O$_2$ | 502.23 | 502.2 |
| 6-2 | A | CH$_3$ | CH$_3$ | C$_{29}$H$_{32}$FN$_7$O$_2$ | 530.26 | 530 |
| 6-3 | A | nPr | H | C$_{30}$H$_{34}$FN$_7$O$_2$ | 544.28 | 544.3 |
| 6-4 | A | nPr | CH$_3$ | C$_{31}$H$_{36}$FN$_7$O$_2$ | 558.29 | 558.3 |
| 6-5 | A | iPr | CH$_3$ | C$_{31}$H$_{36}$FN$_7$O$_2$ | 558.29 | 558.3 |
| 6-6 | A | iPr | H | C$_{30}$H$_{34}$FN$_7$O$_2$ | 544.28 | 544.2 |
| 6-7 | A | (R) nPr | CH$_3$ | C$_{31}$H$_{36}$FN$_7$O$_2$ | 558.29 | 558.2 |
| 6-8 | B | (S) C$_2$H$_5$ | CH$_3$ | C$_{30}$H$_{34}$FN$_7$O$_2$ | 544.28 | 544.3 |
| 6-9 | A | (S) C$_2$H$_5$ | CH$_3$ | C$_{30}$H$_{34}$FN$_7$O$_2$ | 544.28 | 544.2 |
| 6-10 | B | (S) nPr | CH$_3$ | C$_{31}$H$_{36}$FN$_7$O$_2$ | 558.29 | 558.2 |
| 6-11 | B | (R) nPr | CH$_3$ | C$_{31}$H$_{36}$FN$_7$O$_2$ | 558.29 | 558.2 |
| 6-12 | A | (R) C$_2$H$_5$ | CH$_3$ | C$_{30}$H$_{34}$FN$_7$O$_2$ | 544.28 | 544.3 |
| 6-13 | B | (R) C$_2$H$_5$ | CH$_3$ | C$_{30}$H$_{34}$FN$_7$O$_2$ | 544.28 | 544.3 |

TABLE 7

| Ex. No. | * | R¹ | R³ | Formula | Calc [M + H]⁺ | Found [M + H]⁺ |
|---|---|---|---|---|---|---|
| 7-1 | | CH₃ | CH₃ | $C_{29}H_{34}FN_7O_2$ | 532.28 | 532.2 |
| 7-2 | | CH₃ | iPr | $C_{31}H_{38}FN_7O_2$ | 560.31 | 560.1 |
| 7-3 | | CH₃ | cpropyl | $C_{31}H_{36}FN_7O_2$ | 558.29 | 558.1 |
| 7-4 | | CH₃ | cpentyl | $C_{33}H_{40}FN_7O_2$ | 586.32 | 586.0 |
| 7-5 | | CH₃ | cbutyl | $C_{32}H_{38}FN_7O_2$ | 572.31 | 572.1 |
| 7-6 | | CH₃ | (a) | $C_{31}H_{38}FN_7O_3$ | 576.30 | 576.0 |
| 7-7 | | iPr | CH₃ | $C_{31}H_{38}FN_7O_2$ | 560.31 | 560.3 |
| 7-8 | | iPr | iPr | $C_{33}H_{42}FN_7O_2$ | 588.34 | 588.2 |
| 7-9 | (R) | iPr | CH₃ | $C_{31}H_{38}FN_7O_2$ | 560.31 | 560.2 |
| 7-10 | | CH₃ | H | $C_{28}H_{32}FN_7O_2$ | 518.26 | 518.2 |
| 7-11 | | nPr | H | $C_{30}H_{36}FN_7O_2$ | 546.29 | 546.2 |
| 7-12 | | iPr | H | $C_{30}H_{36}FN_7O_2$ | 546.29 | 546.2 |

(a) (CH₂)₂OCH₃

TABLE 9

| Ex. No. | * | ** | R¹ | R⁵ | R⁶ | Formula | Calc [M + H]⁺ | Found [M + H]⁺ |
|---|---|---|---|---|---|---|---|---|
| 9-1 | | (S) | CH₃ | —(CH₂)₄— | | $C_{31}H_{36}FN_7O_2$ | 558.29 | 558.2 |
| 9-2 | | (S) | CH₃ | —(CH₂)₅— | | $C_{32}H_{38}FN_7O_2$ | 572.31 | 572.3 |
| 9-3 | | (S) | C₂H₅ | —(CH₂)₄— | | $C_{32}H_{38}FN_7O_2$ | 572.31 | 572.2 |
| 9-4 | | (R) | CH₃ | —(CH₂)₄— | | $C_{31}H_{36}FN_7O_2$ | 558.29 | 558.2 |
| 9-5 | (S) | (S) | CH₃ | —(CH₂)₄— | | $C_{31}H_{36}FN_7O_2$ | 558.29 | 558.2 |
| 9-6 | (R) | (S) | CH₃ | —(CH₂)₄— | | $C_{31}H_{36}FN_7O_2$ | 558.29 | 558.2 |
| 9-7 | (S) | (S) | CH₃ | —(CH₂)₅— | | $C_{32}H_{38}FN_7O_2$ | 572.31 | 572.2 |
| 9-8 | (R) | (S) | CH₃ | —(CH₂)₅— | | $C_{32}H_{38}FN_7O_2$ | 572.31 | 572.3 |
| 9-9 | | (S) | nPr | —(CH₂)₄— | | $C_{33}H_{40}FN_7O_2$ | 586.32 | 585.8 |
| 9-10 | | (S) | iPr | —(CH₂)₄— | | $C_{33}H_{40}FN_7O_2$ | 586.32 | 585.8 |
| 9-11 | | (R) | iPr | —(CH₂)₄— | | $C_{33}H_{40}FN_7O_2$ | 586.32 | 586.3 |
| 9-12 | | (R) | C₂H₅ | —(CH₂)₄— | | $C_{32}H_{38}FN_7O_2$ | 572.31 | 572.2 |
| 9-13 | | (R) | nPr | —(CH₂)₄— | | $C_{33}H_{40}FN_7O_2$ | 586.32 | 586.2 |
| 9-14 | | (S) | nPr | CH₃ | CH₃ | $C_{31}H_{38}FN_7O_2$ | 560.31 | 560.4 |
| 9-15 | | (R) | CH₃ | —(CH₂)₅— | | $C_{32}H_{38}FN_7O_2$ | 572.31 | 571.7 |
| 9-16 | | (S) | CH₃ | CH₃ | CH₃ | $C_{29}H_{34}FN_7O_2$ | 532.28 | 531.8 |
| 9-17 | (S) | (S) | C₂H₅ | —(CH₂)₄— | | $C_{32}H_{38}FN_7O_2$ | 572.31 | 572.3 |
| 9-18 | (R) | (S) | C₂H₅ | —(CH₂)₄— | | $C_{32}H_{38}FN_7O_2$ | 572.31 | 572.3 |
| 9-19 | | (R) | iPr | CH₃ | CH₃ | $C_{31}H_{38}FN_7O_2$ | 560.31 | 560.3 |

TABLE 9-continued

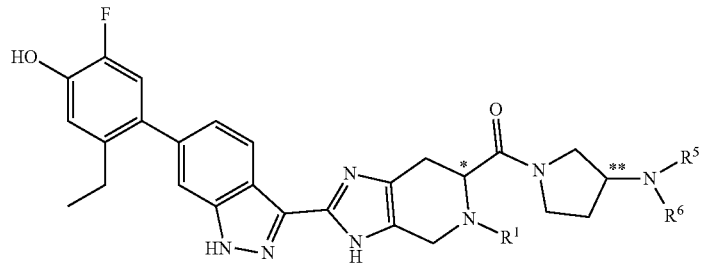

| Ex. No. | * | ** | R¹ | R⁵ | R⁶ | Formula | Calc [M + H]⁺ | Found [M + H]⁺ |
|---|---|---|---|---|---|---|---|---|
| 9-20 | (S) | (S) | nPr | CH₃ | CH₃ | $C_{31}H_{38}FN_7O_2$ | 560.31 | 560.2 |
| 9-21 | (R) | (S) | nPr | CH₃ | CH₃ | $C_{31}H_{38}FN_7O_2$ | 560.31 | 560.3 |
| 9-22 |  | (S) | nPr | —(CH₂)₅— |  | $C_{34}H_{42}FN_7O_2$ | 600.34 | 600.3 |
| 9-23 |  | (S) | C₂H₅ | CH₃ | CH₃ | $C_{30}H_{36}FN_7O_2$ | 546.29 | 546.2 |
| 9-24 |  | (S) | C₂H₅ | —(CH₂)₅— |  | $C_{33}H_{40}FN_7O_2$ | 586.32 | 586.3 |
| 9-25 | (S) | (S) | iPr | —(CH₂)₄— |  | $C_{33}H_{40}FN_7O_2$ | 586.32 | 586.6 |
| 9-26 | (R) | (S) | iPr | —(CH₂)₄— |  | $C_{33}H_{40}FN_7O_2$ | 586.32 | 586.3 |
| 9-27 |  | (S) | iPr | —(CH₂)₅— |  | $C_{34}H_{42}FN_7O_2$ | 600.34 | 600.3 |
| 9-28 | (R) | (S) | iPr | CH₃ | CH₃ | $C_{31}H_{38}FN_7O_2$ | 560.31 | 560.2 |
| 9-29 | (S) | (S) | iPr | —(CH₂)₅— |  | $C_{34}H_{42}FN_7O_2$ | 600.339 | 600.3 |
| 9-30 | (R) | (S) | iPr | —(CH₂)₅— |  | $C_{34}H_{42}FN_7O_2$ | 600.339 | 600.3 |
| 9-31 | (S) | (S) | nPr | —(CH₂)₅— |  | $C_{34}H_{42}FN_7O_2$ | 600.339 | 600.6 |
| 9-32 | (R) | (S) | nPr | —(CH₂)₅— |  | $C_{34}H_{42}FN_7O_2$ | 600.339 | 600.6 |
| 9-33 | (R) | (S) | C₂H₅ | CH₃ | CH₃ | $C_{30}H_{36}FN_7O_2$ | 546.292 | 546.2 |
| 9-34 | (S) | (S) | C₂H₅ | CH₃ | CH₃ | $C_{30}H_{36}FN_7O_2$ | 546.292 | 546.2 |

TABLE 10

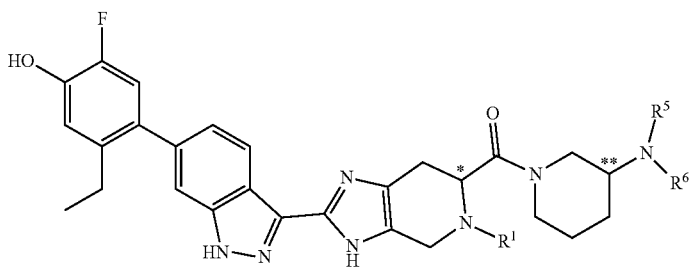

| Ex. No. | * | ** | R¹ | R⁵ | R⁶ | Formula | Calc [M + H]⁺ | Found [M + H]⁺ |
|---|---|---|---|---|---|---|---|---|
| 10-1 | (R) | (S) | CH₃ | CH₃ | CH₃ | $C_{30}H_{36}FN_7O_2$ | 546.29 | 546.3 |
| 10-2 | (R) | (S) | C₂H₅ | CH₃ | CH₃ | $C_{31}H_{38}FN_7O_2$ | 560.31 | 560.3 |
| 10-3 | (R) | (R) | C₂H₅ | CH₃ | CH₃ | $C_{31}H_{38}FN_7O_2$ | 560.31 | 560.3 |
| 10-4 | (S) | (S) | CH₃ | CH₃ | CH₃ | $C_{30}H_{36}FN_7O_2$ | 546.29 | 546.2 |
| 10-5 | (S) | (R) | CH₃ | CH₃ | CH₃ | $C_{30}H_{36}FN_7O_2$ | 546.29 | 546.2 |
| 10-6 | (S) | (S) | C₂H₅ | CH₃ | CH₃ | $C_{31}H_{38}FN_7O_2$ | 560.31 | 560.3 |
| 10-7 | (S) | (R) | C₂H₅ | CH₃ | CH₃ | $C_{31}H_{38}FN_7O_2$ | 560.31 | 560.2 |

TABLE 11

| Ex. No. | * | ** | R¹ | Formula | Calc [M + H]⁺ | Found [M + H]⁺ |
|---|---|---|---|---|---|---|
| 11-1 |  | (S) | CH₃ | $C_{32}H_{38}FN_7O_2$ | 572.31 | 571.8 |
| 11-2 |  | (S) | C₂H₅ | $C_{33}H_{40}FN_7O_2$ | 586.32 | 586.8 |
| 11-3 |  | (S) | nPr | $C_{34}H_{42}FN_7O_2$ | 600.34 | 599.7 |
| 11-4 |  | (S) | iPr | $C_{34}H_{42}FN_7O_2$ | 600.34 | 599.8 |
| 11-5 | (R) | (S) | CH₃ | $C_{32}H_{38}FN_7O_2$ | 572.31 | 572.8 |

TABLE 12

| Ex. No. | * | R¹ | R¹⁰ | R¹¹ | Formula | Calc [M + H]⁺ | Found [M + H]⁺ |
|---|---|---|---|---|---|---|---|
| 12-1 |  | CH₃ | C₂H₅ | C₂H₅ | $C_{30}H_{38}FN_7O_2$ | 548.31 | 547.8 |
| 12-2 |  | CH₃ | CH₃ | CH₃ | $C_{28}H_{34}FN_7O_2$ | 520.28 | 520.3 |
| 12-3 |  | CH₃ | —(CH₂)₄— |  | $C_{30}H_{36}FN_7O_2$ | 546.29 | 546.2 |
| 12-4 |  | iPr | CH₃ | CH₃ | $C_{30}H_{38}FN_7O_2$ | 548.31 | 548.2 |
| 12-5 |  | iPr | —(CH₂)₄— |  | $C_{32}H_{40}FN_7O_2$ | 574.32 | 574.6 |
| 12-6 |  | nPr | CH₃ | CH₃ | $C_{30}H_{38}FN_7O_2$ | 548.31 | 548.3 |
| 12-7 |  | nPr | —(CH₂)₄— |  | $C_{32}H_{40}FN_7O_2$ | 574.32 | 574.3 |
| 12-8 |  | C₂H₅ | C₂H₅ | C₂H₅ | $C_{31}H_{40}FN_7O_2$ | 562.32 | 561.8 |
| 12-9 |  | nPr | C₂H₅ | C₂H₅ | $C_{32}H_{42}FN_7O_2$ | 576.34 | 575.9 |
| 12-10 |  | iPr | C₂H₅ | C₂H₅ | $C_{32}H_{42}FN_7O_2$ | 576.34 | 575.8 |
| 12-11 | (S) | iPr | CH₃ | CH₃ | $C_{30}H_{38}FN_7O_2$ | 548.31 | 548.4 |
| 12-12 | (R) | iPr | CH₃ | CH₃ | $C_{30}H_{38}FN_7O_2$ | 548.31 | 548.2 |
| 12-13 | (S) | C₂H₅ | C₂H₅ | C₂H₅ | $C_{31}H_{40}FN_7O_2$ | 562.32 | 562.7 |
| 12-14 | (R) | C₂H₅ | C₂H₅ | C₂H₅ | $C_{31}H_{40}FN_7O_2$ | 562.32 | 562.7 |
| 12-15 | (S) | iPr | C₂H₅ | C₂H₅ | $C_{32}H_{42}FN_7O_2$ | 576.34 | 576.7 |
| 12-16 | (R) | iPr | C₂H₅ | C₂H₅ | $C_{32}H_{42}FN_7O_2$ | 576.34 | 576.6 |

TABLE 13

| Ex. No. | * | R$^1$ | R$^{12}$ | Formula | Calc [M + H]$^+$ | Found [M + H]$^+$ |
|---|---|---|---|---|---|---|
| 13-1 |  | CH$_3$ | CH$_3$ | C$_{30}$H$_{36}$FN$_7$O$_2$ | 546.29 | 546 |
| 13-2 |  | nPr | CH$_3$ | C$_{32}$H$_{40}$FN$_7$O$_2$ | 574.32 | 574.2 |
| 13-3 |  | iPr | CH$_3$ | C$_{32}$H$_{40}$FN$_7$O$_2$ | 574.32 | 574.3 |
| 13-4 |  | C$_2$H$_5$ | CH$_3$ | C$_{31}$H$_{38}$FN$_7$O$_2$ | 560.31 | 560.2 |
| 13-5 | (S) | nPr | CH$_3$ | C$_{32}$H$_{40}$FN$_7$O$_2$ | 574.32 | 574.6 |
| 13-6 | (R) | nPr | CH$_3$ | C$_{32}$H$_{40}$FN$_7$O$_2$ | 574.32 | 574.6 |
| 13-7 |  | nPr | C$_2$H$_5$ | C$_{33}$H$_{42}$FN$_7$O$_2$ | 588.34 | 588 |
| 13-8 |  | nPr | iPr | C$_{34}$H$_{44}$FN$_7$O$_2$ | 602.35 | 602 |
| 13-9 |  | cBu | CH$_3$ | C$_{33}$H$_{40}$FN$_7$O$_2$ | 586.32 | 587 |
| 13-10 |  | cBu | CH$_2$CH$_2$OH | C$_{34}$H$_{42}$FN$_7$O$_3$ | 616.33 | 616 |
| 13-11 | (S) | nPr | C$_2$H$_5$ | C$_{33}$H$_{42}$FN$_7$O$_2$ | 588.34 | 588.6 |
| 13-12 | (R) | nPr | C$_2$H$_5$ | C$_{33}$H$_{42}$FN$_7$O$_2$ | 588.34 | 588.6 |
| 13-13 | (S) | nPr | iPr | C$_{34}$H$_{44}$FN$_7$O$_2$ | 602.35 | 602.7 |
| 13-14 | (R) | nPr | iPr | C$_{34}$H$_{44}$FN$_7$O$_2$ | 602.35 | 602.8 |

TABLE 14

| Ex. No. | * | ** | R$^1$ | R$^{12}$ | Formula | Calc [M + H]$^+$ | Found [M + H]$^+$ |
|---|---|---|---|---|---|---|---|
| 14-1 |  | (S) | CH$_3$ | CH$_3$ | C$_{30}$H$_{36}$FN$_7$O$_2$ | 546.29 | 546 |
| 14-2 |  | (R) | CH$_3$ | CH$_3$ | C$_{30}$H$_{36}$FN$_7$O$_2$ | 546.29 | 547 |
| 14-3 | (S) | (S) | CH$_3$ | CH$_3$ | C$_{30}$H$_{36}$FN$_7$O$_2$ | 546.29 | 545.8 |
| 14-4 | (S) | (R) | CH$_3$ | CH$_3$ | C$_{30}$H$_{36}$FN$_7$O$_2$ | 546.29 | 545.7 |
| 14-5 |  | (R) | iPr | CH$_3$ | C$_{32}$H$_{40}$FN$_7$O$_2$ | 574.32 | 575 |
| 14-6 | (R) | (S) | CH$_3$ | CH$_3$ | C$_{30}$H$_{36}$FN$_7$O$_2$ | 546.29 | 545.7 |
| 14-7 | (R) | (R) | CH$_3$ | CH$_3$ | C$_{30}$H$_{36}$FN$_7$O$_2$ | 546.29 | 545.7 |
| 14-8 |  | (S) | iPr | CH$_3$ | C$_{32}$H$_{40}$FN$_7$O$_2$ | 574.32 | 574 |
| 14-9 |  | (R) | CH$_3$ | iPr | C$_{32}$H$_{40}$FN$_7$O$_2$ | 574.32 | 574.3 |
| 14-10 |  | (S) | CH$_3$ | iPr | C$_{32}$H$_{40}$FN$_7$O$_2$ | 574.32 | 574.3 |
| 14-11 |  | (R) | nPr | CH$_3$ | C$_{32}$H$_{40}$FN$_7$O$_2$ | 574.32 | 574 |
| 14-12 |  | (R) | C$_2$H$_5$ | CH$_3$ | C$_{33}$H$_{38}$FN$_7$O$_2$ | 560.31 | 561 |
| 14-13 |  | (S) | nPr | H | C$_{33}$H$_{38}$FN$_7$O$_2$ | 560.31 | 560.3 |
| 14-14 |  | (S) | nPr | CH$_3$ | C$_{32}$H$_{40}$FN$_7$O$_2$ | 574.32 | 574 |
| 14-15 |  | (S) | nPr | iPr | C$_{34}$H$_{44}$FN$_7$O$_2$ | 602.35 | 602 |
| 14-16 |  | (S) | CH$_3$ | H | C$_{29}$H$_{34}$FN$_7$O$_2$ | 532.28 | 532.2 |
| 14-17 |  | (S) | C$_2$H$_5$ | H | C$_{30}$H$_{36}$FN$_7$O$_2$ | 546.29 | 546.2 |
| 14-18 |  | (S) | C$_2$H$_5$ | iPr | C$_{33}$H$_{42}$FN$_7$O$_2$ | 588.34 | 588.3 |
| 14-19 |  | (R) | nPr | iPr | C$_{34}$H$_{44}$FN$_7$O$_2$ | 602.35 | 602.3 |
| 14-20 |  | (R) | nPr | H | C$_{33}$H$_{38}$FN$_7$O$_2$ | 560.31 | 560.3 |
| 14-21 |  | (R) | iPr | iPr | C$_{34}$H$_{44}$FN$_7$O$_2$ | 602.35 | 620.3 |
| 14-22 |  | (R) | iPr | H | C$_{33}$H$_{38}$FN$_7$O$_2$ | 560.31 | 560.3 |
| 14-23 | (S) | (R) | iPr | CH$_3$ | C$_{32}$H$_{40}$FN$_7$O$_2$ | 574.32 | 574.2 |
| 14-24 | (R) | (R) | iPr | CH$_3$ | C$_{32}$H$_{40}$FN$_7$O$_2$ | 574.32 | 574.7 |

TABLE 15

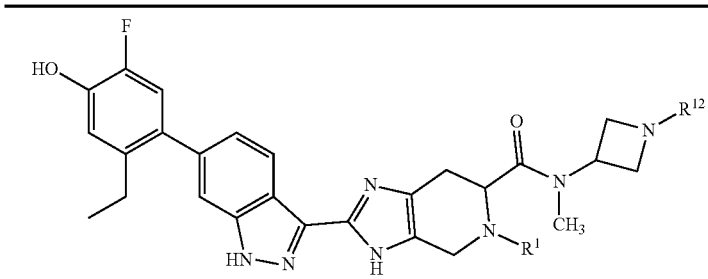

| Ex. No. | R¹ | R¹³ | R¹² | Formula | Calc [M + H]⁺ | Found [M + H]⁺ |
|---|---|---|---|---|---|---|
| 15-1 | CH₃ | H | CH₃ | C₂₇H₃₀FN₇O₂ | 504.24 | 504 |
| 15-2 | cPr | H | cPr | C₃₁H₃₄FN₇O₂ | 556.28 | 556.3 |
| 15-3 | CH₃ | CH₃ | CH₃ | C₂₈H₃₂FN₇O₂ | 518.26 | 518 |
| 15-4 | iPr | H | CH₃ | C₂₉H₃₄FN₇O₂ | 532.28 | 532.2 |
| 15-5 | nPr | H | CH₃ | C₂₉H₃₄FN₇O₂ | 532.28 | 532.2 |
| 15-6 | C₂H₅ | H | CH₃ | C₂₈H₃₂FN₇O₂ | 518.26 | 517.8 |

TABLE 16

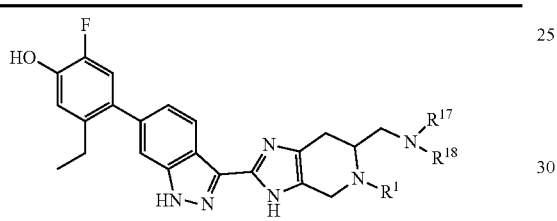

| Ex. No. | R¹ | R¹⁷ | R¹⁸ | Formula | Calc [M + H]⁺ | Found [M + H]⁺ |
|---|---|---|---|---|---|---|
| 16-1 | H | —(CH₂)₅— | | C₂₇H₃₁FN₆O | 475.25 | 475.1 |
| 16-2 | CH₃ | CH₃ | tBu | C₂₈H₃₅FN₆O | 491.29 | 491.1 |
| 16-3 | CH₃ | —(CH₂)₅— | | C₂₈H₃₃FN₆O | 489.27 | 489.3 |
| 16-4 | CH₃ | —(CH₂)₂O(CH₂)₂— | | C₂₇H₃₁FN₆O₂ | 491.25 | 491.1 |
| 16-5 | CH₃ | —(CH₂)₃— | | C₂₆H₂₉FN₆O | 461.24 | 461.2 |
| 16-6 | CH₃ | CH₃ | cpropyl | C₂₇H₃₁FN₆O | 475.25 | 475.1 |

TABLE 17

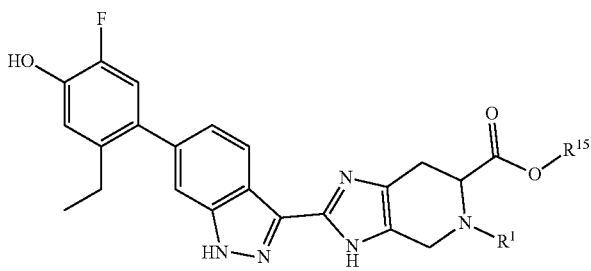

| Ex. No. | R¹ | R¹⁵ | Formula | Calc [M + H]⁺ | Found [M + H]⁺ |
|---|---|---|---|---|---|
| 17-1 | H | CH₃ | C₂₃H₂₂FN₅O₃ | 436.17 | 436.0 |
| 17-2 | H | cpropyl | C₂₅H₂₄FN₅O₃ | 462.19 | 462 |
| 17-3 | H | (CH₂)₂N(CH₃)₂ | C₂₆H₂₉FN₆O₃ | 493.23 | 493 |
| 17-4 | H | CH₂CH₂OH | C₂₄H₂₄FN₅O₄ | 466.18 | 466.1 |

TABLE 17-continued
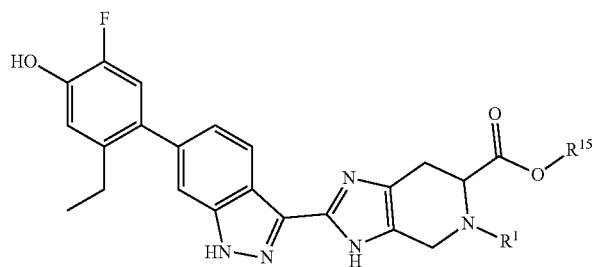
| Ex. No. | R¹ | R¹⁵ | Formula | Calc [M + H]⁺ | Found [M + H]⁺ |
|---|---|---|---|---|---|
| 17-5 | H | ─piperidine-N-CH₃ | $C_{28}H_{31}FN_6O_3$ | 519.24 | 519.2 |
| 17-6 | H | ─tetrahydropyran | $C_{27}H_{28}FN_5O_4$ | 506.21 | 506.1 |
| 17-7 | H | ─(R)-pyrrolidine-NH | $C_{26}H_{27}FN_6O_3$ | 491.21 | 491 |
| 17-8 | H | ─cyclohexyl | $C_{28}H_{30}FN_5O_3$ | 504.23 | 505 |
| 17-9 | H | ─(S)-tetrahydrofuran | $C_{26}H_{26}FN_5O_4$ | 492.20 | 493 |
| 17-10 | CH₃ | ─piperidine-N-CH₃ | $C_{29}H_{32}F_2N_6O_3$ | 551.25 | 553 |
| 17-11 | CH₃ | ─tetrahydrofuran | $C_{27}H_{27}F_2N_5O_4$ | 524.20 | 524.5 |
| 17-12 | CH₃ | ─pyrrolidine-NH | $C_{27}H_{28}F_2N_6O_3$ | 523.22 | 523 |

TABLE 18
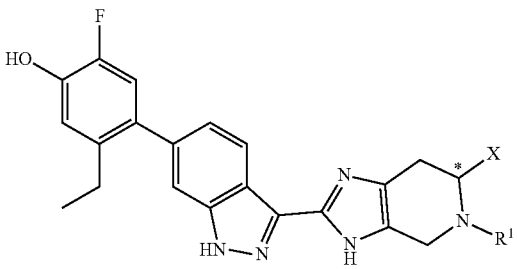
| Ex. No. | * | R¹ | X | Formula | Calc [M + H]⁺ | Found [M + H]⁺ |
|---|---|---|---|---|---|---|
| 18-1 | | CH₃ | CH₂OH | $C_{23}H_{24}FN_5O_2$ | 422.19 | 422.1 |
| 18-2 | | 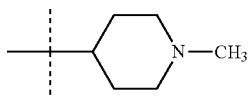 | CH₂OH | $C_{28}H_{33}FN_6O_2$ | 505.27 | 505.2 |
| 18-3 | | (CH₂)₂NHCH₃ | CH₂OH | $C_{25}H_{29}FN_6O_2$ | 465.23 | 465.2 |
| 18-4 | (R) | 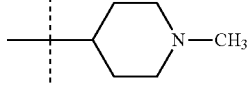 | CH₂OH | $C_{28}H_{33}FN_6O_2$ | 505.27 | 505 |
| 18-5 | (S) | 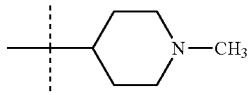 | CH₂OH | $C_{28}H_{33}FN_6O_2$ | 505.27 | 505 |
| 18-6 | (R) | (CH₂)₂NHCH₃ | CH₂OH | $C_{25}H_{29}FN_6O_2$ | 465.23 | 465 |
| 18-1 | (S) | (CH₂)₂NHCH₃ | CH₂OH | $C_{25}H_{29}FN_6O_2$ | 465.23 | 465 |
TABLE 19
| Ex. No. | R¹ | Formula | Calc [M + H]⁺ | Found [M + H]⁺ |
|---|---|---|---|---|
| 19-1 | 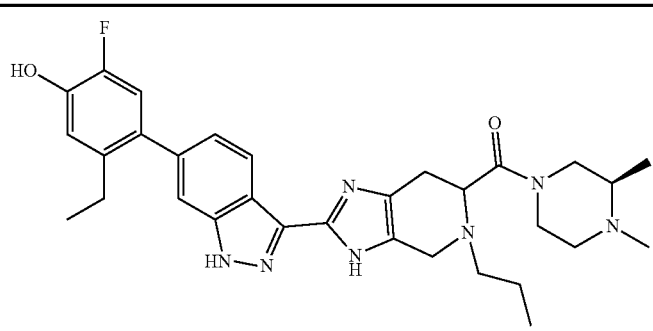 | $C_{31}H_{38}FN_7O_2$ | 560.31 | 560 |
| 19-2 | 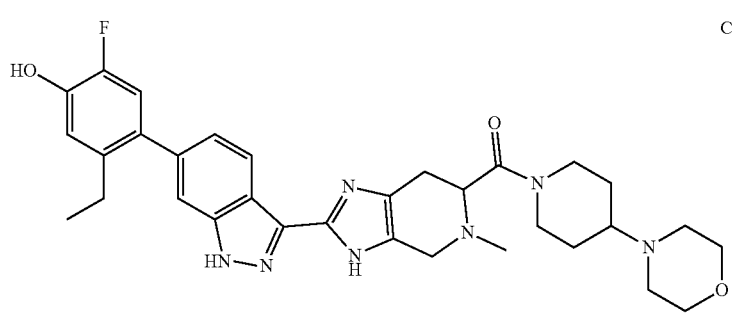 | $C_{32}H_{38}FN_7O_3$ | 588.30 | 588 |

TABLE 19-continued

| Ex. No. | R¹ | Formula | Calc [M + H]⁺ | Found [M + H]⁺ |
|---|---|---|---|---|
| 19-3 | | $C_{32}H_{38}FN_7O_2$ | 572.31 | 572.1 |
| 19-4 | | $C_{26}H_{27}FN_6O_2$ | 475.22 | 475 |
| 19-5 | | $C_{27}H_{29}FN_6O_2$ | 489.23 | 489 |
| 19-6 | | $C_{28}H_{31}FN_6O_2$ | 503.25 | 503 |
| 19-7 | | $C_{27}H_{29}FN_6O_2$ | 489.23 | 490 |

TABLE 19-continued

| Ex. No. | R¹ | Formula | Calc [M + H]⁺ | Found [M + H]⁺ |
|---|---|---|---|---|
| 19-8 | 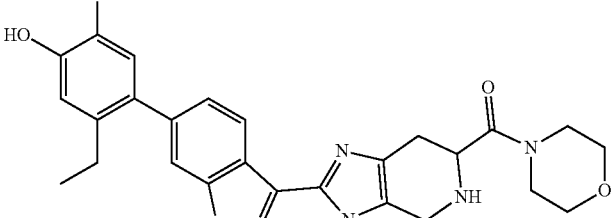 | $C_{26}H_{27}FN_6O_3$ | 491.21 | 492 |
| 19-9 | 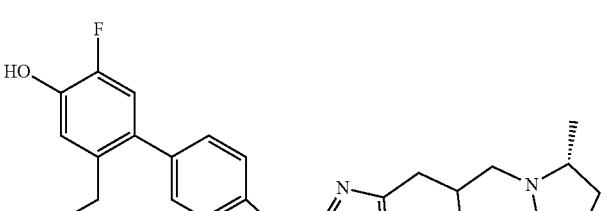 | $C_{28}H_{33}FN_6O$ | 489.27 | 489.2 |
| 19-10 | 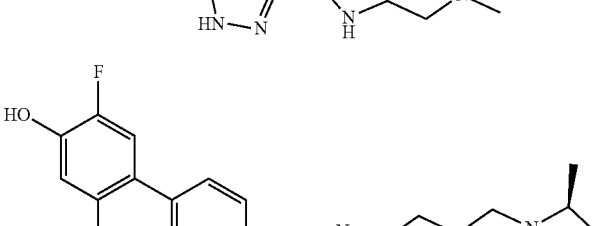 | $C_{28}H_{33}FN_6O$ | 489.27 | 489.2 |

Biological Assays

The compounds of the invention have been characterized in one or more of the following biological assays.

Assay 1: Biochemical JAK Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM MgCl₂, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and IC₅₀ values were determined from a 4-parameter robust fit model with the Prism software (GraphPad Software). Results were expressed as pIC₅₀ (negative logarithm of IC₅₀) and subsequently converted to pK$_i$ (negative logarithm of dissociation constant, Ki) using the Cheng-Prusoff equation.

Test compounds having a lower K$_i$ value or higher pK$_i$ value in each of the four JAK assays show greater inhibition of JAK activity.

Assay 2: Cellular JAM Potency Assay

The AlphaScreen JAM cellular potency assay was carried out by measuring interleukin-13 (IL-13, R&D Systems) induced STAT6 phosphorylation in BEAS-2B human lung epithelial cells (ATCC). The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

BEAS-2B cells were grown at 37° C. in a 5% CO₂ humidified incubator in 50% DMEM/50% F-12 medium (Life Technologies) supplemented with 10% FBS (Hyclone), 100 U/mL penicillin, 100 μg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 254 medium, and were allowed to adhere overnight in the incubator. On day 2 of the assay, the medium was removed and replaced with 12 µL of assay buffer (Hank's Balanced Salt Solution/HBSS, 25 mM HEPES, and 1 mg/ml bovine serum albumin/BSA) containing dose-responses of test compounds. Compounds were serially diluted in DMSO and then diluted another 1000-fold in media to bring the final DMSO concentration to 0.1%. Cells were incubated with test compounds at 37° C. for 1 h, and followed by the addition of 12 µl of pre-warmed IL-13 (80 ng/mL in assay buffer) for stimulation. After incubating at 37° C. for 30 min, the assay buffer (containing compound and IL-13) was removed, and 10 µL of cell lysis buffer (25 mM HEPES, 0.1% SDS, 1% NP-40, 5 mM $MgCl_2$, 1.3 mM EDTA, 1 mM EGTA, and supplement with Complete Ultra mini protease inhibitors and PhosSTOP from Roche Diagnostics). The plates were shaken at ambient temperature for 30 min before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software. Results may also be expressed as the negative logarithm of the $IC_{50}$ value, $pIC_{50}$.

Test compounds having a lower $IC_{50}$ value or higher $pIC_{50}$ value in this assay show greater inhibition of IL-13 induced STAT6 phosphorylation.

In Vitro Assay Results

Selected compounds of the invention were tested in the four JAK enzyme assays; JAK1, JAK2, JAK3, and Tyk2, and the BEAS-2B cellular potency assay described above. As shown in Table 19 below, it was observed that JAK1 enzyme potency was predictive of both pan-JAK enzyme activity and cellular potency in the BEAS-2B assay. Therefore, all of the compounds made were tested in the JAK1 enzyme assay and the BEAS-2B cellular assay and the great majority were also tested in the JAK3 enzyme assay. All of the compounds exhibited JAK1 $K_i$ values between 0.04 nM and 0.6 nM ($pK_i$ between 9.2 and 10.4). The compounds tested in the JAK3 enzyme assay exhibited $K_i$ values between 0.08 nM and 0.5 nM ($pK_i$ between 9.3 and 10.1). The compounds tested exhibited $IC_{50}$ values in the BEAS-2B assay between 3 nM and 100 nM ($pIC_{50}$ between 7 and 8.5).

TABLE 20

| Example Number | JAK1 $K_i$ (nM) | JAK2 $K_i$ (nM) | JAK3 $K_i$ (nM) | Tyk2 $K_i$ (nM) | BEAS-2B $IC_{50}$ (nM) |
|---|---|---|---|---|---|
| 1 | 0.05 | 0.02 | 0.08 | 0.25 | 5.0 |
| 3 | 0.06 | 0.02 | 0.10 | 0.40 | 5.9 |
| 5 | 0.08 | | 0.20 | | 6.5 |
| 6 | 0.10 | | 0.25 | | 4.2 |
| 7 | 0.06 | | 0.16 | | 5.4 |
| 1-2 | 0.05 | 0.03 | 0.16 | 0.08 | 7.8 |
| 1-12 | 0.06 | 0.06 | 0.25 | 0.25 | 5.9 |
| 1-37 | 0.10 | 0.04 | 0.50 | 1.26 | 5.9 |
| 2-15 | 0.06 | | 0.16 | | 4.0 |
| 9-21 | 0.06 | 0.03 | 0.25 | 1.00 | 4.0 |
| 12-14 | 0.06 | | 0.2 | | 3.3 |

Assay 3: Pharmacokinetics in Plasma and Lung in Mouse

Plasma and lung levels of test compounds and ratios thereof were determined in the following manner. BALB/c mice from Charles River Laboratories were used in the assay. Test compounds were individually formulated in 20% propylene glycol in pH 4 citrate buffer at a concentration of 0.2 mg/mL and 50 µL of the dosing solution was introduced into the trachea of a mouse by oral aspiration. At various time points (typically 0.167, 2, 6, 24 hr) post dosing, blood samples were removed via cardiac puncture and intact lungs were excised from the mice. Blood samples were centrifuged (Eppendorf centrifuge, 5804R) for 4 minutes at approximately 12,000 rpm at 4° C. to collect plasma. Lungs were padded dry, weighed, and homogenized at a dilution of 1:3 in sterile water. Plasma and lung levels of test compound were determined by LC-MS analysis against analytical standards constructed into a standard curve in the test matrix. A lung to plasma ratio was determined as the ratio of the lung AUC in µg hr/g to the plasma AUC in µg hr/mL, where AUC is conventionally defined as the area under the curve of test compound concentration vs. time. Compounds of the invention exhibited exposure in lung from one to two orders of magnitude greater than exposure in plasma in mouse. All of the compounds profiled in this assay exhibited a half-life between about 4.5 and about 14 hours.

Assay 4: Murine (Mouse) Model of IL-13 Induced pSTAT6 Induction in Lung Tissue

Il-13 is an important cytokine underlying the pathophysiology of asthma (Kudlacz et al. *Eur. J. Pharmacol*, 2008, 582, 154-161). IL-13 binds to cell surface receptors activating members of the Janus family of kinases (JAK) which then phosphorylate STAT6 and subsequently activates further transcription pathways. In the described model, a dose of IL-13 was delivered locally into the lungs of mice to induce the phosphorylation of STAT6 (pSTAT6) which is then measured as the endpoint.

Adult balb/c mice from Harlan were used in the assay. On the day of study, animals were lightly anesthetized with isoflurane and administered either vehicle or test compound (1 mg/mL, 50 µL total volume over several breaths) via oral aspiration. Animals were placed in lateral recumbency post dose and monitored for full recovery from anesthesia before being returned to their home cage. Four hours later, animals were once again briefly anesthetized and challenged with either vehicle or IL-13 (0.03 µg total dose delivered, 50 µL total volume) via oral aspiration before being monitored for recovery from anesthesia and returned to their home cage. One hour after vehicle or IL-13 administration, lungs were collected for both pSTAT6 detection using an anti-pSTAT6 ELISA (rabbit mAb capture/coating antibody; mouse mAb detection/report antibody: anti-pSTAT6-pY641; secondary antibody: anti-mouse IgG-HRP) and analyzed for total drug concentration as described above in Assay 3.

Selected compounds of the invention were tested in the assay. Activity in the model is evidenced by a decrease in the level of pSTAT6 present in the lungs of treated animals at 5 hours compared to the vehicle treated, IL-13 challenged control animals. The difference between the control animals which were vehicle-treated, IL-13 challenged and and the control animals which were vehicle-treated, vehicle challenged dictated the 0% and 100% inhibitory effect, respectively, in any given experiment. Exemplary compounds of the invention were tested in the assay, and exhibited inhibition of STAT6 phosphorylation at 4 hours after IL-13 challenge as documented below. The compound of 9-22 was noted as an exception under the conditions of the assay.

Confirming the relevance of the JAK-STAT pathway in airway inflammation, compounds which have demonstrated in vivo target engagement in the IL13-induced pSTAT6 mouse model are subsequently tested and proven to be efficacious in a mouse model of allergen-induced eosinophilic inflammation.

In Vivo Assay Results

Selected compounds of the invention were characterized in both the pharmacokinetic assay (Assay 3) and pharmacodynamic assay (Assay 4). A good correlation was observed between test compound concentration in lung determined in the pharmacokinetic assay and in the pharmacodynamic assay at a similar time points post dosing. Observation of significant compound concentration in the mouse lung in the pharmacodynamic assay confirmed that the observed inhibition of IL-13 induced pSTAT6 induction was a result of the activity of the test compound.

In the following table, for the ratio of lung exposure to plasma exposure (Assay 3), A denotes a ratio 100-200, B denotes a ratio between 50 and 100, and C denotes a ratio between 20 and 50. For the percent inhibition of IL-13 induced pSTAT6 induction (Assay 4), A represents between 60% and 80% inhibition, B represents between 40% and 60% inhibition and C represents between 25% and 40% inhibition.

TABLE 21

| Example Number | Lung to Plasma ratio Assay 3 | pSTAT6 inhibition Assay 4 |
|---|---|---|
| 1 | A | A |
| 3 | B | B |
| 5 | B | B |
| 6 | B | B |
| 7 | B | B |
| 1-18 | B | A |
| 1-28 | C | B |
| 1-29 | C | A |
| 1-37 |  | C |
| 2-2 | C | B |
| 2-3 |  | A |
| 2-8 | C | C |
| 2-9 | C | C |
| 2-15 | C | B |
| 3-2 | B | A |
| 3-5 |  | A |
| 3-24 |  | C |
| 5-8 | C | A |
| 9-3 | A | B |
| 9-21 |  | B |
| 12-8 |  | A |
| 12-14 | B | B |
| 13-2 | A | A |
| 13-5 | A | C |
| 13-6 | B | B |

Assay 5: Murine Model of *Alternaria alternata*-Induced Eosinophilic Inflammation of the Lung Airway eosinophilia is a hallmark of human asthma. *Alternaria alternata* is a fungal aeroallergen that can exacerbate asthma in humans and induces eosinophilic inflammation in the lungs of mice (Havaux et al. *Clin Exp Immunol.* 2005 February; 139(2):179-88). In mice, it has been demonstrated that *alternaria* indirectly activates tissue resident type 2 innate lymphoid cells in the lung, which respond to (e.g. IL-2 and IL-7) and release JAK-dependent cytokines (e.g. IL-5 and IL-13) and coordinate eosinophilic inflammation (Bartemes et al. *J Immunol.* 2012 Feb. 1; 188(3):1503-13).

Seven- to nine-week old male C57 mice from Taconic were used in the study. On the day of study, animals were lightly anesthetized with isoflurane and administered either vehicle or test compound (0.03-1.0 mg/mL, 50 µL total volume over several breaths) via oropharyngeal aspiration. Animals were placed in lateral recumbency post dose and monitored for full recovery from anesthesia before being returned to their home cage. One hour later, animals were once again briefly anesthetized and challenged with either vehicle or *alternaria* extract (200 ug total extract delivered, 50 µL total volume) via oropharyngeal aspiration before being monitored for recovery from anesthesia and returned to their home cage. Forty-eight hours after *alternaria* administration, bronchoalveolar lavage fluid (BALF) was collected and eosinophils were counted in the BALF using the Advia 120 Hematology System (Siemens).

Selected compounds of the invention demonstrating in vivo activity in the IL-13-pSTAT6 pharmacodynamic assay were tested in this *alternaria* assay. Activity in the model is evidenced by a decrease in the level of eosinophils present in the BALF of treated animals at forty-eight hours compared to the vehicle treated, *alternaria* challenged control animals. Data are expressed as percent inhibition of the vehicle treated, *alternaria* challenged BALF eosinophils response. To calculate percent inhibition, the number of BALF eosinophils for each condition is converted to percent of the average vehicle treated, *alternaria* challenged BALF eosinophils and subtracted from one-hundred percent. Exemplary compounds of the invention were tested in the assay and exhibited inhibition of BALF eosinophil counts at forty-eight hours after *alternaria* challenge as documented below.

In Vivo Assay Results

All of the compounds tested demonstrated a range of inhibition (73%-93%) of *alternaria*-induced BALF eosinophils. The following table reflects the maximum statistically significant percent inhibition of the vehicle treated, *alternaria* challenged level of eosinophil induction.

TABLE 22

| Example Number | Percent Inhibition of Alternaria-induced BALF Eosinophils |
|---|---|
| 1 | 90 |
| 3 | 93 |
| 6 | 73 |
| 7 | 91 |

Assay 6: IL-5 Mediated Eosinophil Survival Assay

The potency of the test compound for IL-5 mediated eosinophil survival was measured in human eosinophils isolated from human whole blood (AllCells). Because IL-5 signals through JAK, this assay provides a measure of JAK cellular potency.

Human eosinophils were isolated from fresh human whole blood (AllCells) of healthy donors. Blood was mixed with 4.5% Dextran (Sigma-Aldrich) in a 0.9% sodium chloride solution (Sigma-Aldrich). Red blood cells were left to sediment for 35 minutes. The leukocyte rich upper layer was removed and layered over Ficoll-Paque (GE Healthcare) and centrifuged at 600 g for 30 minutes. The plasma and mononuclear cell layers were removed before the granulocyte layer was lysed with water to remove any contaminating red blood cells. Eosinophils were further purified using a human eosinophil isolation kit (Miltenyi Biotec). A fraction of the purified eosinophils were incubated with anti-CD16 FITC (Miltenyi Biotec) for 10 minutes at 4° C. in the dark. Purity was analyzed using a LSRII flow cytometer (BD Biosciences).

Cells were cultured in a 37° C., 5% $CO_2$ humidified incubator in RPMI 1640 (Life Technologies) supplemented with 10% Heat Inactivated Fetal Bovine Serum (FBS, Life Technologies), 2 mM Glutamax (Life Technologies), 25 mM HEPES (Life Technologies) and 1× Pen/Strep (Life Technologies). Cells were seeded at 10,000 cells/well in media (50 µL). The plate was centrifuged at 300 g for 5 minutes and supernatants removed. Compounds were serially diluted in DMSO and then diluted another 500-fold to a 2× final assay concentration in media. Test compounds (50 µL/well) were added to cells, and incubated at 37° C., 5% $CO_2$ for 1 hour, followed by the addition of IL-5 (R&D Systems; final concentrations 1 ng/mL and 10 pg/ml) in pre-warmed assay media (50 µL) for 72 hours.

After cytokine stimulation, cells were centrifuged at 300 g for 5 min and washed twice with cold DPBS (Life Technologies). To access viability and apoptosis, cells were incubated with Propidium Iodide (Thermo Fisher Scientific) and APC Annexin V (BD Biosciences) and analyzed using a LSRII flow cytometer (BD Biosciences). $IC_{50}$ values were determined from analysis of the viability curves of percent cell viability vs compound concentration. Data are expressed as $pIC_{50}$ (negative decadic logarithm $IC_{50}$) values. The compound of example 1 exhibited a $pIC_{50}$ value of 7.3±0.4 in the presence of 10 pg/ml IL-5 and a $pIC_{50}$ value of 5.7±0.1 in the presence of 1 ng/ml IL-5.

Assay 7: Cellular JAK Potency Assay: Inhibition of IL-2/Anti-CD3 Stimulated IFNγ in Human PBMCs The potency of the test compound for inhibition of interleukin-2 (IL-2)/anti-CD3 stimulated interferon gamma (IFNγ) was measured in human peripheral blood mononuclear cells (PBMCs) isolated from human whole blood (Stanford Blood Center). Because IL-2 signals through JAK, this assay provides a measure of JAK cellular potency.

(1) Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Heat Inactivated Fetal Bovine Serum (FBS, Life Technologies), 2 mM Glutamax (Life Technologies), 25 mM HEPES (Life Technologies) and 1×Pen/Strep (Life Technologies). Cells were seeded at 200,000 cells/well in media (50 µL) and cultured for 1 h. Compounds were serially diluted in DMSO and then diluted another 500-fold (to a 2× final assay concentration) in media. Test compounds (100 µL/well) were added to cells, and incubated at 37° C., 5% $CO_2$ for 1 h, followed by the addition of IL-2 (R&D Systems; final concentration 100 ng/mL) and anti-CD3 (BD Biosciences; final concentration 1 µg/mL) in pre-warmed assay media (50 µL) for 24 h.

(2) After cytokine stimulation, cells were centrifuged at 500 g for 5 min and supernatants removed and frozen at −80° C. To determine the inhibitory potency of the test compound in response to IL-2/anti-CD3, supernatant IFNγ concentrations were measured via ELISA (R&D Systems). $IC_{50}$ values were determined from analysis of the inhibition curves of concentration of IFNγ vs compound concentration. Data are expressed as $pIC_{50}$ (negative decadic logarithm $IC_{50}$) values. The compound of Example 1 exhibited a $pIC_{50}$ value of about 6.9 in this assay. The compound of Example 3 exhibited a $pIC_{50}$ value of about 7.2 in this assay. The compound of Example 1-37 exhibited a $pIC_{50}$ value of about 7.2 in this assay.

Assay 8: Cellular JAK Potency Assay: Inhibition of IL-2 Stimulated pSTAT5 in CD4+ T Cells The potency of the test compound for inhibition of interleukin-2 (IL-2)/anti-CD3 stimulated STAT5 phosphorylation was measured in CD4-positive (CD4+) T cells in human peripheral blood mononuclear cells (PBMCs) isolated from human whole blood (Stanford Blood Center) using flow cytometry. Because IL-2 signals through JAK, this assay provides a measure of JAK cellular potency.

CD4+ T cells were identified using a phycoerythrobilin (PE) conjugated anti-CD4 antibody (Clone RPA-T4, BD Biosciences), while an Alexa Fluor 647 conjugated anti-pSTAT5 antibody (pY694, Clone 47, BD Biosciences) was used to detect STAT5 phosphorylation.

(1) The protocol of Assay 7 paragraph (1) was followed with the exception that the cytokine stimulation with anti-CD3 was performed for 30 min instead of 24 h.

(2) After cytokine stimulation, cells were fixed with pre warmed fix solution (200 µL; BD Biosciences) for 10 min at 37° C., 5% $CO_2$, washed twice with DPBS buffer (1 mL, Life Technologies), and resuspended in ice cold Perm Buffer III (1000 µL, BD Biosciences) for 30 min at 4° C. Cells were washed twice with 2% FBS in DPBS (FACS buffer), and then resuspended in FACS buffer (100 µL) containing anti-CD4 PE (1:50 dilution) and anti-CD3 anti-CD3Alexa Fluor 647 (1:5 dilution) for 60 min at room temperature in the dark. After incubation, cells were washed twice in FACS buffer before being analyzed using a LSRII flow cytometer (BD Biosciences). To determine the inhibitory potency of test compounds in response to IL-2/anti-CD3, the median fluorescent intensity (MFI) of pSTAT5 was measured in CD4+ T cells. $IC_{50}$ values were determined from analysis of the inhibition curves of MFI vs compound concentration. Data are expressed as $pIC_{50}$ (negative decadic logarithm $IC_{50}$) values. The compound of Example 1 exhibited a $pIC_{50}$ value of about 7.3 in this assay. The compound of Example 3 exhibited a $pIC_{50}$ value of about 7.7 in this assay. The compound of Example 1-37 exhibited a $pIC_{50}$ value of about 8.1 in this assay.

Assay 9: Cellular JAK Potency Assay: Inhibition of IL-4 Stimulated pSTAT6 in CD3+ T Cells The potency of the test compound for inhibition of interleukin-4 (IL-4) stimulated STAT6 phosphorylation was measured in CD3-positive (CD3+) T cells in human peripheral blood mononuclear cells (PBMCs) isolated from human whole blood (Stanford Blood Center) using flow cytometry. Because IL-4 signals through JAK, this assay provides a measure of JAK cellular potency.

CD3+ T cells were identified using a phycoerythrobilin (PE) conjugated anti-CD3 antibody (Clone UCHT1, BD Biosciences), while an Alexa Fluor 647 conjugated anti-pSTAT6 antibody (pY641, Clone 18/P, BD Biosciences) was used to detect STAT6 phosphorylation.

Human peripheral blood mononuclear cells (PBMC) were isolated from human whole blood of healthy donors as in Assays 7 and 8. Cells were seeded at 250,000 cells/well in media (200 µL), cultured for 1 h and then resuspended in assay media (50 µL) (RPMI supplemented with 0.1% bovine serum albumin (Sigma), 2 mM Glutamax, 25 mM HEPES and 1× Penstrep) containing various concentrations of test compounds. Compounds were serially diluted in DMSO and then diluted another 500-fold (to a 2× final assay concentration) in assay media. Test compounds (50 µL) were incubated with cells at 37° C., 5% $CO_2$ for 1 h, followed by the addition of IL-4 (50 μL) (R&D Systems; final concentration 20 ng/mL) in pre-warmed assay media for 30 min. After cytokine stimulation, cells were fixed with pre-warmed fix solution (100 μL) (BD Biosciences) for 10 min at 37° C., 5% $CO_2$, washed twice with FACS buffer (1 mL) (2% FBS in DPBS), and resuspended in ice cold Perm Buffer III (1000 μL) (BD Biosciences) for 30 min at 4° C. Cells were washed twice with FACS buffer, and then resuspended in FACS buffer (100 μL) containing anti-CD3 PE (1:50 dilution) and anti-pSTAT6 Alexa Fluor 647 (1:5 dilution) for 60 min at room temperature in the dark. After incubation, cells were washed twice in FACS buffer before being analyzed using a LSRII flow cytometer (BD Biosciences).

To determine the inhibitory potency of the test compound in response to IL-4, the median fluorescent intensity (MFI) of pSTAT6 was measured in CD3+ T cells. $IC_{50}$ values were determined from analysis of the inhibition curves of MFI vs compound concentration. Data are expressed as $pIC_{50}$ (negative decadic logarithm $IC_{50}$). The compound of Example 1 exhibited a $pIC_{50}$ value of 7.7 in this assay. The compound of Example 3 exhibited a $pIC_{50}$ value of 8 in this assay. The compound of Example 16-4 exhibited a $pIC_{50}$ value of 8.1 in this assay.

Assay 10: Cellular JAK Potency Assay: Inhibition of IL-6 Stimulated pSTAT3 in CD3+ T Cells A protocol analogous to that of Assay 9 was used to determine the potency of the test compound for inhibition of interleuken-6 (IL-6) stimulated STAT3 phosphorylation. An Alexa Fluor 647 conjugated anti-pSTAT3 antibody (pY705, Clone 4/P, BD Biosciences) was used to detect STAT3 phosphorylation. The compound of Example 1 exhibited a $pIC_{50}$ value of 7.2 in this assay. The compound of Example 3 exhibited a $pIC_{50}$ value of 7.4 in this assay.

Crystal Structure

A co-crystal structure was obtained of the compound of Example 2 (an analog of the compounds disclosed herein which was disclosed in the provisional application from which this application takes priority from) bound to human JAK1 at a resolution of 2.28 Å. The ligand was observed to bind in the ATP binding site. Seven specific hydrogen bonding interactions were identified based upon a distance of 3.5 Å or less between donor and acceptor atoms. Of particular note, a hydrogen bonding interaction was identified between the carbonyl of the exocyclic amide of the compound of Example 2 and the sidechain of Arg879 of JAK1. In earlier modeling studies this interaction had been proposed as a way to provide selectivity for JAK1 over other tyrosine kinases, as otherwise closely related kinases (e.g. TRKA, VEGFR, ABL1) did not possess an arginine residue at the equivalent location. The observed results of the hydrogen bonding interaction in the crystal structure and improved kinome selectivity compared to series not possessing the exocyclic amide validate this design hypothesis.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound, or a pharmaceutically acceptable salt thereof, selected from the group consisting of:

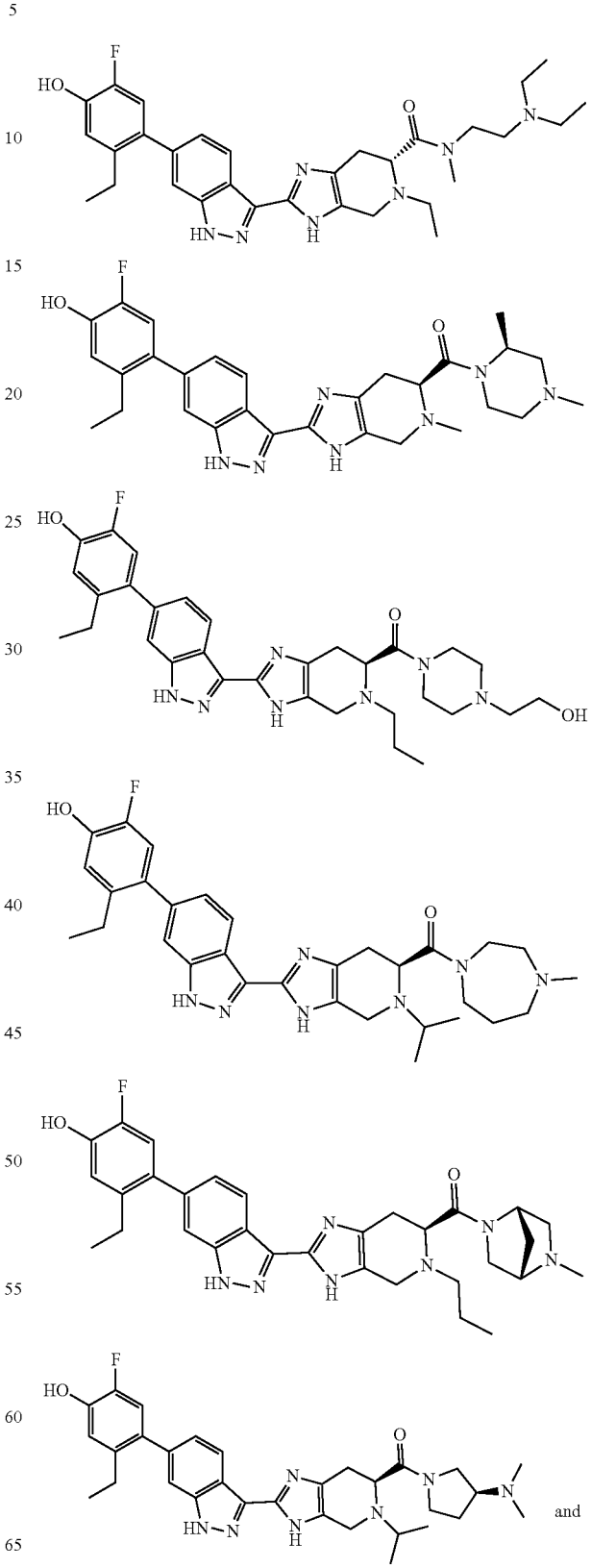

and

-continued

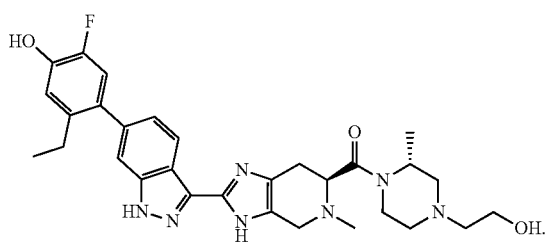

2. The compound of claim 1, or a pharmaceutically acceptable salt thereof, having the formula:

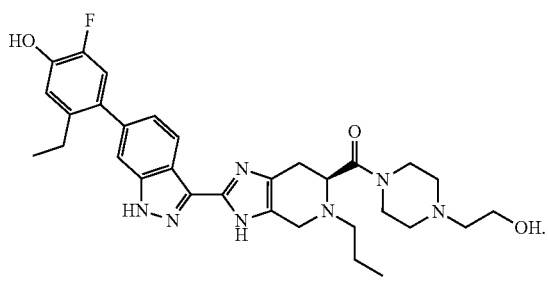 [SMILES: CCCN1Cc2[nH]c(-c3n[nH]c4cc(-c5cc(F)c(O)cc5CC)ccc34)nc2C[C@H]1C(=O)N1CCN(CCO)CC1]

3. The compound of claim 1, or a pharmaceutically acceptable salt thereof, having the formula:

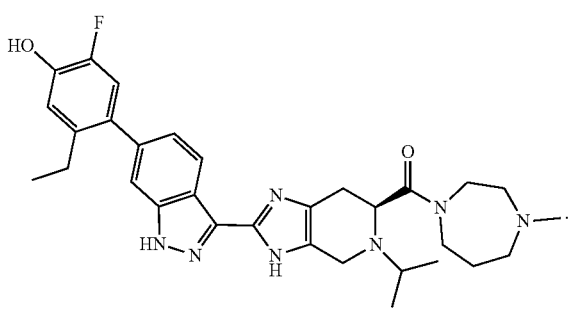 [SMILES: CCc1cc(O)c(F)cc1-c1ccc2c(-c3nc4c([nH]3)CN(C(C)C)[C@H](C(=O)N3CCCN(C)CC3)C4)n[nH]c2c1]

4. The compound of claim 1, or a pharmaceutically acceptable salt thereof, having the formula:

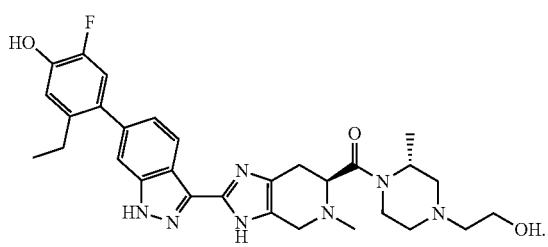 [SMILES: CCc1cc(O)c(F)cc1-c1ccc2c(-c3nc4c([nH]3)CN(C)[C@H](C(=O)N3CCN(CCO)C[C@H]3C)C4)n[nH]c2c1]

5. A pharmaceutical composition comprising a compound of claim 1, or a pharmaceutically acceptable salt thereof, and a pharmaceutically-acceptable carrier.

6. The pharmaceutical composition of claim 5, wherein the compound is a compound of formula:

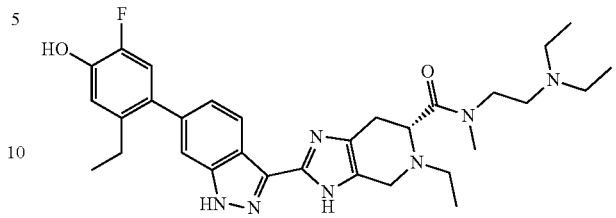

or a pharmaceutically acceptable salt thereof.

7. The pharmaceutical composition of claim 5, wherein the compound is a compound of formula:

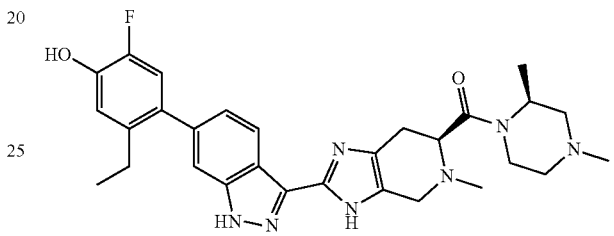

or a pharmaceutically acceptable salt thereof.

8. The pharmaceutical composition of claim 5, wherein the compound is a compound of formula:

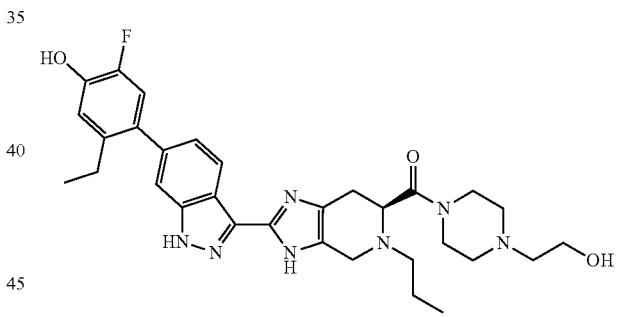

or a pharmaceutically acceptable salt thereof.

9. The pharmaceutical composition of claim 5, wherein the compound is a compound of formula:

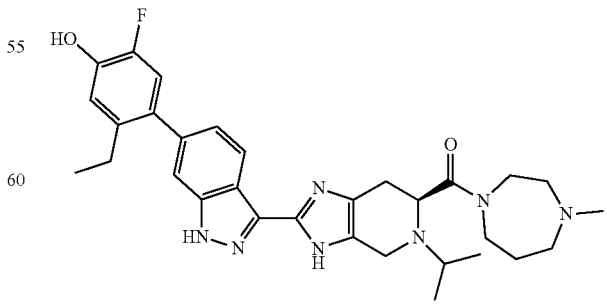

or a pharmaceutically acceptable salt thereof.

10. The pharmaceutical composition of claim 5, wherein the compound is a compound of formula:

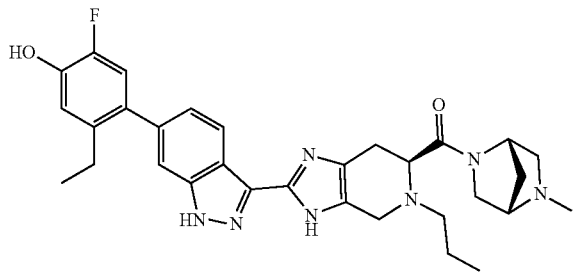 [SMILES: CCCN1Cc2[nH]c(-c3n[nH]c4cc(-c5cc(F)c(O)cc5CC)ccc34)nc2C[C@H]1C(=O)N1C[C@@H]2C[C@H]1CN2C]

or a pharmaceutically acceptable salt thereof.

11. The pharmaceutical composition of claim 5, wherein the compound is a compound of formula:

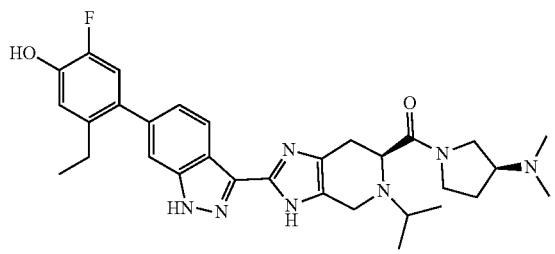 [SMILES: CCc1cc(O)c(F)cc1-c1ccc2c(-c3nc4c([nH]3)CN(C(C)C)[C@H](C(=O)N3CC[C@H](N(C)C)C3)C4)n[nH]c2c1]

or a pharmaceutically acceptable salt thereof.

12. The pharmaceutical composition of claim 5, wherein the compound is a compound of formula:

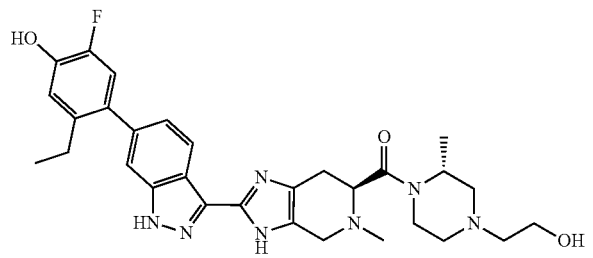 [SMILES: CCc1cc(O)c(F)cc1-c1ccc2c(-c3nc4c([nH]3)CN(C)[C@H](C(=O)N3CCN(CCO)C[C@H]3C)C4)n[nH]c2c1]

or a pharmaceutically acceptable salt thereof.

13. A method of treating a respiratory disease in a mammal, the method comprising administering to the mammal a compound of claim 1, or a pharmaceutically acceptable salt thereof.

14. The method of claim 13, wherein the respiratory disease is cystic fibrosis, pneumonitis, idiopathic pulmonary fibrosis, acute lung injury, acute respiratory distress syndrome, bronchitis, emphysema, bronchiolitis obliterans, or sarcoidosis.

15. The method of claim 13, wherein the respiratory disease is asthma.

16. The method of claim 13, wherein the respiratory disease is chronic obstructive pulmonary disease.

17. The method of claim 13, wherein the respiratory disease is an eosinophilic disease, a helminthic infection, pulmonary arterial hypertension, lymphangioleiomyomatosis, bronchiectasis, an infiltrative pulmonary disease, drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, lung graft-versus-host disease, or immune-checkpoint-inhibitor induced pneumonitis.

18. A method of treating lung transplant rejection in a mammal, the method comprising administering to the mammal a compound of claim 1, or a pharmaceutically acceptable salt thereof.

19. The method of claim 18, wherein the lung transplant rejection is primary graft dysfunction, organizing pneumonia, acute rejection, or lymphocytic bronchiolitis.

20. The method of claim 18, wherein the lung transplant rejection is acute lung transplant rejection.

21. The method of claim 18, wherein the lung transplant rejection is chronic lung allograft dysfunction.

22. The method of claim 18, wherein the lung transplant rejection is bronchiolitis obliterans, restrictive chronic lung allograft dysfunction, or neutrophilic allograft dysfunction.

* * * * *